(12) United States Patent
Liao et al.

(10) Patent No.: US 11,786,550 B2
(45) Date of Patent: Oct. 17, 2023

(54) GRNA TARGETING HPK1 AND A METHOD FOR EDITING HPK1 GENE

(71) Applicant: Beijing Synthetic Vaccine Biosciences Co., Ltd, Beijing (CN)

(72) Inventors: Xuebin Liao, Beijing (CN); Jingwen Si, Beijing (CN)

(73) Assignee: Beijing Synthetic Vaccine Biosciences Co., Ltd, Beijing (CN)

( * ) Notice: Subject to any disclaimer, the term of this patent is extended or adjusted under 35 U.S.C. 154(b) by 434 days.

(21) Appl. No.: 16/648,907

(22) PCT Filed: Sep. 20, 2018

(86) PCT No.: PCT/CN2018/106636
§ 371 (c)(1),
(2) Date: Mar. 19, 2020

(87) PCT Pub. No.: WO2019/057102
PCT Pub. Date: Mar. 28, 2019

(65) Prior Publication Data
US 2022/0023340 A1    Jan. 27, 2022

(30) Foreign Application Priority Data

Sep. 20, 2017 (CN) .......................... 201710853090.2

(51) Int. Cl.
*A61K 35/17* (2015.01)
*A61P 35/00* (2006.01)
*C12N 9/22* (2006.01)
*C12N 15/113* (2010.01)

(52) U.S. Cl.
CPC .............. *A61K 35/17* (2013.01); *A61P 35/00* (2018.01); *C12N 9/22* (2013.01); *C12N 15/1137* (2013.01); *C12Y 207/11001* (2013.01)

(58) Field of Classification Search
CPC ........... A61K 35/17; A61P 35/00; C12N 9/22; C12N 15/1137; C12Y 207/11001

USPC ....................................................... 424/93.71
See application file for complete search history.

(56) References Cited

FOREIGN PATENT DOCUMENTS

| WO | WO2007041511 A2 | 4/2007 |
| WO | 2016/069282 | 5/2016 |
| WO | WO2016090300 A1 | 6/2016 |
| WO | WO2016196388 A1 | 12/2016 |
| WO | WO2017049166 A1 | 3/2017 |
| WO | 2017/120546 | 7/2017 |
| WO | WO2018081531 A2 | 5/2018 |
| WO | WO2018085275 A1 | 5/2018 |
| WO | WO2019178421 A1 | 9/2019 |

OTHER PUBLICATIONS

International Search Report for PCT/CN2018/106636 dated Dec. 27, 2018, 4 pages.
Sawasdikosol et al., "HPK1 as a novel target for cancer immunotherapy", Immunologic Research, vol. 54, pp. 262-265, Apr. 4, 2012.
Shui et al., "Hematopoietic progenitor kinase 1 negatively regulates T cell receptor signaling and T cell-mediated immune responses", Nature Immunology, vol. 8, No. 1, pp. 84-91, Nov. 19, 2006.
Si, Jingwen et al., "Hematopoietic Progenitor Kinase1 (HPK1) Mediates T Cell Dysfunction and Is a Druggable Target for T Cell-Based Immunotherapies", Cancer Cell, vol. 38(4), pp. 551-566, Oct. 12, 2020.

*Primary Examiner* — Yan Xiao
(74) *Attorney, Agent, or Firm* — NIXON & VANDERHYE, PC

(57) ABSTRACT

Provided is a gRNA targeting HPK1 and a method for editing HPK1 gene. The method can knock out the T cell HPK1 gene, enhance the T cell killing activity, increase the Th1 cytokine level of peripheral blood mononuclear cells, and knock out of the T cell HPK1 gene can also down-regulate the expression of PD-1 and TIM3 on the T cell surface and can inhibit the T cell depletion.

6 Claims, 24 Drawing Sheets
Specification includes a Sequence Listing.

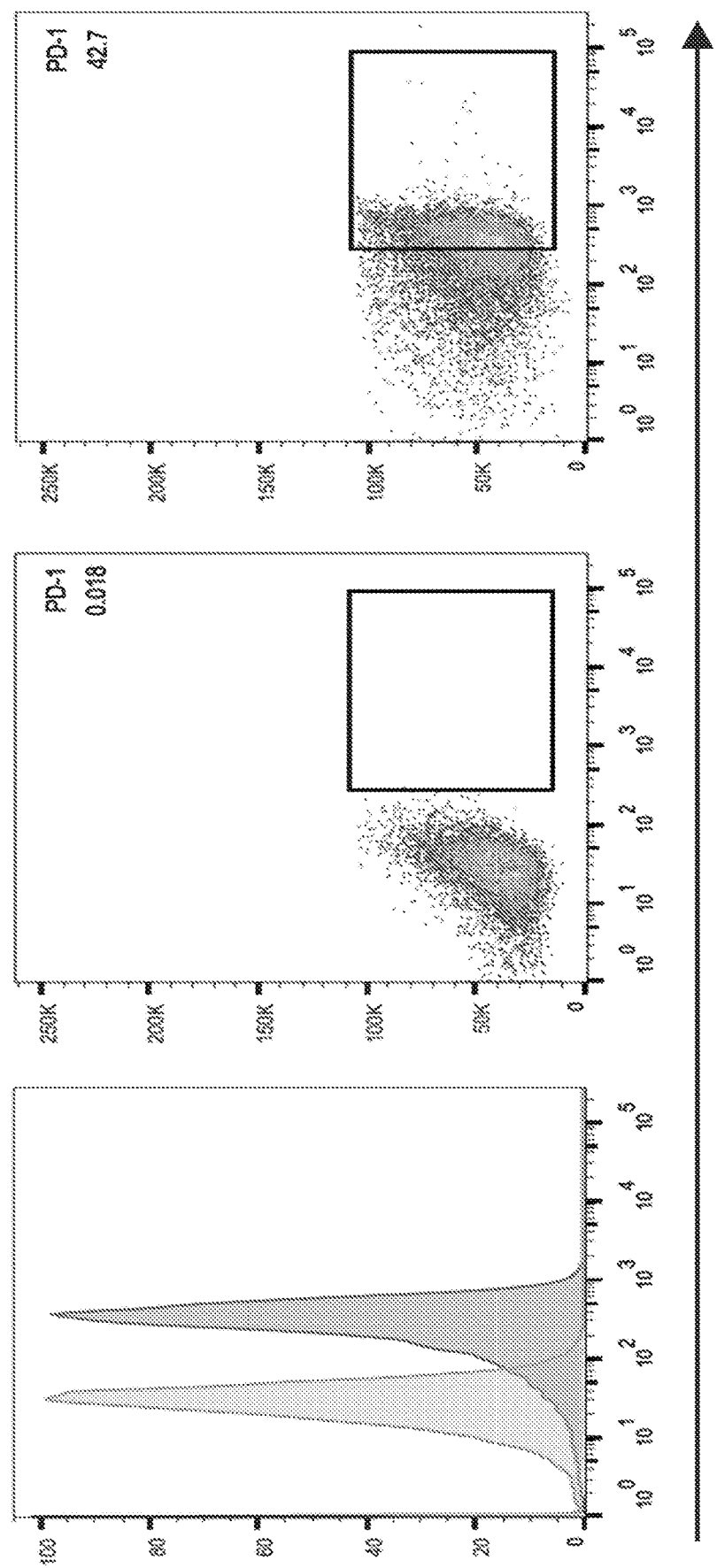
FIG. 20A - Top

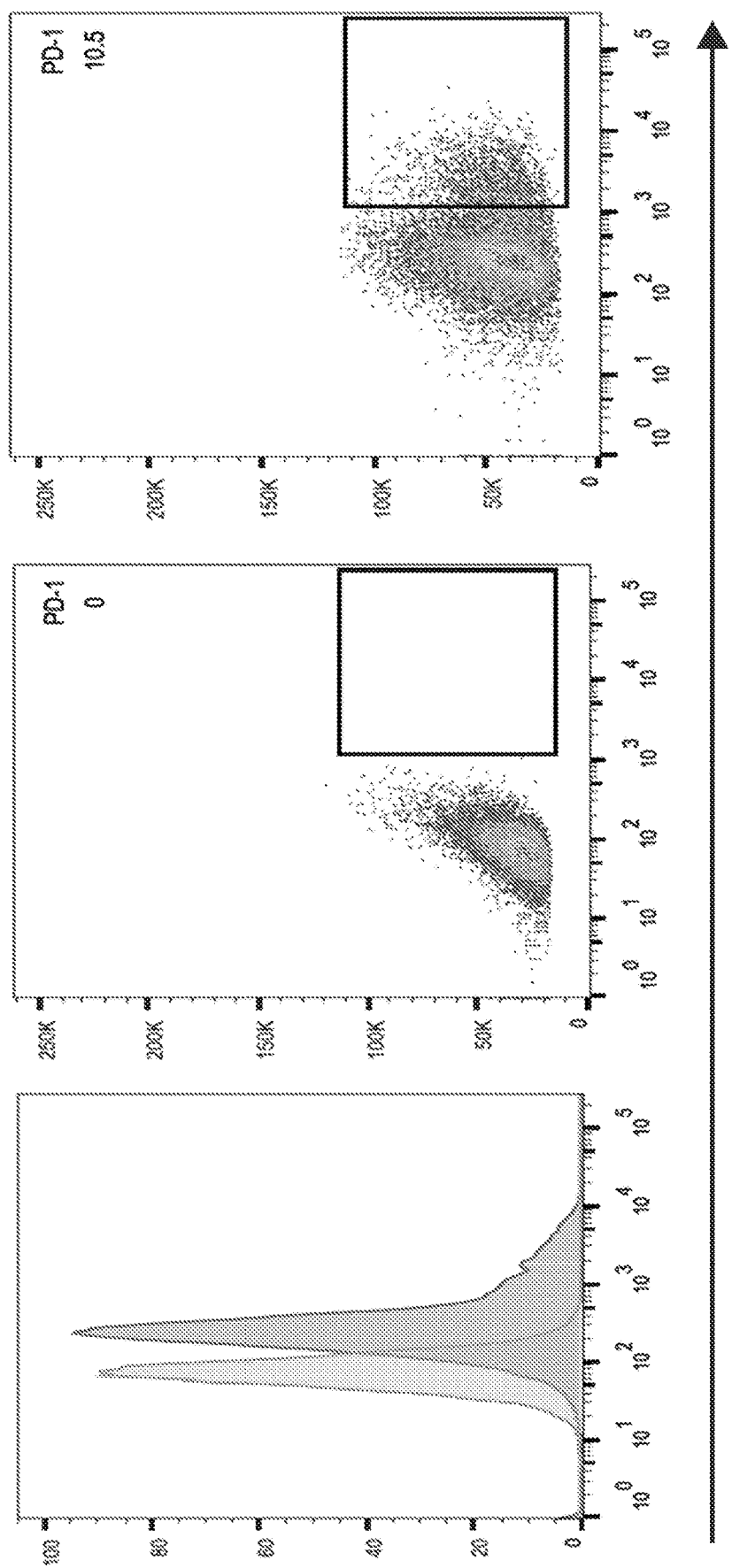
FIG. 20B - Bottom

US 11,786,550 B2

GRNA TARGETING HPK1 AND A METHOD FOR EDITING HPK1 GENE

CROSS REFERENCE TO RELATED APPLICATIONS

This application is the U.S. national phase of International Application No. PCT/CN2018/106636 filed on Sep. 20, 2018 which designated the U.S. and claims priority to Chinese Application No. 201710853090.2, filed on Sep. 20, 2017, the content of each of which is herein incorporated by reference in its entirety.

REFERENCE TO SEQUENCE LISTING SUBMITTED ELECTRONICALLY

The content of the electronically submitted sequence listing (Name: 6891.0210_ST25.txt; Size: 27.8 kilobytes; and Date of Creation: Oct. 14, 2020) is herein incorporated by reference in its entirety.

TECHNICAL FILED

In various embodiments, the present invention relates to the technical field of molecular biology and immunology, and more particularly relates to cancer immunotherapy. For example, in various embodiments, the present invention is generally related to compositions and methods for editing HPK1 gene, cells with an edited HPK1 gene, such as T cells, NK cells and NKT cells, pharmaceutical compositions comprising the cells and methods of using the same, e.g., for the treatment of cancer.

BACKGROUND ART

Tumor is one of the major diseases that threaten human health. In recent years, immunotherapy against tumors has gradually become a research hotspot in cancer therapy. Tumor immune cell therapy is to in vitro modify, culture and expand immune cells collected from the human body, and then return them to the body of the patient to stimulate and enhance the body's own immune function, thereby achieving the effect of inhibiting tumor growth and killing tumor cells.

Among many cancer immunotherapy methods, the one with relatively clear mechanism and effective effect is the chimeric antigen receptor T cell tumor targeted therapy (CAR-T cell therapy) and PD-1 inhibitor therapy. Cellular immunotherapy, including CAR-T, has achieved remarkable success in the treatment of hematologic tumors, but there have been obstacles to conquer solid tumors. The main reason is T cell depletion, decreased activity, and insufficient tumor killing ability. Therefore, to find novel T cell in vitro modification sites and modification methods, enhance T cell activity and killing activity, and inhibit T cell depletion is a future direction of the research and technological development.

Hematopoietic progenitor kinase 1 (abbreviated as hpk1, HPK1, HPK-1, or map4k1) is a hematopoietic-specific serine/threonine protein kinase belonging to the map4k family of mammalian ste20 related protein kinases. Hpk1 is mainly expressed in hematopoietic tissues and cells. Numerous studies have shown that hpk1 is involved in many signaling cascades, including mapk (mitogen-activated protein kinase) signaling, antigen receptor signaling, apoptotic signaling, growth factor signaling, and cytokine signaling etc. There are three activation ways of hpk1, namely serine phosphorylation, threonine phosphorylation or tyrosine phosphorylation. After the PCR technology was first used to clone hpk1 from mouse hematopoietic progenitor cells in 1996, studies have shown that hpk1 is mainly expressed in hematopoietic tissues and cells. Currently, the research on hpk1 is mainly focused on the hematopoietic system. Recent studies have shown that hpk1 may be associated with cancer. Sawasdikosol S. et al.'s study of mouse models found that disrupting the hpk1 gene of T cells and DC cells helps to inhibit the growth of lung cancer cells, and hpk1 is expected to become a new target for anti-tumor immunotherapy. US20160158360 discloses use of a hpk1 antagonist that inhibits hpk1 serine/threonine protein kinase activity in combination with a PD-1 antagonist for the treatment of cancer.

BRIEF SUMMARY

In various embodiments, the present disclosure provides cells, cell compositions, nucleic acids, and vectors related to HPK-1 gene disruption, as well as methods of preparation, and methods of use thereof.

Some embodiments of the present disclosure are directed to immune cells containing a genetic disruption (e.g., a gene knockout) of a HPK-1 gene, and/or an agent that induces or is capable of inducing the genetic disruption. The genetic disruption can comprise a deletion, mutation, and/or insertion in the HPK-1 gene resulting in inactivation, reduced activity, and/or reduced expression of the HPK-1 gene. For example, in some embodiments, the genetic disruption can comprise a deletion of at least a portion of at least one exon (e.g., the first or second exon) of the HPK-1 gene. In any of the embodiments described herein, the genetic disruption can also comprise creation of a double stranded break (DSB) in the HPK-1 gene (e.g., in the first or second exon), which is repaired by non-homologous end joining (NHEJ) that effects insertions and deletions (indels) in the HPK-1 gene. In some embodiments, the genetic disruption can also comprise creation of a double stranded break in the HPK-1 gene, which is repaired by homology-directed repair (HDR) to insert a donor sequence (such as a sequence encoding a CAR described herein) following the DSB. In some embodiments, the genetic disruption can include one or more of the following: the immune cells do not express the endogenous HPK-1 polypeptide, do not contain a contiguous HPK-1 gene, a HPK-1 gene, and/or a functional HPK-1 gene.

Various agents can be used to effect the genetic disruptions herein. For example, in some embodiments, the agent can be an inhibitory nucleic acid molecule, such as an RNA interfering agent. In some embodiments, the inhibitory nucleic acid molecule is, comprises, or encodes a small interfering RNA (siRNA), a microRNA-adapted shRNA, a short hairpin RNA (shRNA), a hairpin siRNA, a precursor microRNA (pre-miRNA) or a microRNA (miRNA). In some embodiments, the inhibitory nucleic acid molecule comprises a sequence complementary to a nucleic acid sequence (e.g., mRNA) of the HPK-1 gene. In some embodiments, the agent can comprise one or more molecules that reduce or are capable of reducing expression of HPK-1 in the immune cell, or a polynucleotide encoding the one or more molecules. In some embodiments, the one or more molecules can be, comprise or encode an antisense molecule, siRNA, shRNA, miRNA, a gene editing nuclease, zinc finger nuclease protein (ZFN), a TAL-effector nuclease (TALEN) or a CRISPR-Cas9 combination that specifically binds to, recognizes, or hybridizes to the HPK-1 gene.

In some specific embodiments, the agent can comprise (a) a gRNA having a targeting domain that is complementary with a target domain of the HPK-1 gene, or a polynucleotide encoding the gRNA; (b) a Cas9 protein, or a polynucleotide encoding the Cas9 protein, or a combination of (a) and (b). In some embodiments, the agent can comprise a ribonucleoprotein complex (or molecular complex or simply complex or RNP) of a Cas9 molecule and a gRNA having a targeting domain that is complementary with a target domain of the HPK-1 gene. Various gRNA and Cas9 proteins are suitable and include those described herein. For example, in some embodiments, the gRNA can have a targeting sequence that is the same or differs no more than 1, 2, or 3 nucleotides from a sequence fully complementary to a target sequence selected from SEQ ID NOs: 1 and 11-15. In some embodiments, the gRNA can have a targeting sequence that is at least 80, 85, 90, 95, 98 or 99% complementary, e.g., fully complementary to a target sequence selected from SEQ ID NOs: 1 and 11-15. The gRNA can be chimeric or modular. In some embodiments, the Cas9 protein is a *S. pyogenes* Cas9. In some embodiments, the Cas9 protein is further modified by inserting a nuclear localization sequence (e.g., inserted at one or both the C- and N-termini of the Cas9 molecule) that can facilitate entry of the Cas9 molecule into the nucleus of mammalian, e.g., human, immune cells. In any of the embodiments herein, the complex of gRNA/Cas9 can cleave the target domain with a double stranded break, which allows repair of the HPK-1 gene via NHEJ or HDR.

Some embodiments are also directed to nucleic acids and vectors encoding the agents herein. Vectors suitable for use herein include, but are not limited to, plasmid vectors and viral vectors, such as retroviral vectors, lentiviral vectors, or other vectors such as adenoviral vectors or adeno-associated vectors. A cell comprising the nucleic acid or vector is also one embodiment of the present disclosure.

In some embodiments, the immune cells herein preferably also comprise a recombinant receptor expressed on the surface of the immune cell or a polynucleotide encoding the recombinant receptor. Typically, the recombinant receptor specifically binds to an antigen, and the immune cell is capable of inducing cytotoxicity, proliferating and/or secreting a cytokine upon binding of the recombinant receptor to the antigen. Various recombinant receptors including those described herein are suitable. For example, in some embodiments, the recombinant receptor is a recombinant T cell receptor. In some embodiments, the recombinant receptor is a chimeric antigen receptor (CAR). Non-limiting useful recombinant TCR and CARs are described herein. For example, in some embodiments, the recombinant receptor (e.g., CAR) can specifically bind to one or more antigens independently selected from ROR1, Her2, L1-CAM, CD19, CD20, CD22, CEA, hepatitis B surface antigen, anti-folate receptor, CD23, CD24, CD30, CD33, CD38, CD276, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule (CD171), MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), cyclin A1 (CCNA1), BCMA and interleukin 12.

Various immune cells can be used for the compositions and methods of the present disclosure. In some embodiments, the immune cells are human cells. In some embodiments, the immune cells include T cells, such as Car-T cells, NKT cells, and NK cells. In some embodiments, the immune cells can be used for adoptive immunotherapy. In some embodiments, the immune cells can be derived from primary cells of a subject suffering from cancer, such as lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and/or medulloblastoma.

The immune cells or cell population with the HPK-1 genetic disruption herein can also be characterized by certain enhanced characteristics compared to control immune cells that do not have the genetic disruption. For example, in some embodiments, the immune cells or cell population with the HPK-1 genetic disruption can be characterized by an enhanced cytotoxicity, reduced apoptosis, improved persistence, and/or reduced exhaustion.

In some embodiments, the present disclosure provides a cell population comprising the immune cells (e.g., T cells such as Car-T cells) herein, which is characterized by a HPK-1 genetic knockout efficiency of at least about 50%, 60%, 65%, 70%, 75%, 80%, 85%, 90% or 95%, e.g., as determined by a method in accordance with the T7E1 assay as described in Example 4 and/or Western Blot method in Example 5. In some embodiments, the cell population is further characterized in that at least about 50%, 75%, 80%, 85%, or 90% of the cells comprise a recombinant receptor (e.g., a chimeric antigen receptor, e.g., as described herein) on cell surface. In some embodiments, the cell population is further characterized in that the percentage of cells in the cell population expressing PD-1, TIM-3, and/or Lag-3 on cell surface, as determined by flow cytometry, is lower than that in a control cell population; the percentage of cells in the cell population expressing Annexin V on cell surface, as determined by flow cytometry, is lower than that in a control cell population; and/or the percentage of cells in the cell population expressing CD107a on cell surface, as determined by flow cytometry, is higher than that in a control cell population.

Some embodiments of the present disclosure are directed to a method of producing an immune cell, for example, a method of altering a T cell. In some embodiments, the method comprises introducing into an immune cell (e.g., T cell) an agent that induces or is capable of inducing a genetic disruption (e.g., gene knockout) of a HPK1 gene. In some embodiments, the method comprises (a) obtaining an immune cell (e.g., T cell) from a human patient (e.g., as described herein); (b) introducing the agent that induces or is capable of inducing HPK-1 genetic disruption in the immune cell (e.g., T cell); and (c) incubating and optionally expanding the immune cell (e.g., T cell) with the agent to provide a HPK-1 gene disrupted immune cell (e.g., T cell) population. In some embodiments, the method further comprises introducing in the immune cell (e.g., T cell) a nucleic acid encoding a recombinant receptor, such as a CAR as described herein, or product thereof. Suitable immune cells and agents include those described herein. For example, in some embodiments, the immune cells can be introduced any of the complex of gRNA/Cas9, for example, that can cleave the target domain with a double stranded break in the HPK-1 gene, which allows repair of the HPK-1 gene via NHEJ or HDR in the immune cells. The immune cell or cell population produced by the methods herein can be characterized by any of the characteristics such as the HPK-1 gene knockout efficiency, the expression of exhaustion markers, PD-1, TIM-3, and/or Lag-3, expression of apoptosis marker Annexin V, expression of cytotoxicity marker CD107a, as described herein.

Some embodiments of the present disclosure are directed to a method of enhancing the function of immune cells for immunotherapy. In some embodiments, the present disclosure provides a method of enhancing cytotoxicity, inhibiting exhaustion, and/or enhancing infiltration in spleen and/or tumors, of an immune cell population, the method comprising contacting the immune cell population with an agent that induces or is capable of inducing a genetic disruption (e.g., gene knockout) of a HPK1 gene. In some embodiments, the method comprises (a) obtaining an immune cell (e.g., T cell) population from a human patient (e.g., as described herein); (b) introducing the agent that induces or is capable of inducing HPK-1 genetic disruption in the immune cell (e.g., T cell) population; and (c) incubating and optionally expanding the immune cell (e.g., T cell) with the agent to provide a HPK-1 gene disrupted immune cell (e.g., T cell) population that has enhanced cytotoxicity, reduced exhaustion, and/or enhanced infiltration in spleen and/or tumors compared to the cell population prior to introducing the agent. In some embodiments, the method further comprises introducing in the immune cell (e.g., T cell) a nucleic acid encoding a recombinant receptor, such as a CAR as described herein, or product thereof. Suitable immune cells and agents include those described herein. For example, in some embodiments, the immune cells can be introduced any of the complex of gRNA/Cas9, for example, that can cleave the target domain with a double stranded break in the HPK-1 gene, which allows repair of the HPK-1 gene via NHEJ or HDR in the immune cells.

Some embodiments of the present disclosure are directed to pharmaceutical compositions comprising the immune cells with the HPK-1 genetic disruption or cell compositions herein.

Some embodiments of the present disclosure are directed to methods of treating a disease or disorder. In some embodiments, the disease or disorder is an infectious disease or condition, an autoimmune disease, an inflammatory disease or a tumor or a cancer. In some embodiments, the disease or disorder can be a cancer or tumor, which is a leukemia, lymphoma, chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, colon cancer, lung cancer, liver cancer, breast cancer, prostate cancer, ovarian cancer, skin cancer, melanoma cancer, bone cancer, brain cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the method comprising administering to a subject in need thereof a therapeutically effective amount of the immune cells with the HPK-1 genetic disruption or cell compositions herein.

In some embodiments, the method comprises (a) obtaining an immune cell (e.g., T cell) from a subject in need of the treatment; (b) introducing an agent that induces or is capable of inducing HPK-1 genetic disruption in the immune cell (e.g., T cell); (c) incubating and optionally expanding the immune cell with the agent to provide a HPK-1 gene disrupted cell population; and (d) administering the HPK-1 gene disrupted cell population to the subject. In some embodiments, the method further comprises (e) introducing in the immune cell (e.g., T cell) a nucleic acid encoding a recombinant receptor, such as a CAR as described herein, or product thereof. The introducing steps of (b) and (e) can occur simultaneously or sequentially in any order. Suitable agents and recombinant receptors include those described herein.

DESCRIPTION OF THE DRAWINGS

Various other advantages and benefits will become apparent to those skilled in the art by reading the detailed descriptions of the following preferred embodiments. The drawings are only for the purpose of illustrating the preferred embodiments and are not to be construed as limiting the present invention.

FIG. 6A compares the killing effect on human chronic myeloid leukemia cell K562 line; FIG. 6B compares the killing effect on lymphoblastoid Raji cell line; and FIG. 6C compares the killing effect on human Burkkit lymphoma cell line Daudi.

FIG. 7A compares the production level of IFN-γ; and FIG. 7B compares the production level of IL-2.

In FIG. 9, NSG mice were inoculated with Raji-ffluc cells, and seven days later treated with $1 \times 10^6$ T cells expressing CD19-CARs containing a 4-1BB/CD3 signaling module or with T cells expressing only EGFRt (4-5 mice per group). Arrows mark the day of T-cell transfer. Tumor growth was analyzed by bioluminescence imaging and results from individual mice are plotted for different CARs. Images from seven day after T cell transfer (d7) to twenty-eight days after transfer (d28) are shown for mice that had received different CART-cells.

FIG. 11A presents graphs showing expression levels of Annexin V/CD107a/PD1/Tim3/Lag3 on cells infiltrating in the tumor tissues. FIG. 11B presents bar graphs showing expression levels of Annexin V and CD107a on Car-T cells infiltrating in tumor tissues; and FIG. 11C presents bar graphs showing expression levels of PD1, Tim3, and Lag3 on Car-T cells infiltrating in the tumor tissues. *P<0.001, P<0.01, *P<0.05 unpaired t test.

In FIG. 15A, NSG mice were inoculated with SKOV3-ffluc cells, and seven days after treated with $1 \times 10^6$ T cells expressing HER2-CARs containing a 4-1BB/CD3 signaling module or with T cells expressing only EGFRt (4-5 mice per group). Arrows mark the day of T-cell transfer. Tumor growth was analyzed by bioluminescence imaging and results from individual mice are plotted for different CARs. Images from seven day after T cell transfer (d7) to twenty-eight days after transfer (d28) are shown for mice that had received different CART-cells. FIG. 15B present graphs showing tumor growth over 28 days of the treated mice (n=6 mice per group). *P<0.001, unpaired t test. FIG. 15C** shows a Kaplan-Meier analysis of survival of mice. SKOV-3-bearing mice were treated with $1 \times 10^6$ CAR T cells (n=6 per group; dot=one mouse).

FIGS. 18A and B show that HPK-1 knockout ameliorates exhaustion of Her2 Car T cells in vivo. FIG. 18A shows the analysis of cytotoxicity marker and FIG. 18B shows the analysis of Exhaustion marker expression of CAR T cells from mice on day 14 after adoptive transfer. *P<0.001, P<0.01, *P<0.05, NS: no significant. unpaired t test.

FIG. 19A shows that the efficiency of infection after transduce CAR-BCMA lentivirus 72 h. FIG. 19B is an image of Western Blot, which shows that HPK-1 gene was efficiently knocked out after electroporosis, with a gRNA:Cas9 protein ratio of about 1:3.

FIG. 20 shows the expression of PD1 in BMCA Car T cells before (top) and after (bottom) knockout of PD-1.

DETAILED DESCRIPTION

Figure 1:
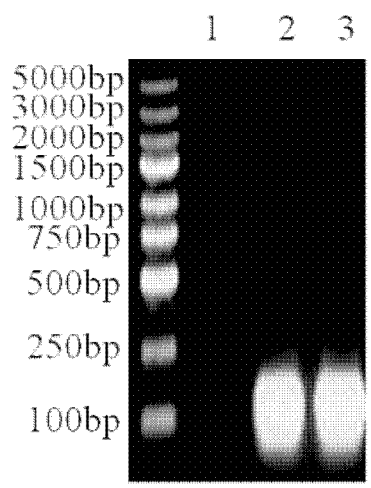
FIG. 1 shows a representative gel electrophoresis image of purified in vitro transcribed gRNA, from left to right: Lane 1 is a blank control NC; Lane 2 is the purified HPK1gRNA mRNA; and Lane 3 is the purified PD1 gRNA mRNA.

Tumor cells and/or cells in the tumor microenvironment often upregulate ligands for PD-1 (such as PD-L1 and PD-L2), which in turn leads to ligation of PD-1 on tumor-specific T cells expressing PD-1, delivering an inhibitory signal. PD-1 also often is upregulated on T cells in the tumor microenvironment, e.g., on tumor-infiltrating T cells, which can occur following signaling through the antigen receptor or certain other activating signals. In some cases, such events may contribute to T-cell exhaustion, which in turn can lead to reduced functionality. Exhaustion of T cells may lead to a progressive loss of T cell functions and/or in depletion of the cells (Yi et al. (2010) Immunology, 129:474-481). T cell exhaustion and/or the lack of T cell persistence can be a barrier to the efficacy and therapeutic outcomes of adoptive cell therapy. Clinical trials have revealed a correlation between greater and/or longer degree of exposure to the antigen receptor (e.g. CAR)-expressing cells and treatment outcomes. WO2016196388 and WO2017193107 describe methods and compositions for reducing PD-1 or PDL-1 expression in T cells by genetically disrupting the PD-1 gene.

Prior to this disclosure, the role of HPK-1 in affecting immune cell functions such as in immunotherapy is largely unknown. In various embodiments, the present inventors unexpected discovered that disrupting, e.g., knocking out, HPK-1 gene of an immune cell (e.g., T cell) can enhance its cytotoxicity and/or improve its persistency with reduced exhaustion, with an efficacy similar or better than disrupting (e.g., knocking out) the PDCD1 gene. For example, as shown in detail herein, knocking out HPK-1 gene in various Car-T cells unexpectedly also reduced expression levels of exhaustion markers, such as PD-1, Lag3, and Tim3. Further, knocking out HPK-1 gene also unexpectedly leads to increased expression levels of cytotoxicity marker CD107a on various Car-T cell surfaces. Knocking out HPK-1 gene also unexpectedly decreased apoptosis of Car-T cells, as evidenced by the reduced level of surface marker Annexin V. These characteristics are useful in adoptive immunotherapy such as for treating cancer. For example, as shown in the examples herein, Car-T cells with HPK-1 gene knockout unexpectedly outperformed wild-type Car-T cells in different animal tumor models, and with efficacy similar or better than the corresponding Car-T cells with PD-1 gene knockout. Moreover, when tested in vivo, Car-T cells with HPK-1 gene knockout are present in a significantly higher plasma level with a longer duration compared to that of wild-type Car-T cells and PD-1 knockout Car-T cells.

Accordingly, in various embodiments, the present invention provides novel cells and cell compositions, including immune cells such as T cells and NK cells, and methods of producing and using the cells and cell compositions. In some embodiments, the cells herein are characterized as having a genetic disruption of a HPK-1 gene encoding a HPK-1 polypeptide and/or containing an agent that induces or is capable of inducing the genetic disruption. In some embodiments, the cells are human cells such as human T cells (e.g., Car-T cells) or NK cells, e.g., derived from a cancer patient. Exemplary sequences for human HPK-1 gene are provided herein (see SEQ ID NOS: 16 and 17; also see NCBI Accession Nos: NM_007181 and NM_001042600). In any of the embodiments herein, the genetic disruption can be a gene knockout. In some embodiments, the genetic disruption can also be a gene knockdown. In some embodiments, the cells with the genetic disruption do not express the endogenous HPK-1 polypeptide; do not contain a contiguous HPK-1 gene, a HPK-1 gene, and/or a functional HPK-1 gene. In any of the embodiments herein, the cells herein can also comprise a recombinant receptor, such as a transgenic or engineered T cell receptor (TCR) and/or a chimeric antigen receptor (CAR), which can be engineered by introducing one or more nucleic acid molecules encoding such recombinant receptors or product thereof. In some embodiments, the recombinant receptors can be engineered TCRs and functional non-TCR antigen receptors, such as chimeric antigen receptors (CARs), including activating, stimulatory, and costimulatory CARs, and combinations thereof. In some embodiments, the recombinant receptor specifically binds to an antigen (e.g., as described herein), and the immune cell is capable of inducing cytotoxicity, proliferating and/or secreting a cytokine upon binding of the recombinant receptor to the antigen. In some embodiments, the cells and compositions herein can be used in adoptive cell therapy, e.g. adoptive immunotherapy.

HPK-1 Genetic Disruption

Various embodiments of the present disclosure are directed to immune cells having a genetic disruption of a HPK-1 gene and/or containing an agent that induces or is capable of inducing the genetic disruption. Although in certain specific embodiments, a HPK-1 gene knockout is preferred, in some embodiments, any genetic disruptions that reduce the expression of a functional HPK-1 gene can also be useful and are contemplated herein.

The genetic disruption herein can comprise a reduction, deletion, elimination, knockout or disruption in expression of HPK-1 in the immune cells (e.g. T cells such as Car-T cells). For example, in some embodiments, the genetic disruption comprises a deletion of a portion of at least one exon (e.g., the first and/or second exon) of HPK-1. In some embodiments, the genetic disruption of HPK-1 gene can be a knock-out, insertion, missense or frameshift mutation, such as a biallelic frameshift mutation, deletion of all or part of the gene, e.g., one or more exon or portion thereof, and/or knock-in.

The genetic disruption herein can be effected by various agents. In some embodiments, the genetic disruption of the HPK-1 gene in the immune cells can be effected by an agent such as an inhibitory nucleic acid molecule, such as an RNA interference (RNAi) agent, short interfering RNA (siRNA), short hairpin (shRNA), micro RNA (miRNA), antisense RNA, and/or ribozymes, which can be used to selectively suppress or repress expression of the gene. siRNA technology includes that based on RNAi utilizing a double-stranded RNA molecule having a sequence homologous with the nucleotide sequence of mRNA which is transcribed from the gene, and a sequence complementary with the nucleotide sequence. siRNA generally is homologous/complementary to one region of mRNA which is transcribed from the gene, or may be siRNA including a plurality of RNA molecules which are homologous/complementary to different regions.

In some embodiments, the genetic disruption can be effected by an agent that includes sequence-specific or targeted nucleases, including DNA-binding targeted nucleases and gene editing nucleases such as zinc finger nucleases (ZFN) and transcription activator-like effector nucleases (TALENs), and RNA-guided nucleases such as a CRISPR-associated nuclease (Cas), specifically designed to be targeted to the sequence of a gene or a portion thereof.

Zinc finger, TALE, and CRISPR system binding domains can be engineered to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073 and US20140120622.

Methods for designing gRNAs for use in a CRISPR system herein include those known in the art, for example, as described in WO 2017/193107, including methods for selecting, designing and validating targeting domains. Exemplary targeting domains are provided herein and can be incorporated into the gRNAs described herein.

Methods for selection and validation of target sequences as well as off-target analyses are described, e.g., in Mali et al., 2013 SCIENCE 339(6121): 823-826; Hsu et al. NAT BIOTECHNOL, 31(9): 827-32; Fu et al., 2014 NAT BIOTECHNOL, doi: 10.1038/nbt.2808. PubMed PMID: 24463574; Heigwer et al., 2014 NAT METHODS 11(2): 122-3. doi: 10.1038/nmeth.2812. PubMed PMID: 24481216; Bae et al., 2014 BIOINFORMATICS PubMed PMID: 24463181; Xiao A et al., 2014 BIOINFORMATICS PubMed PMID: 24389662. Software tools for optimizing choice of gRNA within a user's target sequence are also available and can be used for selecting further suitable gRNA for knocking out or knocking down the HPK-1 gene herein.

In some preferred embodiments, the genetic disruption is a gene knockout. For example, in some embodiments, the HPK-1 gene locus of the immune cells can be edited using an RNA-guided nuclease such as a clustered regularly interspersed short palindromic nucleic acid (CRISPR)-Cas system, such as CRISPR-Cas9 system (e.g., as described herein), specific for the HPK-1 gene. In some embodiments, such gene editing results in an insertion or a deletion at the targeted locus (HPK-1 locus), or a "knockout" of the targeted locus and elimination of the expression of the encoded protein.

Without wishing to be bound by theories, in some embodiments, the HPK-1 gene editing herein (e.g., for knockout) can be carry out with precise genetic modifications by inducing targeted double-stranded breaks or single-stranded breaks, stimulating the cellular DNA-repair mechanisms, including error-prone nonhomologous end joining (NHEJ) and homology-directed repair (HDR). In some embodiments, a donor nucleic acid, e.g., a donor plasmid or nucleic acid encoding a genetically engineered antigen receptor, is provided and is inserted by HDR at the site of gene editing following the introduction of the DSBs. Thus, in some embodiments, the disruption of the gene and the introduction of the antigen receptor, e.g., CAR, can be carried out simultaneously, whereby the gene is disrupted in part by knock-in or insertion of the CAR-encoding nucleic acid. However, in some embodiments, no donor nucleic acid is provided. In some embodiments, NHEJ-mediated repair following introduction of DSBs results in insertion or deletion mutations that can cause gene disruption, e.g., by creating missense mutations and/or frameshifts. In any of the embodiments described herein, the CRISPR/Cas9 system can create a double-stranded break which is repaired by non-homologous end joining to effect insertions and deletions (indels) in the HPK-1 gene.

In some embodiments, other than the HPK-1 gene, substantially no other genes in the immune cells are disrupted. However, in some embodiments, the present disclosure also contemplates further disrupting one or more genes in the immune cells, for example, by introducing an additional agent targeting a gene that encodes PD-1 or PDL-1 polypeptides in the immune cells. Certain agents for disrupting genes encoding PD-1 or PDL-1 polypeptides are known, for example, as described in WO2016/196388 and WO2017/193107.

The HPK-1 genetic disruption efficiency of the immune cells herein can be generally high. For example, in some embodiments, at least about 50%, 60%, 65%, 70%, 75%, 80%, 85%, 90% or 95% of cells in a composition of cells into which an agent (e.g. gRNA/Cas9) for knockout or genetic disruption of a HPK1 gene was introduced contain the genetic disruption; do not express the endogenous HPK-1 polypeptide; do not contain a contiguous HPK-1 gene, a HPK-1 gene, and/or a functional HPK-1 gene. In some embodiments, the immune cells, cell compositions, and methods herein can be characterized by a Cas9-mediated cleavage efficiency (% indel) in or near the HPK-1 gene (e.g. within or about within 100 base pairs, within or about within 50 base pairs, or within or about within 25 base pairs or within or about within 10 base pairs upstream or downstream of the cut site) of at least about 50%, 60%, 65%, 70%, 75%, 80%, 85%, 90% or 95% in cells of a composition of cells into which an agent (e.g. gRNA/Cas9) for knockout or genetic disruption of a HPK-1 gene has been introduced. In preferred embodiments, the immune cells, cell compositions, and methods herein can be characterized by a HPK-1 gene knockout efficiency of at least about 50%, 60%, 65%, 70%, 75%, 80%, 85%, 90% or 95%, e.g., as determined by a method in accordance with the T7E1 assay as described in Example 4 and/or Western Blot method in Example 5.

In some embodiments, the cells with the genetic disruption (e.g., gene knockout) of HPK-1 can be further characterized by the expression level of certain peptides. For example, when compared to a control immune cell that is substantially the same except without the genetic disruption of the HPK-1 gene or without being introduced to any of the agent that induces or is capable of inducing the genetic disruption, the immune cells herein typically can have a reduced level of PD-1, TIM-3, and/or Lag-3; an enhanced level of CD107a; and/or reduced level of Annexin V, e.g., as determined by flow cytometry.

For example, in some embodiments, the cells, cell compositions and methods herein can also be characterized in that the percentage of cells in the cell population expressing PD-1, TIM-3, and/or Lag-3 on cell surface, as determined by flow cytometry, is lower than that in a control cell population; the percentage of cells in the cell population expressing Annexin V on cell surface, as determined by flow cytometry, is lower than that in a control cell population; and/or the percentage of cells in the cell population expressing CD107a on cell surface, as determined by flow cytometry, is higher than that in a control cell population.

As used herein, reference to a "control (immune) cell" or "control (immune) cell population" (also called "corresponding composition" or a "corresponding population of cells", a "reference composition", or a "reference population of cells") refers to the immune cells (e.g., T cells, such as Car-T cells) obtained, isolated, generated, produced and/or incubated under the same or substantially the same conditions, except that the cells such as T cells or population of T cells were not introduced with the agent that induces or is capable of inducing genetic disruption (e.g., gene knockout) of a HPK-1 gene in the immune cells (e.g., Cas9/gRNA). In some embodiments, except for not containing introduction of the agent, such cells or T cells are treated identically or substantially identically as T cells or cells that have been introduced with the agent, such that any one or more conditions that can influence the activity or properties of the cell, including the upregulation or expression of one or more molecules related to immune cell activity and/or exhaustion markers such as PD-1, HPK-1, TIM-3, LAG-3, is not varied or not substantially varied between the cells other than the introduction of the agent. For example, for purposes of assessing reduction in expression and/or inhibition of upregulation of one or more molecules (e.g. PD-1, HPK-1, TIM-3, and LAG-3), T cells containing introduction of the agent and T cells not containing introduction of the agent are incubated under the same conditions known to lead to expression and or upregulation of the one or more molecule in T cells.

Methods and techniques for assessing the expression and/or levels of T cell markers, including molecules such as PD-1, HPK-1, TIM-3, and LAG-3, are known in the art and exemplified herein. Antibodies and reagents for detection of such markers are well known in the art, and readily available. Assays and methods for detecting such markers include, but are not limited to, flow cytometry, including intracellular flow cytometry, ELISA, ELISPOT, cytometric bead array or other multiplex methods, Western Blot and other immunoaffinity-based methods. In some embodiments, assessing surface expression of markers on T cells includes detecting administered antigen receptor (e.g. CAR)-expressing cells in the subject after administration. It is within the level of a skilled artisan to detect antigen receptor (e.g. CAR)-expressing cells in a subject and assess levels of a surface marker. In some embodiments, antigen receptor (e.g. CAR)-expressing cells, such as cells obtained from peripheral blood of a subject, can be detected by flow cytometry or other immunoaffinity based method for expression of a marker unique to such cells, and then such cells can be co-stained for another T cell surface marker or markers. In some embodiments, T cells expressing an antigen receptor (e.g. CAR) can be generated to contain a truncated EGFR (EGFRt) as a non-immunogenic selection epitope, which then can be used as a marker to detect such cells (see e.g. U.S. Pat. No. 8,802,374).

Immune Cells with Recombinant Receptor(s)

The cells herein are typically immune cells (e.g. T cells) to be adoptively transferred (such as cells engineered to express a CAR or transgenic TCR) for treating diseases or disorders such as cancer. In some embodiments, the cells are human cells. In some embodiments, the cells are derived from primary cells from a subject, such as primary immune cells (e.g. T cells) from a subject, which can be ex vivo modified by introducing an agent (e.g., described herein) that is capable of inducing a genetic disruption of HPK-1 herein. In some embodiments, the cells are isolated from a subject, engineered, and administered to the same subject. In some embodiments, they are isolated from one subject, engineered, and administered to another subject. As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

In some embodiments, the immune cells such as T cells are engineered by introducing one or more genetically engineered nucleic acid or product thereof such as genetically engineered antigen receptors, including engineered T cell receptors (TCRs) and functional non-TCR antigen receptors, such as chimeric antigen receptors (CARs), including activating, stimulatory, and costimulatory CARs, and combinations thereof. In some embodiments, the cells also are introduced, either simultaneously or sequentially in any order, with the agent that induces or is capable of reducing, suppressing or disrupting HPK-1 gene in the cells.

As exemplified herein, the genetic disruption such as gene knockout of the HPK-1 gene does not interfere with the functional property of the recombinant receptor (e.g., CAR) or the expression of such recombinant receptor described herein. In some embodiments, compositions herein comprising cells engineered with a recombinant receptor and with a genetic disruption, such as a knockout, of the HPK-1 gene, retain the functional property or activities of the recombinant receptor (e.g. CAR) compared to the recombinant receptor expressed in engineered cells of a corresponding or reference composition in which are engineered with the recombinant receptor but do not comprise the genetic disruption of a HPK-1 gene when assessed under the same conditions. In some embodiments, the recombinant receptor (e.g. CAR) retains specific binding to the antigen. In some embodiments, the recombinant receptor (e.g. CAR) retains activating or stimulating activity, upon antigen binding, to induce cytotoxicity, proliferation, survival or cytokine secretion in cells. In some embodiments, the engineered cells of the provided compositions retain a functional property or activity compared to a corresponding or reference composition comprising engineered cells in which such are engineered with the recombinant receptor but do not comprise the genetic disruption of a HPK-1 gene or express the HPK-1 polypeptide when assessed under the same conditions. In some embodiments, the cells retain (or with enhanced) cytotoxicity, proliferation, survival or cytokine secretion compared to such a corresponding or reference composition.

In some embodiments, the HPK-1 gene disrupted cells in the composition retain a phenotype of the immune cell or cells compared to the phenotype of cells in a corresponding or reference composition when assessed under the same conditions. In some embodiments, cells in the composition include naive cells, effector memory cells, central memory cells, stem central memory cells, effector memory cells, and long-lived effector memory cells. In some embodiments, the percentage of T cells, or T cells expressing the recombinant receptor (e.g. CAR), and comprising the genetic disruption of a HPK-1 gene exhibit a non-activated, long-lived memory or central memory phenotype that is the same or substantially the same as a corresponding or reference population or composition of cells engineered with the recombinant receptor but not containing the genetic disruption or expressing the HPK-1 polypeptide. In some embodiments, the composition of the present disclosure comprises T cells comprising the recombinant receptor (e.g. CAR) and one or more phenotypic markers selected from CCR7+, 4-1BB+ (CD137+), TIM3+, CD27+, CD62L+, CD127+, CD45RA+, CD45RO−, t-betlow, IL-7Ra+, CD95+, IL-2Rp+, CXCR3+ or LFA-1+.

Methods for measuring such property, activity or phenotype are known in the art, for example, they can be measured in an in vitro assay, such as by incubation of the cells at or about 37° C.+2° C. for up to or up to about 12, 24, 36, 48 or 60 hours, for example, in the presence of the antigen and/or one or more cytokines (e.g. IL-2, IL-15 and/or IL-17). In some embodiments, any of the assessed activities, properties or phenotypes can be assessed at various days following electroporation or other introduction of the agent, such as after or up to 3, 4, 5, 6, 7 days. In some embodiments, such activity, property or phenotype is retained by at least 80%, 85%, 90%, 95% or 100% of the cells in the composition compared to that of a corresponding composition containing cells engineered with the recombinant receptor but not comprising the genetic disruption of a HPK-1 gene when assessed under the same conditions.

Cells

Various cells can be used for the compositions and methods of the present disclosure. In some embodiments, the cells, e.g., engineered cells, are eukaryotic cells, such as mammalian cells, e.g., human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some embodiments, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and reintroducing them into the same patient, before or after cryopreservation.

Among the sub-types and subpopulations of T cells and/or of CD4+ and/or of CD8+ T cells are naive T ($T_N$) cells, effector T cells ($T_{EF}$F), memory T cells and sub-types thereof, such as stem cell memory T (TSCMX central memory T (TCM), effector memory T (TEM), or terminally differentiated effector memory T cells, tumor-infiltrating lymphocytes (TIL), immature T cells, mature T cells, helper T cells, cytotoxic T cells, NK T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for (marker$^{+1"}$) or express high levels (marker$^{high}$) of one or more particular markers, such as surface markers, or that are negative for (marker") or express relatively low levels (marker$^{low}$) of one or more markers. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8$^+$ cells or the T cells, e.g., CD3$^+$ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD 127). In some examples, CD8+ T cells are enriched for cells positive for CD45RO (or negative for CD45RA) and for CD62L.

In some embodiments, the cells can be a CD4+ T cell population or a CD8+ T cell sub-population, e.g., a sub-population enriched for central memory ($T_{CM}$) cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

Recombinant Receptors

For adoptive immunotherapy, the cells herein typically contain recombinant receptors. For example, in some embodiments, the cells can comprise one or more nucleic acids introduced via genetic engineering, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol, 2012 October; 24(5): 633-39; Wu et al., Cancer, 2012 Mar. 18(2): 160-75. In some embodiments, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013);

Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors (e.g., CAR) in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD276, CD44, EGFR, EGP-2, EGP-4, EPHa2, ErbB2, 3, or 4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the recombinant receptor, e.g., CAR, specifically binds to one or more antigens independently selected from ROR1, Her2, L1-CAM, CD19, CD20, CD22, CEA, hepatitis B surface antigen, anti-folate receptor, CD23, CD24, CD30, CD33, CD38, CD276, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule (CD171), MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), cyclin A1 (CCNA1), BCMA and interleukin 12. In some embodiments, the recombinant receptor (e.g., CAR) specifically binds to CD19, BCMA, Integrin αVβ6, MUC1, EGFRvIII, HER2, EGFR, GD2, and/or Mesothelin. In some embodiments, the recombinant receptor (e.g., CAR) binds a pathogen-specific antigen. In some embodiments, the recombinant receptor (e.g., CAR) is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some embodiments, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain.

This antigen recognition domain generally is linked to one or more intracellular signaling components, such as signaling components that mimic activation through an antigen receptor complex, such as a TCR complex, and optionally associated costimulatory signals, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some embodiments is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD16, CD22, CD33, CD37, CD64, CD80, CD86, CD134, CD137, CD154. Alternatively, the transmembrane domain in some embodiments is synthetic. In some embodiments, the synthetic transmembrane domain comprises predominantly hydrophobic residues such as leucine and valine. In some embodiments, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor (e.g., CD3 signal), a signal through such a receptor in combination with a costimulatory receptor (e.g., CD3/CD28 signal), and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some embodiments, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some embodiments, the CAR or other chimeric receptor includes a chimeric molecule between CD3-zeta or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some embodiments also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some embodiments, an additional CAR is expressed in the same cell and provides the component for generating the secondary or costimulatory signal.

T cell activation is in some embodiments described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some embodiments, the CAR includes one or both of such signaling components.

In some embodiments, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD5, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some embodiments, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some embodiments, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD 137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

CARs can be referred to as first, second, and/or third generation CARs. In some embodiments, a first generation CAR is one that solely provides a CD3-chain induced signal upon antigen binding; in some embodiments, a second-generation CARs is one that provides such a signal and costimulatory signal, such as one including an intracellular signaling domain from a costimulatory receptor such as CD28 or CD137; in some embodiments, a third generation CAR is one that includes multiple costimulatory domains of different costimulatory receptors.

In some embodiments, the chimeric antigen receptor includes an extracellular portion containing an antibody or antibody fragment. In some embodiments, the chimeric antigen receptor includes an extracellular portion containing the antibody or fragment and an intracellular signaling domain. In some embodiments, the antibody or fragment includes an scFv and the intracellular domain contains an ITAM. In some embodiments, the intracellular signaling domain includes a signaling domain of a zeta chain of a CD3-zeta chain. In some embodiments, the chimeric antigen receptor includes a transmembrane domain linking the extracellular domain and the intracellular signaling domain. In some embodiments, the transmembrane domain contains a transmembrane portion of CD28. In some embodiments, the chimeric antigen receptor contains an intracellular domain of a T cell costimulatory molecule. In some embodiments, the T cell costimulatory molecule is CD28 or 4-1BB.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some embodiments, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) Immunol. 175:5799-5808. In some embodiments, phage display is used to isolate TCRs against a target antigen (see, e.g., Varela-Rohena et al. (2008) Nat Med. 14: 1390-1395 and Li (2005) Nat Biotechnol. 23:349-354).

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are co-expressed. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13: 1050-1063; Frecha et al. (2010) Molecular Therapy: The Journal of the American Society of Gene Therapy. 18: 1748-1757; and Hackett et al. (2010) Molecular Therapy: The Journal of the American Society of Gene Therapy. 18:674-683).

CRISPR/Cas9 System

Various CRISPR/Cas9 system can be used to induce the genetic disruption such as a gene knockout of HPK-1 gene in the immune cells herein. Typically, the immune cells are introduced an agent comprising a Cas9 molecule and a gRNA having a targeting domain that is complementary with, binds to, recognizes, or hybridizes a target domain of the HPK-1 gene (e.g., in the first or second exon) or one or more polynucleotides encoding the Cas9 and gRNA. In some embodiments, the agent introduced into the immune cell is or comprises a ribonucleoprotein (RNP) complex of Cas9 and gRNA containing the HPK-1-targeted targeting domain (Cas9/gRNA RNP). In some embodiment, the introduction includes contacting the agent or portion thereof with the immune cells, in vitro, which can include cultivating or incubating the cells and agent for up to 24, 36 or 48 hours or 3, 4, 5, 6, 7, or 8 days or more. In various embodiments, the Cas9 and gRNA or the encoding polynucleotides can be directly introduced into cells, for example by electroporation.

In some embodiments, prior to, during or subsequent to contacting the agent with the cells and/or prior to, during or subsequent to effecting delivery (e.g. electroporation), the cells can be incubated in the presence of a cytokine, a stimulating agent and/or an agent that is capable of inducing proliferation of the immune cells (e.g. T cells). In some embodiments, at least a portion of the incubation is in the presence of a stimulating agent that is or comprises an antibody specific for CD3 an antibody specific for CD28 and/or a cytokine. In some embodiments, at least a portion of the incubation is in the presence of a cytokine, such as one IL-2, IL-7 and IL-15. In some embodiments, the incubation is for up to 8 days hours before or after the electroporation, such as up to 24 hours, 36 hours or 48 hours or 3, 4, 5, 6, 7 or 8 days or more. In some embodiments, the incubation in the presence of a stimulating agent (e.g. anti-CD3/anti-CD28) and/or a cytokine (e.g. IL-2, IL-7 and/or IL-15) is for up to 24 hours, 25 hours or 48 hours prior to the electroporation.

gRNA

In some embodiments, the agent introduced into the cells comprises a gRNA that targets a region of the HPK-1 locus, or a nucleic acid encoding the gRNA. In some embodiments, the gRNA molecule can be unimolecular (having a single RNA molecule), sometimes referred to herein as "chimeric" gRNAs, or modular (comprising more than one, and typically two, separate RNA molecules).

In some embodiments, the gRNA is a chimeric gRNA comprising, from 5' to 3': a targeting domain which is complementary to a target nucleic acid, such as a sequence from the HPK-1 gene (exemplary sequence are provided in SEQ ID NOS: 16 and 17; also see NCBI Accession Nos: NM_007181 and NM_001042600)), a first complementarity domain; a linking domain; a second complementarity domain (which is complementary to the first complementarity domain); a proximal domain; and optionally, a tail domain.

In some embodiments, the gRNA is a modular gRNA comprising first and second strands. In these cases, the first strand preferably includes, from 5' to 3': a targeting domain (which is complementary to a target nucleic acid, such as a sequence from HPK-1 gene (exemplary sequence are provided in SEQ ID NOS: 16 and 17; also see NCBI Accession Nos: NM_007181 and NM_001042600)) and a first complementarity domain. The second strand generally includes, from 5' to 3': optionally, a 5' extension domain; a second complementarity domain; a proximal domain; and optionally, a tail domain.

The targeting domain of the gRNA can comprise a nucleotide sequence that is complementary, e.g., at least 80, 85, 90, 95, 98 or 99% complementary, e.g., fully complementary, to the target sequence on the target nucleic acid (e.g., HPK-1 gene, such as the first or second exon). The strand of the target nucleic acid comprising the target sequence is referred to herein as the "complementary strand" of the target nucleic acid. Guidance on the selection of targeting domains can be found, e.g., in Fu Y et al., Nat Biotechnol 2014 (doi:10.1038/nbt.2808) and Sternberg S H et al, Nature 2014 (doi: 10.1038/nature13011).

The targeting domain is part of an RNA molecule and will therefore comprise the base uracil (U), while any DNA encoding the gRNA molecule will comprise the base thymine (T). While not wishing to be bound by theory, in an embodiment, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence. In an embodiment, the targeting domain is 5 to 50 nucleotides in length. The strand of the target nucleic acid with which the targeting domain is complementary is referred to herein as the complementary strand. Some or all of the nucleotides of the domain can have a modification, e.g., to render it less susceptible to degradation, improve bio-compatibility, etc. By way of non-limiting example, the backbone of the targeting domain can be modified with a phosphorothioate, or other modification(s). In some cases, a nucleotide of the targeting domain can comprise a 2' modification, e.g., a 2-acetylation, e.g., a 2' methylation, or other modification(s).

In various embodiments, the targeting domain of the gRNA herein is 16-26 nucleotides in length (i.e. it is 16 nucleotides in length, or 17 nucleotides in length, or 18, 19, 20, 21, 22, 23, 24, 25 or 26 nucleotides in length).

In some embodiments, the target sequence (target nucleic acid) is at or near the HPK-1 locus, such as any part of the HPK-1 coding sequence in SEQ ID NOS: 16 and 17. In some embodiments, the target nucleic acid complementary to the targeting domain is located at an early coding region of a gene of interest, herein HPK-1 gene. Targeting of the early coding region can be used to knockout (i.e., eliminate expression of) the gene of interest such as HPK-1 gene. In some embodiments, the early coding region of a gene of interest (e.g., HPK-1 gene) includes sequence immediately following a start codon (e.g., ATG), or within 500 bp of the start codon (e.g., less than 500 bp, 450 bp, 400 bp, 350 bp, 300 bp, 250 bp, 200 bp, 150 bp, 100 bp, 50 bp, 40 bp, 30 bp, 20 bp, or 10 bp). In particular examples, the target nucleic acid is within 200 bp, 150 bp, 100 bp, 50 bp, 40 bp, 30 bp, 20 bp or 10 bp of the start codon. In some examples, the target nucleic acid is located in the first or second exon of the HPK-1 gene. In some examples, the targeting domain of the gRNA is complementary, e.g., at least 80, 85, 90, 95, 98 or 99% complementary, e.g., fully complementary, to the target sequence on the target nucleic acid, such as the target nucleic acid in the HPK-1 locus.

In some embodiments, the target domain for knockout or knockdown of HPK-1 is or comprises a sequence selected from any of SEQ ID NOS: 1 and 11-15.

| Target Domain Sequence | Location on human HPK-1 gene |
|---|---|
| SEQ ID NO: 1: GACCTGGTGGCACTGAAGA | Second exon |
| SEQ ID NO: 11 GCTCGAGACAAGGTGTCAG | Second exon |
| SEQ ID NO: 12 AAGGTGTCAGGGGACCTGG | Second exon |
| SEQ ID NO: 13 ACCACTATGACCTGCTACAG | First exon |
| SEQ ID NO: 14 GACCTGCTACAGCGGCTGGG | First exon |
| SEQ ID NO: 15 GCTGGGTGGCGGCACGTATG | First exon |

In some embodiments, the targeting domain of the gRNA is the same or differs no more than 1, 2, or 3 nucleotides from a sequence fully complementary to a target sequence selected from SEQ ID NOS: 1 and 11-15.

Cas9

In some embodiments, the agent can comprise a Cas9 molecule or a nucleic acid encoding the Cas9. In some embodiments, the agent can comprise a Cas9/gRNA molecular complex (e.g., formed by any of the gRNA herein with any of the Cas9 herein), or one or more nucleic acid molecules encoding the Cas9 and gRNA. For example, in some embodiments, the Cas9 protein and gRNA can be separated and incubated, e.g., in a ratio of about 10:1 to about 1:10 (Cas9 to gRNA, by mass) to form a gRNA/Cas9 complex, which can then be delivered into the immune cells, such as by electroporation. Typically, the amount of gRNA/Cas9 complex used for the genetic disruption can be about 1-100 ug/1×10$^6$ cells.

As understood by those skilled in the art, a Cas9 molecule or Cas9 polypeptide, is a polypeptide that can interact with a guide RNA (gRNA) molecule and, in concert with the gRNA molecule, localizes to a site which comprises a target domain and a PAM sequence (e.g., in the case of *S. pyogenes*, a NGG PAM, in the case of *S. aureus*, NNGRR (e.g, a NNGRRT or NNGRRV) PAM, and in the case of *N. meningtidis*, a NNNNGATT or NNNNGCTT PAM).

Cas9 molecules of a variety of species can be used in the methods and compositions described herein. In some embodiments, the Cas9 molecule is a *S. pyogenes*, *S. aureus*, or *N. meningitidis*, Cas9. Non-limiting useful Cas9 molecules include those derived from species including *S. pyogenes, S. aureus, N. meningitidis, S. thermophiles, Acidovo ax avenae, Actinobacillus pleuropneumonias, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Coxynebacterium accolens, Coxynebacterium diphtheria, Coxynebacterium matruchotii, Dinoxoseobacter shibae, Eubacterium dolichum, Gammaproteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichospoxium, Mobiluncus mulieris, Neisseria bacilliformis, Neisseria cinerea, Neisseria flavescens, Neisseria lactamica, Neisseria meningitidis, Neisseria* sp., *Neisseria wadswoxthii, Nitrosomonas* sp., *Parvibaculum lavamentivoxans, Pasteurella multocida, Phascolarctobacterium succinatutens, Ralstonia syzygii, Rhodopseudomonas palustris, Rhodovulum* sp., *Simonsiella muelleri, Sphingomonas* sp., *Spoxolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae*.

In some embodiments, the Cas9 molecules used for the methods herein are wild type Cas9 molecules. Typically, wild type Cas9 molecules cleave both strands of a target nucleic acid molecule. In some embodiments, modified Cas9 molecules and Cas9 polypeptides with altered nuclease cleavage properties (or other properties) can also be used, e.g., a nickase, or which lacks the ability to cleave target nucleic acid. For mammalian expression, in some embodiments, bacterial Cas9 cDNA can be codon optimized, for example, into a humanized Cas9 cDNA.

Exemplary naturally occurring Cas9 molecules are described in Chylinski et al., RNA Biology 2013 10:5, 727-737. Such Cas9 molecules include Cas9 molecules of a cluster 1-78 bacterial family Exemplary naturally occurring Cas9 molecules include a Cas9 molecule of a cluster 1 bacterial family Examples include a Cas9 molecule of: *S. pyogenes* (e.g., strain SF370, MGAS 10270, MGAS 10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip1 1262), *Enterococcus italicus* (e.g., strain DSM 15952), or *Enterococcus faecium* (e.g., strain 1,231,408). Another exemplary Cas9 molecule is a Cas9 molecule of *Neisseria meningitidis* (Hou et al., PNAS Early Edition 2013, 1-6).

In some embodiments, suitable Cas9 molecule can be modified by incorporating one or more human sequences such as nuclear localization sequences (e.g., inserted at one or both the C- and N-termini of the Cas9 molecule) that can facilitate the entry of the Cas9 molecule into the nucleus of human immune cells. A nuclear localization signal or sequence (NLS) is an amino acid sequence that 'tags' a protein for import into the cell nucleus by nuclear transport. Typically, this signal consists of one or more short sequences of positively charged lysines or arginines exposed on the protein surface. Different nuclear localized proteins may share the same NLS. The Cas9 nucleus activity is typically maintained by introduction of such NLS's, such that it can create a double-stranded break for NHEJ or HDR repair. In some embodiments, to facilitate expression in mammalian cells such as human cells, typically, codon-optimized Cas9 cDNA can be used. Examples of such "humanized Cas9" are known, for example, as described in Chang, N. et al., *Cell Research* 23:465-472 (2013), the content of which is incorporated by reference in its entirety, including the Sequence of the humanized, codon-optimized Cas9 cDNA and the protein sequence reported therein. Other NLS's can also be suitable for facilitating entry of Cas9 into cell nucleus and have been reported, for example, as in U.S. Pat. No. 8,795,965.

Nucleic Acids, Vectors, and Delivery

Typically, the genetic disruption of HPK-1 gene herein can be effected by introducing the agent that induces or is capable of inducing the HPK-1 genetic disruption into the immune cells, which can be followed by incubation, cultivating, expanding, and/or selecting the cells that contain the genetic disruption (e.g., gene knockout).

The agent for disrupting HPK-1 gene can be delivered into the immune cells through different methods known by those skilled in the art. In some embodiments, the agent can comprise one or more molecule(s) which is, comprises, or encodes an antisense molecule, siRNA, shRNA, miRNA, a gene editing nuclease, zinc finger nuclease protein (ZFN), a TAL-effector nuclease (TALEN) or a CRISPR-Cas9 combination that specifically binds to, recognizes, or hybridizes to the HPK-1 gene. Such agents can in some embodiments be delivered into the immune cells directly, e.g., by electroporation, liposomes or nanoparticles, etc.

In some embodiments, nucleic acid molecules encoding the one or more molecules can be delivered into the immune cells. In some embodiments, such nucleic acid molecules or complex thereof can be introduced into cells, such as T cells, by methods well known in the art. Such methods include, but are not limited to, introduction in the form of recombinant viral vectors (e.g. retroviruses, lentiviruses, adenoviruses), liposomes or nanoparticles. In some embodiments, methods can include microinjection, electroporation, particle bombardment, Calcium Phosphate transfection, cell compression, squeezing. In some embodiments, the polynucleotides may be included in vectors, more particularly plasmids or virus, in view of being expressed in the cells. In some embodiments, the vector can be a plasmid or viral vector, such as a retroviral vector, gammaretroviral vector, herpesvirus vector, lentiviral vector, adenoviral vector or adeno-associated vector, which can be introduced into a target cell (e.g., the immune cells herein or cells for producing the gRNA for introducing into the immune cells) by well-known methods and expressed.

The gRNA/Cas9 system herein can be introduced into the target cells in various methods, typically in vitro or ex vivo. For example, in some embodiments, DNA encoding Cas9 molecules and/or gRNA molecules, can be delivered into cells by art-known methods, e.g., by vectors (e.g., viral or non-viral vectors), non-vector based methods (e.g., using naked DNA or DNA complexes), or a combination thereof.

In some embodiments, the Cas9- and/or gRNA-encoding DNA can be delivered by a vector (e.g., viral vector/virus or plasmid). The vector can comprise a sequence that encodes a Cas9 molecule and/or a gRNA molecule. In some embodiments, the vector can further includes a regulatory/control element, such as a promoter, for example, a U6 or T7 promoter. In some embodiments, the vector (e.g., a plasmid vector) comprises a sequence encoding the gRNA molecule herein, e.g., a gRNA comprising a targeting domain that is complementary (e.g., at least 80, 85, 90, 95, 98 or 99% complementary or fully complementary) with a target domain of the HPK-1 gene (e.g., at least one exon of the HPK-1 gene, such as the first or second exon, e.g., SEQ ID NOS: 1 and 11-15). In some embodiments, the vector (e.g., a plasmid vector) comprises a sequence encoding a gRNA comprising a targeting domain that is the same, or differs no more than 1, 2, or 3 nucleotides, from a sequence fully complementary to a target sequence selected from SEQ ID NOS: 1 and 11-15. In some embodiments, the vector is a plasmid vector comprising sequences as set forth in SEQ ID NOS: 3 and 4. In some embodiments, the plasmid vector is a pUC57kan-T7-gRNA.

In some embodiments, the vector or delivery vehicle is a viral vector (e.g., for generation of recombinant viruses). In some embodiments, the virus is a DNA virus (e.g., dsDNA or ssDNA virus). In some embodiments, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses. In some embodiments, the viral vector can be replication competent. In some embodiments, the viral vector can be replication defective.

In some embodiments, the gRNA and Cas9 protein can be prepared and isolated and then introduced into a target cell, e.g., through electroporation. For example, in some embodiments, the nucleic acid molecule and/or vector herein encoding the gRNA can be used for preparing the gRNA. The gRNA can then be isolated and/or purified for delivering into the immune cells herein. The gRNA can be delivered into the immune cells along with a Cas9 protein, for example, as a gRNA/Cas9 complex. In some embodiments, the gRNA can be delivered into the immune cells separately from the Cas9 protein, which can be introduced into the cells either as a separate protein or a nucleic acid/vector encoding the Cas9 protein.

In some embodiments, the agent introduced into the immune cell is or comprises a ribonucleoprotein (RNP) complex of Cas9 and gRNA containing the HPK-1-targeted targeting domain (Cas9/gRNA RNP). In some embodiment, the introduction includes contacting the agent or portion thereof with the immune cells, in vitro, which can include cultivating or incubating the cells and agent for up to 24, 36 or 48 hours or 3, 4, 5, 6, 7, or 8 days or more. In various embodiments, the Cas9 and gRNA or the encoding polynucleotides can be directly introduced into cells, for example by electroporation.

In some embodiments, prior to, during or subsequent to contacting the agent with the cells and/or prior to, during or subsequent to effecting delivery (e.g. electroporation), the cells can be incubated in the presence of a cytokine, a stimulating agent and/or an agent that is capable of inducing proliferation of the immune cells (e.g. T cells). In some embodiments, at least a portion of the incubation is in the presence of a stimulating agent that is or comprises an antibody specific for CD3 an antibody specific for CD28 and/or a cytokine. In some embodiments, at least a portion of the incubation is in the presence of a cytokine, such as one IL-2, IL-7 and IL-15. In some embodiments, the incubation is for up to 8 days hours before or after the electroporation, such as up to 24 hours, 36 hours or 48 hours or 3, 4, 5, 6, 7 or 8 days or more. In some embodiments, the incubation in the presence of a stimulating agent (e.g. anti-CD3/anti-CD28) and/or a cytokine (e.g. IL-2, IL-7 and/or IL-15) is for up to 24 hours, 25 hours or 48 hours prior to the electroporation.

Other methods of delivering the agent such as the gRNA and Cas9 protein include those known in the art.

In some embodiments, the immune cells herein further comprises a recombinant receptor, and the introduction of the agent (e.g., gRNA/Cas9 complex) can occur simultaneously or sequentially with the introduction of the nucleic acid encoding the recombinant receptor, such as a CAR as described herein, or product thereof.

In some embodiments, the degree of knockout of a gene (e.g., HPK-1), alternatively referred to as knockout efficiency, at various time points, e.g., 24 to 72 hours after introduction of agent, can be assessed using any of a number of well-known assays for assessing genetic disruption in cells, for example, the method described in the Examples section herein. Degree of knockdown of a gene at various time points, e.g., 24 to 72 hours after introduction of agent, can be assessed using any of a number of well-known assays for assessing gene expression in cells, such as assays to determine the level of transcription or protein expression or cell surface expression.

T Cells Compositions and Methods

Certain specific embodiments are directed to T cells, more specifically, T cells having a CAR (e.g., as described herein). In some embodiments, the T cells have a genetic disruption (e.g., gene knockout) of HPK-1 gene. In some embodiments, the T cells contain (a) any one or more of the gRNA herein, or a polynucleotide or vector encoding the gRNA, (b) any one or more of the Cas9 proteins herein, or a polynucleotide or vector encoding the Cas9 protein, or a combination of (a) and (b). In some embodiments, the T cells contain a gRNA/Cas9 complex herein.

In some embodiments, a T cell composition can comprise a T cell and a means for knocking out the HPK-1 gene in the T cell. In some embodiments, the T cell is a primary cell from a human cancer patient. In some embodiments, the human patient suffers from a cancer selected from the group consisting of: lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, medulloblastoma, and combinations thereof. In some embodiments, the means for knocking out the HPK-1 gene is a gRNA/Cas9 complex, wherein the gRNA comprises a targeting sequence that is the same or differs no more than 1, 2, or 3 nucleotides from a sequence fully complementary to a target sequence selected from SEQ ID NOs: 1 and 11-15. In some embodiments, the means for knocking out the HPK-1 gene is a gRNA/Cas9 complex as shown in the Examples section herein. In some embodiments, the T cell further comprises a recombinant receptor, such as a CAR as described herein.

In some specific embodiments, the present disclosure provides a T cell population (e.g., a Car-T cell population) characterized in that at least about 50%, 75%, 80%, 85%, or 90% of the cells comprise a recombinant receptor (e.g., a chimeric antigen receptor, e.g., as described herein) on cell surface; and a HPK-1 gene knockout efficiency of at least about 50%, 60%, 65%, 70%, 75%, 80%, 85%, 90% or 95%, e.g., as determined by a method in accordance with the T7E1 assay as described in Example 4 and/or Western Blot method in Example 5. In some embodiments, the T cell population (e.g., Car-T cell population) can be characterized in that the percentage of cells in the cell population expressing PD-1, TIM-3, and/or Lag-3 on cell surface, as determined by flow cytometry, is lower than that in a control cell population; the percentage of cells in the cell population expressing Annexin V on cell surface, as determined by flow cytometry, is lower than that in a control cell population; and/or the percentage of cells in the cell population expressing CD107a on cell surface, as determined by flow cytometry, is higher than that in a control cell population. The T cell population with these characteristics can be prepared by those skilled in the art in view of the present disclosure. As will be understood by those skilled in the art, the term "T cell population" or "Car-T cell population" and similar terms herein does not mean that the cell population does not contain any other types of cells, although preferably, such population should contain as a majority (e.g., at least about 50%) T cells or Car-T cells, respectively. It's well-known that the two marketed Car-T therapy, Kymriah (tisagenlecleucel) or Yescarta (axicabtagene ciloleucel), in addition to Car-T cells, can also contain NK cells, NK-T cells, B cells etc.

In some specific embodiments, the present disclosure provides a method of altering a T cell comprising contacting the T cell with an agent that induces or is capable of inducing a genetic disruption (e.g., gene knockout) of a HPK1 gene. In some embodiments, the method comprises (a) obtaining a T cell from a human patient (e.g., as described herein); (b) introducing the agent that induces or is capable of inducing HPK-1 genetic disruption in the T cell; and (c) incubating and optionally expanding the T cell with the agent to provide a HPK-1 gene disrupted T cell population. In some embodiments, the incubation can be conducted in the presence of a cytokine such as IL-2 or an anti-CD3 and/or anti-CD28 antibody. In some embodiments, the method further comprises (d) introducing in the T cell a nucleic acid encoding a recombinant receptor, such as a CAR as described herein, or product thereof. Suitable agents include any of those described herein. In some embodiments, the method comprises introducing into the T cell (a) any one or more of the gRNA herein, or a polynucleotide or vector encoding the gRNA, (b) any one or more of the Cas9 proteins herein, or a polynucleotide or vector encoding the Cas9 protein, or a combination of (a) and (b). In some embodiments, the method comprises introducing into the T cell a gRNA/Cas9 complex. In some embodiments, the HPK-1 gene disrupted T cell population produced by the methods herein can be characterized by any of the characteristics such as the HPK-1 gene knockout efficiency, the expression of exhaustion markers, PD-1, TIM-3, and/or Lag-3, expression of apoptosis marker Annexin V, expression of cytotoxicity marker CD107a, as described herein. For example, in some embodiments, the HPK-1 gene knockout efficiency can be at least about 50%, 60%, 65%, 70%, 75%, 80%, 85%, 90% or 95%, e.g., as determined by a method in accordance with the T7E1 assay as described in Example 4 and/or Western Blot method in Example 5.

The T cell or T cell population can include cells that have been obtained from a subject (e.g., a human subject, e.g., having cancer), such as primary cells, cells obtained from a peripheral blood mononuclear cells (PBMC) sample, an unfractionated T cell sample, a lymphocyte sample, a white blood cell sample, an apheresis product, or a leukapheresis product. In some embodiments, T cells can be separated or selected to enrich T cells in the population using positive or negative selection and enrichment methods. In some embodiments, the population contains CD4+, CD8+ or CD4+ and CD8+ T cells. Other suitable types of T cells include any of those described herein. In some embodiments, the T cell is a primary cell from a human cancer patient. In some embodiments, the human patient suffers from a cancer selected from the group consisting of: lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, medulloblastoma, and combinations thereof.

In some embodiments, the introducing into the cells in the T cell population of nucleic acid encoding a recombinant receptor (e.g., genetically engineered antigen receptor) and the agent for disrupting the HPK-1 gene (e.g. Cas9/gRNA RNP herein) can occur simultaneously or sequentially in any order. In some embodiments, subsequent to the introduction of the recombinant receptor (e.g. CAR) and the agent (e.g. Cas9/gRNA RNP herein), the cells are cultured or incubated under conditions to stimulate expansion and/or proliferation of cells, e.g., as described herein.

In some embodiments, the present disclosure also provides methods for enhancing immune cell, such as T cell, function in adoptive cell therapy, including those offering improved efficacy, such as by increasing activity and potency of administered genetically engineered (e.g. CAR+) cells, while maintaining persistence or exposure to the transferred cells over time. In some embodiments, the method comprises disrupting the HPK-1 gene in the immune cells, e.g., by introducing into the immune cells an agent that induces or is capable of inducing a genetic disruption (e.g., gene knockout) of a HPK-1 gene. In some embodiments, the method comprises introducing into the immune cells (a) any one or more of the gRNA herein, or a polynucleotide or vector encoding the gRNA, (b) any one or more of the Cas9 proteins herein, or a polynucleotide or vector encoding the Cas9 protein, or a combination of (a) and (b). In some embodiments, the method comprises introducing into the immune cells a gRNA/Cas9 complex herein. In some embodiments, the immune cells with a disrupted HPK-1 gene, such as CAR-expressing T cells, exhibit increased expansion and/or persistence when administered in vivo to a subject, as compared to certain available methods.

In some embodiments, the present disclosure also provides methods for enhancing cytotoxicity, inhibiting exhaustion, and/or enhancing infiltration in spleen and/or tumors, of an immune cell population (e.g., T cell population such as Car-T cell), the method comprising contacting the immune cell population with an agent that induces or is capable of inducing a genetic disruption (e.g., gene knockout) of a HPK1 gene. In some embodiments, the method comprises (a) obtaining an immune cell (e.g., T cell) population from a human patient (e.g., as described herein); (b) introducing the agent that induces or is capable of inducing HPK-1 genetic disruption in the immune cell (e.g., T cell) population; and (c) incubating and optionally expanding the immune cell (e.g., T cell) with the agent to provide a HPK-1 gene disrupted immune cell (e.g., T cell) population that has enhanced cytotoxicity, reduced exhaustion, and/or enhanced infiltration in spleen and/or tumors compared to the cell population prior to introducing the agent. In some embodiments, the method further comprises introducing in the immune cell (e.g., T cell) a nucleic acid encoding a recombinant receptor, such as a CAR as described herein, or product thereof. Suitable agents include any of those described herein. In some embodiments, the method comprises introducing into the immune cell (e.g., T cell) (a) any one or more of the gRNA herein, or a polynucleotide or vector encoding the gRNA, (b) any one or more of the Cas9 proteins herein, or a polynucleotide or vector encoding the Cas9 protein, or a combination of (a) and (b). In some embodiments, the method comprises introducing into the immune cells a gRNA/Cas9 complex herein. In some embodiments, the HPK-1 gene disrupted T cell population produced by the methods herein can be characterized by any of the characteristics such as the HPK-1 gene knockout efficiency, the expression of exhaustion markers, PD-1, TIM-3, and/or Lag-3, expression of apoptosis marker Annexin V, expression of cytotoxicity marker CD107a, as described herein. For example, in some embodiments, the HPK-1 gene knockout efficiency can be at least about 50%, 60%, 65%, 70%, 75%, 80%, 85%, 90% or 95%, e.g., as determined by a method in accordance with the T7E1 assay as described in Example 4 and/or Western Blot method in Example 5.

In some embodiments, the immune cell population is a Car-T cell population. In some embodiments, the Car-T population is characterized in that at least about 50%, 60%, 65%, 70%, 75%, 80%, 85%, 90% or 95% of the cells comprise a recombinant receptor (e.g., a chimeric antigen receptor, e.g., as described herein) on cell surface. In some embodiments, the method produces a Car-T cell population with a HPK-1 gene knockout efficiency of at least about 50%, 60%, 65%, 70%, 75%, 80%, 85%, 90% or 95%, e.g., as determined by a method in accordance with the T7E1 assay as described in Example 4 and/or Western Blot method in Example 5.

As detailed herein, it is unexpected that by disrupting the HPK-1 gene in immune cells, such as Car-T cells, the immune cells exhibit enhanced cytotoxicity, increased persistence and reduced exhaustion, and/or enhanced infiltration in spleen and/or tumors. Such effects have also been observed in vivo when administered to a subject. For example, in one animal study, the HPK-1 knockout Car-T cells were found to remain in the plasma of the treated animals at much higher level when compared to either wild type Car-T cells or a PD-1 knockout Car-T cells. The degree or extent of persistence of administered cells can be detected or quantified after administration to a subject such as by qPCR, flow cytometric assays, or cell-based assays. This further illustrates the advantages associated with the compositions and methods herein, for example, in adoptive immunotherapy.

As would be understood by those skilled in the art in view of this disclosure, the methods herein are not limited to any particular immune cells or particular CARs. In some embodiments, commercially available Car-T cells can also be modified using the methods herein, for example, to knockout the HPK-1 gene to further improve its immunotherapy function such as to reduce T cell exhaustion. For example, Car-T cells for Kymriah (tisagenlecleucel) or Yescarta (axicabtagene ciloleucel) can be modified by the methods herein to knockout the HPK-1 gene. As discussed herein, in such embodiments, introducing agents for genetic modification of HPK-1 gene can occur simultaneously or sequentially in any order with introducing nucleic acids encoding the CD19 CAR for Kymriah or Yescarta.

For example, according to the package insert, to prepare YESCARTA, a patient's own T cells are harvested and genetically modified ex vivo by retroviral transduction to express a chimeric antigen receptor (CAR) comprising a murine anti-CD19 single chain variable fragment (scFv) linked to CD28 and CD3-zeta co-stimulatory domains. The anti-CD19 CAR T cells are expanded and infused back into the patient, where they can recognize and eliminate CD19-expressing target cells.

More specifically, YESCARTA can be prepared from the patient's peripheral blood mononuclear cells, which are obtained via a standard leukapheresis procedure. The mononuclear cells are enriched for T cells and activated with anti-CD3 antibody in the presence of IL-2, then transduced with the replication incompetent retroviral vector containing the anti-CD19 CAR transgene. The transduced T cells are expanded in cell culture, washed, formulated into a suspension, and cryopreserved. The product must pass a sterility test before release for shipping as a frozen suspension in a patient specific infusion bag.

KYMRIAH™ (tisagenlecleucel) is a CD19-directed genetically modified autologous T cell immunotherapy comprised of autologous T cells that are genetically modified using a lentiviral vector to encode an anti-CD19 chimeric antigen receptor (CAR). The CAR is comprised of a murine single-chain antibody fragment (scFv) specific for CD19, followed by a CD8 hinge and transmembrane region that is fused to the intracellular signaling domains for 4-1BB (CD137) and CD3 zeta.

KYMRIAH can be prepared from the patient's peripheral blood mononuclear cells, which are obtained via a standard leukapheresis procedure. The mononuclear cells are enriched for T cells, then transduced with the lentiviral vector containing the anti-CD19 CAR transgene, and activated with anti-CD3/CD28 antibody coated beads. The transduced T cells are expanded in cell culture, washed, and formulated into a suspension, which then is cryopreserved. The product must pass a sterility test before release for shipping as a frozen suspension in a patient-specific infusion bag(s). The product is thawed prior to administration.

In some embodiments, the Car-T cells for Kymriah (tisagenlecleucel) or Yescarta (axicabtagene ciloleucel) can be modified by introducing an agent (e.g., described herein such as the gRNA/Cas9 described herein) that can knockout the HPK-1 gene, either simultaneously or sequentially with the introduction of retroviral vector containing the antiCD19 CAR transgene. The cells obtained can then be expanded in cell culture, washed, and formulated similar to the procedures for preparing Kymriah or Yescarta.

Pharmaceutical Compositions and Methods of Treatment

Modified immune cells, such as Car-T cells, have been recently approved for treating certain cancers. For example, YESCARTA is a CD19-directed genetically modified autologous T cell immunotherapy indicated for the treatment of adult patients with relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. Similarly, KYMRIAH is a CD19-directed genetically modified autologous T-cell immunotherapy indicated for the treatment of: Patients up to 25 years of age with B-cell precursor acute lymphoblastic leukemia (ALL) that is refractory or in second or later relapse; Adult patients with relapsed or refractory (r/r) large B-cell lymphoma after two or more lines of systemic therapy including diffuse large B-cell lymphoma (DLBCL) not otherwise specified, high grade B-cell lymphoma and DLBCL arising from follicular lymphoma.

As discussed herein, genetically disrupting HPK-1 gene in immune cells, such as Car-T cells (such as those for Yescarta or Kymriah), can further enhance the immunotherapy function, such as increased cytotoxicity and reduced exhaustion.

Accordingly, provided herein are also pharmaceutical compositions comprising the cells, cell populations, such as cells and populations produced by any of the methods herein, for example, for use in adoptive immunotherapy such as for treating cancer. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. Carriers are described, e.g., by Remington's Pharmaceutical Sciences 16th edition, Osol, A. Ed. (1980). In some embodiments, the choice of carrier is determined in part by the particular cell and/or by the method of administration.

Suitable preservatives include, for example, methylparaben, propylparaben, sodium benzoate, and benzalkonium chloride. In some embodiments, a mixture of two or more preservatives is used. The preservative or mixtures thereof are typically present in an amount of about 0.0001% to about 2% by weight of the total composition.

Suitable buffering agents include, for example, citric acid, sodium citrate, phosphoric acid, potassium phosphate, and various other acids and salts. In some embodiments, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington:

The Science and Practice of Pharmacy, Lippincott Williams & Wilkins; 21st ed. (May 1, 2005).

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Compositions in some embodiments are provided as sterile liquid preparations, e.g., isotonic aqueous solutions, suspensions, emulsions, dispersions, or viscous compositions, which may in some embodiments be buffered to a selected pH. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some embodiments be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin. The formulations to be used for in vivo administration are generally sterile. Sterility may be readily accomplished, e.g., by filtration through sterile filtration membranes.

In some embodiments, the present disclosure further provides methods, e.g., therapeutic methods for administrating the cells and compositions to subjects, e.g., human patients to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the methods herein, such as Car-T cells and end-of-production compositions following incubation and/or other processing steps, are administered to a subject, such as a subject having or at risk for the disease or condition. In some embodiments, the methods thereby treat, e.g., ameliorate one or more symptom of, the disease or condition, such as by lessening tumor burden in a cancer expressing an antigen recognized by an engineered T cell.

In some embodiments, the method comprising administering to a subject in need thereof a therapeutically effective amount of the immune cells with the HPK-1 genetic disruption or cell compositions herein.

In some embodiments, the method comprises (a) obtaining an immune cell (e.g., T cell) from a subject in need of the treatment; (b) introducing an agent that induces or is capable of inducing HPK-1 genetic disruption in the immune cell (e.g., T cell); (c) incubating and optionally expanding the immune cell with the agent to provide a HPK-1 gene disrupted cell population; and (d) administering the HPK-1 gene disrupted cell population to the subject. In some embodiments, the method further comprises (e) introducing in the immune cell (e.g., T cell) a nucleic acid encoding a recombinant receptor, such as a CAR as described herein, or product thereof. The introducing steps of (b) and (e) can occur simultaneously or sequentially in any order. Suitable agents and recombinant receptors include those described herein.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some embodiments, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

Suitable diseases or disorders to be treated by the methods herein include tumors, including solid tumors, hematologic malignancies, and melanomas, and infectious diseases, such as infection with a virus or other pathogen, e.g., HIV, HCV, HBV, CMV, and parasitic disease. In some embodiments, the disease or condition is a tumor, cancer, malignancy, neoplasm, or other proliferative disease or disorder. Such diseases include but are not limited to the disease or condition is a cancer or tumor, which can be a leukemia, lymphoma, chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, colon cancer, lung cancer, liver cancer, breast cancer, prostate cancer, ovarian cancer, skin cancer, melanoma cancer, bone cancer, brain cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the disease or disorder is associated with an antigen selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD276, CD44, EGFR, EGP-2, EGP-4, EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3 and/or biotinylated molecules, and/or molecules expressed by HIV, HCV, HBV or other pathogens. For example, in some embodiments, the disease or disorder can be associated with cells expressing CD19, BCMA, Integrin αVβ6, MUC1, EGFRvIII, HER2, EGFR, GD2, and/or Mesothelin.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntval injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments can be measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some embodiments the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 111 (1995), and U.S. Pat. No. 5,087,616.

Definitions

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various embodiments of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For brevity, as used herein, when the term "at least about", "about" or the like is followed by a series of numbers, it should be understood that each of these numbers is preceded by such term. For example, at least about 50%, 60%, 70%, or 80%, should be understood as at least about 50%, at least about 60%, at least about 70%, or at least about 80%. Also for brevity, the symbol "%" may be at times be omitted when it is obvious from context that the same denominator is intended. For example, when describing percentages, about 50, 60, . . . , or 90% should be understood as about 50%, about 60%, . . . , or about 90%.

As used herein, "percent (%) amino acid sequence identity" and "percent identity" when used with respect to an amino acid sequence (reference polypeptide sequence) is defined as the percentage of amino acid residues in a candidate sequence (e.g., a streptavidin mutein) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

An amino acid substitution may include replacement of one amino acid in a polypeptide with another amino acid Amino acids generally can be grouped according to the following common side-chain properties:
(1) hydrophobic: Norleucine, Met, Ala, Val, Leu, He;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative amino acid substitutions will involve exchanging a member of one of these classes for another class.

"Non-homologous end joining" or "NHEJ", as used herein, refers to ligation mediated repair and/or non-template mediated repair including, e.g., canonical NHEJ (cNHEJ), alternative NHEJ (altNHEJ), microhomology-mediated end joining (MMEJ), single-strand annealing (SSA), and synthesis-dependent microhomology-mediated end joining (SD-MMEJ).

A "gRNA molecule" refers to a nucleic acid that promotes the specific targeting or homing of a gRNA molecule/Cas9 molecule complex to a target nucleic acid, such as a locus on the genomic DNA of a cell.

"Replacement", or "replaced", as used herein with reference to a modification of a molecule does not require a process limitation but merely indicates that the replacement entity is present.

As used herein, a subject includes any living organism, such as humans and other mammals. Mammals include, but are not limited to, humans, and non-human animals, including farm animals, sport animals, rodents and pets. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human. In other embodiments, the subject is poultry.

As used herein, a composition refers to any mixture of two or more products, substances, or compounds, including cells. It may be a solution, a suspension, liquid, powder, a paste, aqueous, non-aqueous or any combination thereof.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some embodiments will be higher than the therapeutically effective amount.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

Exemplary Embodiments

In one embodiment, the present invention provides a method for genetically modifying a HPK1 gene, wherein said method comprises genetically modifying the HPK1 gene such that the hpk1 protein's function is inactivated or its activity is decreased. In various embodiments, the method of the invention is simple in operation, high in knockout efficiency, and effective in enhancing the tumor killing activity of the T cell. The T cells modified by the method of the present invention have broad clinical application prospects.

The genetic modification herein includes gene knockout, partial gene deletion, gene replacement, and insertion. In some embodiments, the genetic modification comprises genetically modifying a second exon of the HPK1 gene. In some embodiments, the genetic modification comprises modifying the HPK1 gene using a gene editing technology. Various gene editing technology can be used. For example, in some embodiments, the gene editing technology includes embryonic stem cell-based DNA homologous recombination technology, CRISPR/Cas9 technology, zinc finger nuclease technology, transcriptional activator-like effector nuclease technology, homing endonuclease or other molecular biology technology; preferably, the genetic modification is performed using CRISPR/Cas9 based gene editing technology.

In some embodiments, the method comprises knocking out the HPK1 gene with a gRNA targeting the HPK1 gene. For example, in some embodiments, the gRNA targets a second exon of the HPK1 gene. The gRNA and the Cas9 protein is typically used together to knock out the HPK1 gene.

In some embodiments, the method comprises preparing a gRNA. In some embodiments, the method of preparing the gRNA comprises: (1) constructing a gRNA loading plasmid; and (2) in vitro transcribing the gRNA. In some embodiments, the step (1) comprises synthesizing the gRNA coding strand and the complementary strand, inserting the double-stranded DNA formed by annealing the coding strand and the complementary strand into the pUC57 vector, and placing it under the control of the T7 promoter to construct pUC57kan-T7-gRNA. In some embodiments, the step (2) comprises purifying the gRNA loading plasmid pUC57kan-T7-gRNA identified through the enzymatic digestion and sequencing, and in vitro transcribing the HPK1 gRNA/HPK1 gRNA using the T7 RNA in vitro transcription kit, and purifying the transcription product to obtain the gRNA. In some embodiments, the in vitro transcription for HPK1 gRNA/HPK1 gRNA is performed using the T7 RNA in vitro transcription kit. In some embodiments, the double-stranded DNA template sequence of the gRNA is as set forth in SEQ ID NO: 3 and SEQ ID NO: 4: F: 5'-TAGG GACCTGGTGGCACTGAAGA-3' (SEQ ID NO:3) R: 5'-AAAC TCTTCAGTGCCACCAGGTC-3' (SEQ ID NO:4). In some embodiments, the gRNA comprises a targeting domain complementary to the target domain of sequence GACCTGGTGGCACTGAAGA.

In some embodiments, the method comprises genetically modifying the HPK1 gene of a mononuclear cell; preferably, the mononuclear cell is a human peripheral blood mononuclear cell; more preferably, the human peripheral blood mononuclear cell is T cell, NK cell or NKT cell; more preferably, the human peripheral blood mononuclear cell is CD3+ T cell. Most preferably, the human peripheral blood mononuclear cell further expresses an exogenous chimeric antigen receptor. For example, in some embodiments, the method comprises: (1) preparing the gRNA targeting the HPK1 gene; (2) preparing a Cas9 protein; (3) culturing and expanding the mononuclear cells in vitro; (4) co-transfecting the gRNA of step (1) and the Cas9 protein of step (2) into the mononuclear cells of step (3).

The knockout efficiency can be determined by methods known in the art or as described herein. In some embodiments, the method further comprises identifying a knockout efficiency of the HPK1 gene in the mononuclear cell after the co-transfection in step (4), preferably, the knockout efficiency of the HPK1 gene in the human peripheral blood mononuclear cell is identified by PCR—enzymatic digestion and/or Western Blot method. In some embodiments, the knockout efficiency of the HPK1 gene in the mononuclear cell can be identified with the following procedure: the PCR amplification is performed using the primers shown in SEQ ID NO: 7 and SEQ ID NO: 8, the PCR product is subjected to the heat denaturation, annealing and renaturation followed by T7 endonuclease treatment, and the cleavage efficiency is identified with an agarose gel electrophoresis; alternatively, the knockout efficiency of the HPK1 gene in the mononuclear cell is identified with the following procedure: the total protein in the mononuclear cell is extracted, subjected to SDS-PAGE, transferred to a membrane, and subjected to Western Blot with an anti-HPK1 antibody as a primary antibody. In some embodiments, the method further comprises step (5): expressing the human derived chimeric antigen receptor (CAR) in the mononuclear cell co-transfected with the gRNA and the Cas9 protein obtained in step (4). In some embodiments, the human derived chimeric antigen receptor is CAR19, BCMA, Integrin αVβ6, MUC1, EGFRvIII, HER2, EGFR, GD2, Mesothelin.

In some embodiments, the present invention also provides a method for enhancing the killing activity of a mononuclear cell or a method for increasing the Th1 cytokine secretion level of a mononuclear cell.

In some embodiments, the present invention provides a method for enhancing the killing activity of the peripheral blood mononuclear cells. In some embodiments, the method comprises: (1) preparing a gRNA targeting the HPK1; (2) preparing a Cas9 protein; (3) culturing and expanding the human peripheral blood mononuclear cells in vitro; (4) co-transfecting the gRNA of step (1) and the Cas9 protein of step (2) into the human peripheral blood mononuclear cells of step (3).

In the method for enhancing the killing activity of the peripheral blood mononuclear cells of the present invention, preferably, the human peripheral blood mononuclear cell is T cell, NK cell, NKT cell, more preferably, the peripheral blood mononuclear cell is CD3+ T cell.

In the method for enhancing the killing activity of the peripheral blood mononuclear cells of the present invention, preferably, the human peripheral blood mononuclear cell further expresses an exogenous chimeric antigen receptor.

In the method for enhancing the killing activity of the peripheral blood mononuclear cells of the present invention, the method further comprises step (5) of expressing the human derived CAR in the CD3+ human peripheral blood mononuclear cells transfected with the gRNA and the Cas9 protein obtained in step (4). Preferably, the human derived chimeric antigen receptor is CD19, BCMA, Integrin αVβ6, MUC1, EGFRvIII, HER2, EGFR, GD2, Mesothelin.

In the method for enhancing the killing activity of the peripheral blood mononuclear cells of the present invention, wherein the step (4) further comprises identifying the knockout efficiency of the HPK1 gene in the human peripheral blood mononuclear cells.

In the method for enhancing the killing activity of the peripheral blood mononuclear cells of the present invention, preferably, the knockout efficiency of the HPK1 gene in the human peripheral blood mononuclear cells is identified by PCR—enzymatic digestion and/or Western Blot method.

In the method for enhancing the killing activity of the peripheral blood mononuclear cells of the present invention, wherein the knockout efficiency of the HPK1 gene in the human peripheral blood mononuclear cells is identified with the following procedure: the PCR amplification is performed using the primers shown in SEQ ID NO: 7 and SEQ ID NO: 8, the PCR product is subjected to the heat denaturation, annealing and renaturation followed by T7 endonuclease treatment, and the cleavage efficiency is identified with an agarose gel electrophoresis.

In the method for enhancing the killing activity of the peripheral blood mononuclear cells of the present invention, wherein the knockout efficiency of the HPK1 gene in the human peripheral blood mononuclear cells is identified with the following procedure: the total protein in the human peripheral blood mononuclear cells is extracted, subjected to SDS-PAGE, transferred to a membrane, and subjected to Western Blot with an anti-HPK1 antibody as a primary antibody.

Further, the present invention provides a method for increasing the Th1 cytokine secretion level in the peripheral blood mononuclear cells, comprising: (1) preparing a gRNA targeting HPK1; (2) preparing a Cas9 protein; (3) culturing and expanding the human peripheral blood mononuclear cells in vitro; (4) co-transfecting the gRNA of step (1) and the Cas9 protein of step (2) into the human peripheral blood mononuclear cells of step (3).

In the method for increasing the Th1 cytokine secretion level in the peripheral blood mononuclear cells of the present invention, preferably, the human peripheral blood mononuclear cell is T cell, NK cell, NKT cell, more preferably, the human peripheral blood mononuclear cell is CD3+ T cell.

In the method for increasing the Th1 cytokine secretion level in the peripheral blood mononuclear cells of the present invention, preferably, the human peripheral blood mononuclear cell further expresses an exogenous chimeric antigen receptor.

In the method for increasing the Th1 cytokine secretion level in the peripheral blood mononuclear cells of the present invention, the method further comprises step (5) of expressing the human derived CAR in the CD3+ human peripheral blood mononuclear cells transfected with the gRNA and the Cas9 protein obtained in step (4), preferably, the human derived chimeric antigen receptor is CAR19.

In the method for increasing the Th1 cytokine secretion level in the peripheral blood mononuclear cells of the present invention, wherein the step (4) further comprises identifying the knockout efficiency of the HPK1 gene in the human peripheral blood mononuclear cells.

In the method for increasing the Th1 cytokine secretion level in the peripheral blood mononuclear cells of the present invention, preferably, the knockout efficiency of the HPK1 gene in the human peripheral blood mononuclear cells is identified by PCR—enzymatic digestion and/or Western Blot method.

In the method for increasing the Th1 cytokine secretion level in the peripheral blood mononuclear cells of the present invention, wherein the knockout efficiency of the HPK1 gene in the human peripheral blood mononuclear cells is identified with the following procedure: the PCR amplification is performed using the primers shown in SEQ ID NO: 7 and SEQ ID NO: 8, the PCR product is subjected to the heat denaturation, annealing and renaturation followed by T7 endonuclease treatment, and the cleavage efficiency is identified with an agarose gel electrophoresis.

In the method for increasing the Th1 cytokine secretion level in the peripheral blood mononuclear cells of the present invention, wherein the knockout efficiency of the HPK1 gene in the human peripheral blood mononuclear cells is identified with the following procedure: the total protein in the human peripheral blood mononuclear cells is extracted, subjected to SDS-PAGE, transferred to a membrane, and subjected to Western Blot with an anti-HPK1 antibody as a primary antibody.

In a second embodiment, the present invention also provides a reagent for genetically modifying a HPK1 gene, the HPK1 gene is genetically modified by the reagent such that the hpk1 protein's function is inactivated or its activity is decreased. In some embodiments, the genetic modification includes gene knockout, partial gene deletion, gene replacement, and insertion. In some embodiments, the genetic modification comprises genetically modifying a second exon of the HPK1 gene. In some embodiments, the genetic modification comprises modifying the HPK1 gene using a gene editing technology; preferably, the gene editing technology includes embryonic stem cell-based DNA homologous recombination technology, CRISPR/Cas9 technology, zinc finger nuclease technology, transcriptional activator-like effector nuclease technology, homing endonuclease or other molecular biology technology; more preferably, the genetic modification is performed using CRISPR/Cas9 based gene editing technology. In some embodiments, the reagent is a gRNA that targets the HPK1 gene to knock out the HPK1 gene; preferably, the gRNA targets a second exon of the HPK1 gene. In some embodiments, the gRNA is capable of pairing with (e.g., complementary to) the sequence set forth in SEQ ID NO: 1. In some embodiments, the method of preparing the gRNA comprises: (1) constructing a gRNA loading plasmid; and (2) in vitro transcribing the gRNA. In some embodiments, the step (1) comprises synthesizing the gRNA coding strand and the complementary strand, inserting the double-stranded DNA formed by annealing the coding strand and the complementary strand into the pUC57 vector, and placing it under the control of the T7 promoter to construct pUC57kan-T7-gRNA. In some embodiments, the step (2) comprises purifying the gRNA loading plasmid pUC57kan-T7-gRNA identified through the enzymatic digestion and sequencing, and in vitro transcribing the HPK1 gRNA/HPK1 gRNA using the T7 RNA in vitro transcription kit, and purifying the transcription product to obtain the gRNA. In some embodiments, the double-stranded DNA template sequence of the gRNA is as set forth in SEQ ID NO: 3 and SEQ ID NO: 4.

In some embodiments, the agent further comprises a Cas9 protein; preferably, the Cas9 is recombinantly expressed. In some embodiments, the Cas9 protein is produced by the following method: (1) preparing a full-length human Cas9 cDNA after codon optimization according to the amino acid sequence of the human Cas9 protein; (2) adding nuclear localization signals to the 5' and 3' ends of the full-length human Cas9 cDNA of step (1) to construct a recombinant expression plasmid; (3) introducing the recombinant expression plasmid into a host cell to express the recombinant Cas9 protein; (4) purifying and concentrating the recombinantly expressed Cas9 protein; and (5) excising the purification tag and recovering the Cas9 protein of about 160 kD.

In some embodiments, the reagent further comprises a chimeric antigen receptor.

In a third embodiment, the present invention also provides the use of any one of the above reagents in genetic modification. In some embodiments, the use is for knocking out the HPK1 gene in the mononuclear cell, or increasing the killing activity of the mononuclear cell, or increasing the Th1 cytokine level in the mononuclear cell.

In a fourth embodiment, the present invention provides a mononuclear cell prepared by any one of the methods herein. In some embodiments, the mononuclear cell is a human peripheral blood mononuclear cell, preferably, the human peripheral blood mononuclear cell is T cell, NK cell, or NKT cell, more preferably, is CD3+ T cell, further preferably CD3+ T cell expressing an exogenous human chimeric antigen receptor, and most preferably CD3+ T cell chimerized with single-chain antibodies specific for CD19, BCMA, Integrin 01136, MUC1, EGFRvIII, HER2, EGFR, GD2, Mesothelin and the like.

Compared with the unmodified peripheral blood mononuclear cells, the peripheral blood mononuclear cells of the present invention with deleted HPK1 gene have stronger killing capability, and the higher Th1 cytokine secretion level. Preferably, it also has specificity for tumors.

In a fifth embodiment, the present invention also provides the use of any one of the above reagents or any one of the above mononuclear cells for preparing a pharmaceutical composition for modifying the HPK1 gene in the mononuclear cell, or increasing the killing activity of the mononuclear cell, or increasing the Th1 cytokine level in the mononuclear cell. In some embodiments, the pharmaceutical composition is for the treatment of a tumor. Preferably, the tumor is a lymphoma or a solid tumor.

In a sixth embodiment, the present invention also provides a pharmaceutical composition comprising any one of the above reagents or any one of the above mononuclear cells.

The technical solution of the present invention has at least the following advantages: (1) The operation is easy and the knockout efficiency is high. In the present invention, a gRNA capable of efficiently targeting HPK1 is designed by obtaining a target sequence located on the second exon of the T cell genomic HPK1 through multiple experiments. The method of the invention is easy to operate and suitable for the modification of the in vitro cultured T cells compared with other knockout methods. Compared with the other target sequences, the target sequence of the present invention is particularly suitable for CRISPR/Cas9 gene editing technology, and can efficiently knock out HPK1 of T cells by CRISPR/Cas9 technology. (2) The degree of T cell activation is high, and the tumor killing effect is good. The modified T cells of the invention not only proliferate faster, but also have stronger tumor killing activity per cell. The experimental result of the tumor killing activity shows that the tumor killing activity of the modified T cells of the invention is higher or even significantly higher than he PD1 modified T cells. (3) It can be combined with other T cell modification technology to achieve a synergistic tumor killing activity. In the present invention, the T cell modification technology of CRISPR/Cas9 knockout of HPK1 gene is combined with CAR-T technology to have a synergistic effect. Through in vitro killing experiment analysis, the invention is not only superior to the technical effect of single CAR-T, but also superior to the technical effect of CAR-T combined with PD-1 knockout. And (4) It can suppress the depletion of T cells. In the present invention, the HPK1 gene of T cells is knocked out by CRISPR/Cas9, and the flow cytometry analysis shows that, knockdown of HPK1 may lead to down-regulation of PD1 and TIM3 expression levels. Thus, it can be seen that HPK1 knockout may increase the ability of T cells to kill target cells and secrete cytokines by inhibiting T cell depletion.

Alternative Exemplary Embodiments 1-34

The following presents some further exemplary embodiments of the present disclosure:

1. A method for genetically modifying a HPK1 gene, characterized in that said method comprises genetically modifying the HPK1 gene such that the hpk1 protein's function is inactivated or its activity is decreased.
2. The method according to embodiment 1, characterized in that the genetic modification includes gene knockout, partial gene deletion, gene replacement, and insertion.
3. The method according to any one of embodiments 1-2, characterized in that the genetic modification comprises genetically modifying a second exon of the HPK1 gene.
4. The method according to any one of embodiments 1-3, characterized in that the genetic modification comprises modifying the HPK1 gene using a gene editing technology.
5. The method according to embodiment 4, characterized in that the gene editing technology includes embryonic stem cell-based DNA homologous recombination technology, CRISPR/Cas9 technology, zinc finger nuclease technology, transcriptional activator-like effector nuclease technology, homing endonuclease or other molecular biology technology; preferably, the genetic modification is performed using CRISPR/Cas9 based gene editing technology.
6. The method according to embodiment 5, characterized in that the method comprises knocking out the HPK1 gene with a gRNA targeting the HPK1 gene.
7. The method according to embodiment 6, characterized in that the gRNA targets a second exon of the HPK1 gene.
8. The method according to any one of embodiments 6-7, characterized in that the gRNA and the Cas9 protein knock out the HPK1 gene together.
9. The method according to any one of embodiments 6-8, characterized in that the method of preparing the gRNA comprises:
  (1) the construction of a gRNA loading plasmid;
  (2) the in vitro transcription of the gRNA;
  wherein the step (1) comprises synthesizing the gRNA coding strand and the complementary strand, inserting the double-stranded DNA formed by annealing the coding strand and the complementary strand into the pUC57 vector, and placing it under the control of the T7 promoter to construct pUC57kan-T7-gRNA;
  the step (2) comprises purifying the gRNA loading plasmid pUC57kan-T7-gRNA identified through the enzymatic digestion and sequencing, and in vitro transcribing the HPK1 gRNA/HPK1 gRNA using the T7 RNA in vitro transcription kit, and purifying the transcription product to obtain the gRNA.
10. The method according to embodiment 9, characterized in that the double-stranded DNA template sequence of the gRNA is as set forth in SEQ ID NO: 3 and SEQ ID NO: 4.
11. The method according to any one of embodiments 1-10, characterized in that the genetic modification comprises genetically modifying the HPK1 gene of a mononuclear cell; preferably, the mononuclear cell is a human peripheral blood mononuclear cell; more preferably, the human peripheral blood mononuclear cell is T cell, NK cell or NKT cell; more preferably, the human peripheral blood mononuclear cell is CD3+ T cell; and most preferably, the human peripheral blood mononuclear cell further expresses an exogenous chimeric antigen receptor.
12. The method according to embodiment 11, characterized in that the method comprises:
  (1) preparing the gRNA targeting the HPK1 gene;
  (2) preparing the Cas9 protein;
  (3) culturing and expanding the mononuclear cells in vitro;
  (4) co-transfecting the gRNA of step (1) and the Cas9 protein of step (2) into the mononuclear cells of step (3).
13. The method according to embodiment 12, characterized in that the method further comprises identifying a knockout efficiency of the HPK1 gene in the mononuclear cell after the co-transfection in step (4), preferably, the knockout efficiency of the HPK1 gene in the human peripheral blood mononuclear cells is identified by PCR—enzymatic digestion and/or Western Blot method.
14. The method according to embodiment 13, characterized in that the knockout efficiency of the HPK1 gene in the mononuclear cells is identified with the following procedure: the PCR amplification is performed using the primers shown in SEQ ID NO: 7 and SEQ ID NO: 8, the PCR product is subjected to the heat denaturation, annealing and renaturation followed by T7 endonuclease treatment, and the cleavage efficiency is identified with an agarose gel electrophoresis; alternatively, the knockout efficiency of the HPK1 gene in the mononuclear cells is identified with the following procedure: the total protein in the mononuclear cells is extracted, subjected to SDS-PAGE, transferred to a membrane, and subjected to Western Blot with an anti-HPK1 antibody as a primary antibody.
15. The method according to any one of embodiments 12-14, characterized in that the method further comprises step (5) of expressing the human derived chimeric antigen receptor (CAR) in the mononuclear cell co-transfected with the gRNA and the Cas9 protein obtained in step (4).
16. The method according to embodiment 15, characterized in that the human derived chimeric antigen receptor is CAR19.
17. A reagent for genetically modifying a HPK1 gene, characterized in that the HPK1 gene is genetically modified by the reagent such that the hpk1 protein's function is inactivated or its activity is decreased.
18. The reagent according to embodiment 17, characterized in that the genetic modification includes gene knockout, partial gene deletion, gene replacement, and insertion.

19. The reagent according to any one of embodiments 17-18, characterized in that wherein the genetic modification comprises genetically modifying a second exon of the HPK1 gene.
20. The reagent according to any one of embodiments 17-19, characterized in that the genetic modification comprises modifying the HPK1 gene using a gene editing technology; preferably, the gene editing technology includes embryonic stem cell-based DNA homologous recombination technology, CRISPR/Cas9 technology, zinc finger nuclease technology, transcriptional activator-like effector nuclease technology, homing endonuclease or other molecular biology technology; more preferably, the genetic modification is performed using CRISPR/Cas9 based gene editing technology.
21. The reagent according to embodiment 20, characterized in that the reagent is a gRNA that targets the HPK1 gene to knock out the HPK1 gene; preferably, the gRNA targets a second exon of the HPK1 gene.
22. The reagent according to embodiment 21, characterized in that the gRNA is capable of pairing with the sequence set forth in SEQ ID NO: 1.
23. The reagent according to any one of embodiments 21-22, characterized in that the method of preparing the gRNA comprises:
    (1) the construction of a gRNA loading plasmid;
    (2) the in vitro transcription of the gRNA;
    wherein the step (1) comprises synthesizing the gRNA coding strand and the complementary strand, inserting the double-stranded DNA formed by annealing the coding strand and the complementary strand into the pUC57 vector, and placing it under the control of the T7 promoter to construct pUC57kan-T7-gRNA;
    the step (2) comprises purifying the gRNA loading plasmid pUC57kan-T7-gRNA identified through the enzymatic digestion and sequencing, and in vitro transcribing the HPK1 gRNA/HPK1 gRNA using the T7 RNA in vitro transcription kit, and purifying the transcription product to obtain the gRNA.
24. The reagent according to any one of embodiment 23, characterized in that the double-stranded DNA template sequence of the gRNA is as set forth in SEQ ID NO: 3 and SEQ ID NO: 4.
25. The reagent according to any one of embodiments 21-24, characterized in that the agent further comprises a Cas9 protein; preferably, the Cas9 is recombinantly expressed.
26. The reagent according to embodiment 25, characterized in that the Cas9 protein is produced by the following method:
    (1) preparing a full-length human Cas9 cDNA after codon optimization according to the amino acid sequence of the human Cas9 protein;
    (2) adding nuclear localization signals to the 5' and 3' ends of the full-length human Cas9 cDNA of step (1) to construct a recombinant expression plasmid;
    (3) introducing the recombinant expression plasmid into a host cell to express the recombinant Cas9 protein;
    (4) purifying and concentrating the recombinantly expressed Cas9 protein; and
    (5) excising of the purification tag and recovering the Cas9 protein of about 160 kD.
27. The reagent according to any one of embodiments 21-26, characterized in that the reagent further comprises a chimeric antigen receptor.
28. Use of the reagent according to any one of embodiments 17-27 in the genetic modification.
29. The use according to embodiment 28, characterized in that the use is for knocking out the HPK1 gene in the mononuclear cell, or increasing the killing activity of the mononuclear cell, or increasing the Th1 cytokine level in the mononuclear cell.
30. A mononuclear cell, characterized in that the mononuclear cells are prepared by the method of any one of embodiments 1-16.
31. The mononuclear cell according to embodiment 30, characterized in that the mononuclear cell is a human peripheral blood mononuclear cell, preferably, the human peripheral blood mononuclear cell is T cell, NK cell, or NKT cell, more preferably, is CD3+ T cell, further preferably CD3+ T cell expressing an exogenous human chimeric antigen receptor, and most preferably CD3+ T cell chimerized with single-chain antibodies specific for CD19, BCMA, Integrin 01136, MUC1, EGFRvIII, HER2, EGFR, GD2, Mesothelin and the like.
32. Use of the reagent according to any one of embodiments 17-27 or the mononuclear cell according to any one of embodiments 30-31 for the preparation of a pharmaceutical composition, characterized in that the pharmaceutical composition is for modifying the HPK1 gene in the mononuclear cell, or increasing the killing activity of the mononuclear cell, or increasing the Th1 cytokine level in the mononuclear cell.
33. The use according to embodiment 32, characterized in that the pharmaceutical composition is for the treatment of a tumor, preferably, the tumor is a lymphoma or a solid tumor.
34. A pharmaceutical composition, characterized in that the pharmaceutical composition comprises the reagent according to any one of embodiments 17-27 or the mononuclear cell according to any one of embodiments 30-31.

EXAMPLES

Exemplary embodiments of the present disclosure will be described in more detail below with reference to the accompanying drawings. Although the exemplary embodiments of the present disclosure are shown in the drawings, it should be understood that the disclosure may be embodied in various forms and should not be limited by the embodiments set forth herein. Rather, these embodiments are provided so that this disclosure will be more fully understood and the scope of the disclosure can be fully conveyed to those skilled in the art.

Examples

General Methods and Material

The reagents used for the Examples herein are generally commercially available or can be prepared by standard technique in the art. For examples, the various antibodies used for the examples are commercially available as follows:

| REAGENT or RESOURCE | SOURCE | IDENTIFIER |
|---|---|---|
| Antibodies | | |
| HPK1, Rabbit mAb | Cell Signaling Technology | 4472 |
| PD-1 (D4W2J), Rabbit mAb | Cell Signaling Technology | 86163 |
| β-Actin (13E5), Rabbit mAb | Cell Signaling Technology | 4970 |

| REAGENT or RESOURCE | SOURCE | IDENTIFIER |
|---|---|---|
| Antibodies | | |
| Ultra-LEAF ™ Purified anti-human CD3 Antibody | Biolegend | 317326 |
| Ultra-LEAF ™ Purified anti-human CD28 Antibody | Biolegend | 302934 |
| Annexin V, PE/Cy7 | Biolegend | 640949 |
| Goat Anti-Rabbit IgG, FITC | BD Biosciences | 554020 |
| CD3, eFlour 660(clone OKT3) | eBioscience | 50-0037-42 |
| TIM-3, FITC(clone F38-2E2) | eBioscience | 11-3109-41 |
| PD-1, APC-eFlour 780 (clone eBioJ105) | eBioscience | 47-2279-42 |
| LAG-3, PE(clone 3DS223H) | eBioscience | 12-2239-42 |
| CD107a, APC(clone H4A3) | Biolegend | 328619 |
| CD62L, PE-eFluor 610 (clone DREG-56) | eBioscience | 61-0629-42 |
| CD45RO, eFluor 450 (clone UCHL1) | eBioscience | 48-0457-42 |
| THETM NWSHPQFEK Tag Antibody, FITC | GeneScript | A01736-100 |
| CD269, PE/Cy7 (clone 19F2) | Biolegend | 357508 |
| CFSE | BD Biosciences | 565082 |

Cell lines: The cell lines Raji, Daudi, K562, U266, RPMI8226 and Jurkat cells were cultured in RPMI 1640 and 293T were cultured in DMEM supplemented with 10% PBS and 1% penicillin/streptomycin in a 5% $CO_2$ incubator at 37° C. Human PBMC were cultured in X-VIVO15 in a 5% $CO_2$ incubator at 37° C.

Lentiviral vector production and transduction: CD19 CAR, Her2 CAR, and BCMA CAR-encoding lentiviral supernatants were produced via transient transfection of the lenti-293T cell line. Briefly, lenti-293T cells were transfected via Lipofectamine 2000 (Life Technologies) with the plasmids encoding the CARs and the Lentivirus envelope protein. Supernatants were collected 48 and 72 h after transfection.

T cell isolation and modification: Human T cells were activated and transduced as described previously. Briefly, peripheral blood mononuclear cells (PBMCs) were isolated from healthy donor peripheral blood or leukopacks (xijing hospital). All experiments were performed in compliance with all relevant ethical regulations and in accordance with IRB 095091. PBMCs were activated with 5 µg/ml CD3 antibody, 3 µg/ml CD28 antibody and 100 IU/ml of IL-2 for 2 d before transduction. Mouse T cells were mechanically isolated from spleens and activated using IL-2 and 5 µg/ml CD3 antibody, 3 µg/ml CD28 antibody. Transduction was achieved by centrifugation of activated PBMCs and retroviral supernatant on RetroNectin-coated plates on 3 consecutive days (TakaraBio).

mRNA in vitro transcription and Cas9 Protein purification: T7 mscript systems kit (Ambion) was used to generate in vitro transcription RNA. Cas9 Protein purification: Cas9 gene was cloned into a pGEX4T-1 plasmid (Invitrogen) following known procedure. pGEX4T-1-Cas9 plasmid was constructed using one step cloning kit (vazyme). The proteins were expressed in E. coli BL21 Rosetta 2(DE3). Cultures (2 L) were grown at 37° C. in Terrific Broth medium containing 50 µg/ml kanamycin and 34 µg/ml chloramphenicol until the A600 reached 0.6. The cultures were supplemented with 0.2 mM isopropyl-1-thio-β-d-galactopyranoside and incubation was continued for 16 h at 16° C. with constant shaking. The cells were harvested by centrifugation and the pellets stored at −80° C. All subsequent steps were performed at 4° C. Thawed bacteria were resuspended in 30 ml of buffer A (20 mM Tris-HCl pH 7.5, 300 mM NaCl, 200 mM $Li_2SO_4$, 10 mM Imidazole) supplemented with complete EDTA free protease inhibitor tablet (Roche). Triton X-100 was added to final concentrations of 0.1%. After 30 mM, the lysate was sonicated to reduce viscosity. Insoluble material was removed by centrifugation for 1 hr at 17,000 rpm in a Beckman JA-3050 rotor. The soluble extract was bound in batch to mixed for 1 hr with 5 ml of Ni2+-Nitrilotriacetic acid-agarose resin (Qiagen) that had been pre-equilibrated with buffer A. The resin was recovered by centrifugation, and then washed extensively with buffer A. The bound protein was eluted step-wise with aliquots of IMAC buffer (50 mM Tris-HCl pH 7.5, 250 mM NaCl, 10% glycerol) containing increasing concentrations of imidazole. The 200 mM imidazole elutes containing the His6-MBP tagged Cas9 polypeptide was pooled together. The His6-MBP affinity tag was removed by cleavage with TEV protease during overnight dialysis against 20 mM Tris-HCl pH 7.5, 150 mM NaCl, 10% glycerol. The tagless Cas9 protein was separated from the fusion tag by using a 5 ml SP Sepharose HiTrap column (GE Life Sciences). The protein was further purified by size exclusion chromatography using a Superdex 200 10/300 GL in 20 mM Tris HCl pH 7.5, 150 mM KCl, 1 mM TCEP, and 5% glycerol. The elution peak from the size exclusion was aliquoted, frozen and kept at −80° C.

Gene targeting: 48 h after initiating T-cell activation, and the T cells were transfected by electrotransfer of Cas9 protein and gRNA using an BTX EM830 (Harvard Apparatus BTX). $1 \times 10^6$ cells were mixed with 3 µg of Cas9 and 2 µg of gRNA into a 0.2 cm cuvette. Following electroporation cells were diluted into culture medium and incubated at 37° C., 5% $CO_2$. CAR-Lenti virus was added to the culture 2 to 4 h after electroporation, at the indicated multiplicity of infection ($1 \times 10^5$ to $1 \times 10^6$ range). Subsequently, edited cells were cultured using standard conditions (37° C. and expanded in T-cell growth medium, replenished as needed to maintain a density of ~$1 \times 10^6$ cells per ml every 2 to 3 days).

In Vivo Mouse Studies: NOD-SCIDg/(NSG) mice can be obtained from Charles River Laboratories, China. All mice were housed according to the guidelines of the Tsinghua University laboratory animal research center and Animal Care and Use Committee. All animals were maintained in pathogen-free conditions and cared for in accordance with the International Association for Assessment and Accreditation of Laboratory Animal Care policies and certification.

In vivo bioluminescence imaging: D-luciferin (PerkinElmer, Waltham, Mass., USA) suspended in PBS (15 mg/ml) was injected (150 mg/kg) i.p. 5 min before acquisitions. Bioluminescence images were collected on a Xenogen IVIS Spectrum Imaging System (Xenogen, Alameda, Calif., USA). Living Image software Version 3.0 (Xenogen) was used to acquire and quantify the bioluminescence imaging data sets.

Flow cytometry: Tumors separated from mice were minced with scissors and then digested with a Tumor Dissociation Kit and ground using gentleMACS (Miltenyi Biotec) to generate single-cell suspensions. Cells from spleens were isolated by grinding spleens through 70 µm filters. The cells were washed and then stained with antibodies for 15 min in the dark and then detected by flow cytometry. For intracellular staining, cells were further permeabilized using a Fixation and Permeabilization kit (BD Bioscience) and stained by antibodies. All samples were analyzed with an LSR Fortessa or FACS AriaII (BD Bioscience) and data were analyzed using FlowJo software. CD19 CARs were detected with the THETM NWSHPQFEK Tag Antibody, FITC and human CD3 antibody. Her2 and BCMA CARs were detected with biotinylated protein L (Pierce Protein Biology) and human CD3 antibody. All FACS plots presenting CAR T cell phenotype data were conducted on gated CAR+ cells. For mock-transduced T cells, whole T cell populations were used for analysis.

Cytotoxicity assays of human CAR-T cells: The ability of CAR-T cells to kill targets was tested in a12-h CytoTox 96® Non-Radioactive Cytotoxicity Assay. Transduced T cells and UTD T cells were thawed and rested for 24 h at 37° C. in a 6-well plate in T cell medium. The effectors and targets were mixed together at the indicated effector:target (E:T) ratios and cultured in blackwalled 96-well flat-bottom plates with 3×104 target cells in a total volume of 200 µl per well in T cell medium. After 12 h, transfer 50 µl aliquots from all test and control wells to a fresh 96-well flat clear bottom plate, and 50 µl of the CytoTox 96® Reagent (Promega) was added to to each sample aliquot. Cover the plate with foil or an opaque box to protect it from light and incubate for 30 minutes at room temperature. Add 50 µl of Stop Solution to each well of the 96-well plate, at last, Pop any large bubbles using a syringe needle, and record the absorbance at 490 nm or 492 nm within 1 hour after adding the Stop Solution. Use the corrected values in the following formula to compute percent cytotoxicity: Percent cytotoxicity=100×Experimental LDH Release (0D490)/Maximum LDH Release (0D490).

ELISA assays: Target cells were washed and suspended at $110^6$ cells/mL in x-vivo 15 medium. Of note, 100 mL each target cell type were added in triplicate to a 96-well round bottom plate (Corning). Effector T cells were washed and resuspended at 1 $10^6$ cells/mL in x-vivo15 medium and then 100 mL of T cells were combined with target cells in the indicated wells. The plates were incubated at 37° C. for 6 to 12 hours. After the incubation, supernatant was harvested and subjected to an ELISA assay (eBioscience).

All mice were euthanatized; whole blood was collected and allowed to clot for 1 h at room temperature. Sera were harvested by centrifugation at 5,000 rpm and stored frozen (−80° C.). Luminex assay for interleukin 2 (IL-2), IFN-γ, TNF-α, IL-6, and IL-10 were performed according to Luminex assay kit product instructions (R&D Systems).

Western blot: Whole cell lysates of CAR T cells were generated by lysing 5×$10^6$ washed cells in 150 µl of RIPA buffer (PBS, 1% NP40, 0.5% sodium deoxycholate, 0.1% sodium dodecyl sulfate [SDS]) with 1× Protease/Phosphatase Inhibitor Cocktail (CST) and 0.5 mM sodium vanadate (New England BioLabs), and then incubating for 30 mM on ice. Samples were sonicated at 4° C. for 5 mM to shear DNA. Western blots were then performed on supernatants of centrifuged samples, using an anti-HPK1 antibody or an anti-PD-1 antibody primary.

Example 1. Design and Synthesis of gRNA

1. Design of Guide RNA

The gRNA loaded plasmid was pUC57kan-T7-gRNA, and the gRNA targeting HPK1 was designed, and gRNA targeting PD1 was used as a control. The sequence of the gRNA specifically targeting HPK1 which is paired with the genome is GACCTGGTGGCACTGAAGA (located in the second exon of HPK1, SEQ ID NO: 1); and the sequence of the gRNA specifically targeting PD1 which is paired with the genome is

```
GGCCAGGATGGTTCTTAGGT.
(located in the first exon of PD1, SEQ ID NO: 2)

HPK1 gRNA: F:
                                       (SEQ ID NO: 3)
5'-TAGG GACCTGGTGGCACTGAAGA-3'

R:
                                       (SEQ ID NO: 4)
5'-AAAC TCTTCAGTGCCACCAGGTC-3'

PD1 gRNA: F:
                                       (SEQ ID NO: 5)
5'-TAGG GGCCAGGATGGTTCTTAGGT-3'

R:
                                       (SEQ ID NO: 6)
5'-AAAC ACCTAAGAACCATCCTGGCC-3'.
```

The gRNA coding strand and the complementary strand were synthesized, the double-stranded DNA template formed by annealing the two DNA strands of HPK1 gRNA and PD1 gRNA, which was inserted into the pUC57 plasmid vector under the control of the T7 promoter to construct pUC57kan-T7-HPK1gRNA and pUC57kan-T7-PD1gRNA, which contains T7 promoter, gRNA targeting sequence, and chimeric gRNA scaffold.

2. In Vitro Transcription of Guide RNA to Messenger RNA

The correct plasmids pUC57kan-T7-HPK1gRNA and pUC57kan-T7-PD1gRNA verified with sequencing were digested with DraI to obtain a gRNA transcription template, and then the purification of the gRNA transcription template was performed using a purification kit. The purified product was subjected to in vitro transcription of HPK1gRNA/HPK1gRNA using the T7RNAkit transcription kit (Ambion_mMESSAGE_mMA-CHINE_T7) and the transcription product was purified using a RNA purification kit (MEGAclear™ ki, Ambion). The purified gRNA was identified by agarose gel electrophoresis and the results are shown in FIG. 1. The concentration and purity of the gRNA were detected by NanoDrop 2000 ultra-micro spectrophotometer, and the gRNA was aliquoted and stored at −80° C. for use.

Additional gRNAs were designed and synthesized and purified. These gRNAs have sequence targeting the following target sequences in the HPK-1 gene:

| Target Domain Sequence | Location on human HPK-1 gene |
|---|---|
| SEQ ID NO: 11_GCTCGAGACAAGGTGTCAG | Second exon |
| SEQ ID NO: 12_AAGGTGTCAGGGGACCTGG | Second exon |
| SEQ ID NO: 13_ACCACTATGACCTGCTACAG | First exon |
| SEQ ID NO: 14_GACCTGCTACAGCGGCTGGG | First exon |
| SEQ ID NO: 15_GCTGGGTGGCGGCACGTATG | First exon |

Figure 25:
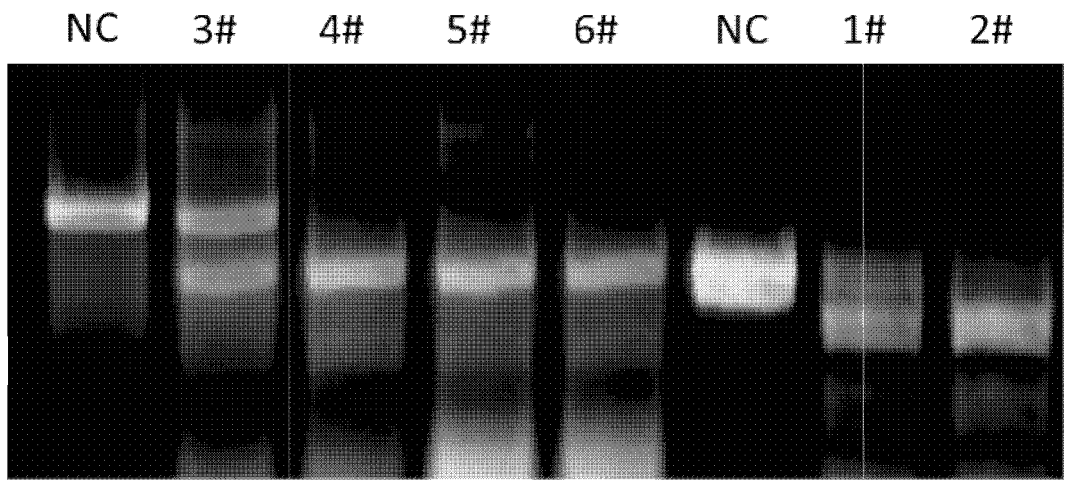
FIG. 25 shows HPK-1 knockout efficiency using various sgRNA with different targeting sequences.

These gRNAs can in some examples be used in replacement of the gRNA targeting SEQ ID NO: 1 as described above. FIG. 25 shows a representative HPK-1 gene editing efficiency using each of these gRNAs, tested by the method in Example 4. In FIG. 25, NC is control, 3 #shows results of gRNA targeting SEQ ID NO: 15; 4 #shows results of gRNA targeting SEQ ID NO: 11; 5 #shows results of gRNA targeting SEQ ID NO: 12; 6 #shows results of gRNA targeting SEQ ID NO: 1; 1 #shows results of gRNA targeting SEQ ID NO: 13; and 2 #shows results of gRNA targeting SEQ ID NO: 14.

Example 2. Recombinant Expression and Purification of Cas9 Protein

A humanized Cas9 was prepared according to literature reported procedure (sequence are provided in SEQ ID NOS: 18 and 19). Chang, N. et al., *Cell Research* 23:465-472 (2013), the content of which is incorporated by reference in its entirety, including the Sequence of the humanized, codon-optimized Cas9 cDNA and the protein sequence reported therein. Briefly, the plasmid for loading Cas9 was PGEX4T-1, and the codon-optimized full-length human cas9 cDNA was obtained by PCR. The template was plasmid PUC19-T7-CAS9. The nuclear localization signals (NLS) were added to the 5' and 3' ends of the Cas9 sequence to facilitate the nuclear import of cas9 protein.

Figure 2:
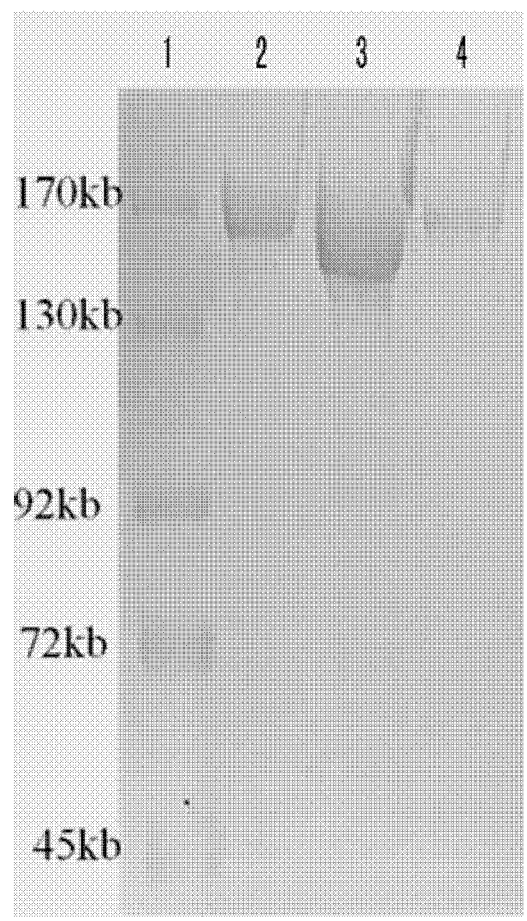
FIG. 2 shows a representative gel electrophoresis image of purified expressed recombinant Cas9 protein, from left to right: Lane 1 is a protein molecular weight marker; Lane 2 is the recombinant Cas9 protein (with GST tag) after concentration; Lane 3 is the Cas9 protein after excision of the GST tag by thrombin; Lane 4 is the recombinant Cas9 protein (with GST tag) prior to concentration.

After the plasmid was successfully constructed, the CAS9 protein was expressed by *E. coli*, purified by GST column, and the protein was concentrated and collected, and the GST tag was excised by thrombin, and a single protein band was observed around the 160 kd band (FIG. 2).

Example 3. In Vitro Expansion and Transfection of Human Peripheral Blood Mononuclear Cells Human peripheral blood mononuclear cells were extracted by centrifugation and rapid separation method using Ficoll® sodium metrizoate solution. The CD3-positive peripheral blood mononuclear cells were sorted with CD3 magnetic beads, T cells were activated with CD3/28 antibody, and the virus transfection and electroporation of the cells were performed after 2 days of culture in the LONZA-X-VIVO 15 medium containing 100 U/ml IL-2 under the condition of 37° C./5% $CO_2$.

The cas9 protein and gRNA mRNA were mixed in a certain proportion and allowed to stand at room temperature for 10 minutes, meanwhile, $4.0\times10^6$ CD3+ T cells (activated in vitro with CD3/CD28 antibody for 48 hours) were transferred to a 15 ml centrifuge tube. The cells were centrifuged at 500×g for 5 minutes, and resuspended with 400 ul opti-medium (containing the mixture of cas9 and gRNA). The cell mixture was transferred to a BTX cuvette with a gap of 4 mm, placed on ice for 10 minutes, and the cuvette was placed in a BTX Gemini X2 electroporator for electrotransformation. The electrotransformation condition is 500V and 1 ms Immediately after the end of the electroporation, the cell suspension was added to a medium (LONZA-X-VIVO 15) containing IL-2 (100 IU/ml) preheated to 37° C. 4 hours after the electrotransformation, the virus carrying human derived CD19 CAR was added with a MOI value of 10, and polybrene was added to the medium with a final concentration of 10 mg/ml. 24 hours after the virus was added, the medium was exchanged, and then cell passage was performed every other day.

Example 4. Identification of Gene Knockout Efficiency by Enzymatic Digestion (T7E1 Assay)

After 3 days of cell electrotransformation, cells were harvested and the cell genome was extracted. A DNA fragment having a mutation site (a target site of CRISPR/Cas9) was amplified by PCR. Two pairs of primers 1 # and 2 # were designed, wherein 1 #primers were used to PCR amplify the cell genome transformed with HPK1gRNA, and 2 #primers were used to PCR amplify the cell genome transformed with PD1gRNA. The two pairs of primer sequences are as follows:

```
1#: F:
                                      (SEQ ID NO: 7)
5'-agcgagagtgaggaggggg-3'

R:
                                      (SEQ ID NO: 8)
5'-ttcatcaccagagataactccc-3'

2#: F:
                                      (SEQ ID NO : 9)
5'-ccaccctctccccagtcctaccccctcctcacccctcct-3'

R:
                                      (SEQ ID NO: 10)
5'-ggtccctccagaccccctcgctccgggaccccctgggctgc-3'
```

The PCR product obtained by amplification is subjected to heat denaturation, annealing and renaturation treatment using a PCR instrument, and the setting procedure is as follows:
95° C. 3 min,
85° C. 1.5 min (temperature decrease rate 0.1° C./s),
75° C. 1.5 min (0.1° C./s),
65° C. 1.5 min (0.1° C./s)
. . . .
25° C. 1.5 min (0.1° C./s),
4° C.

Figure 3:
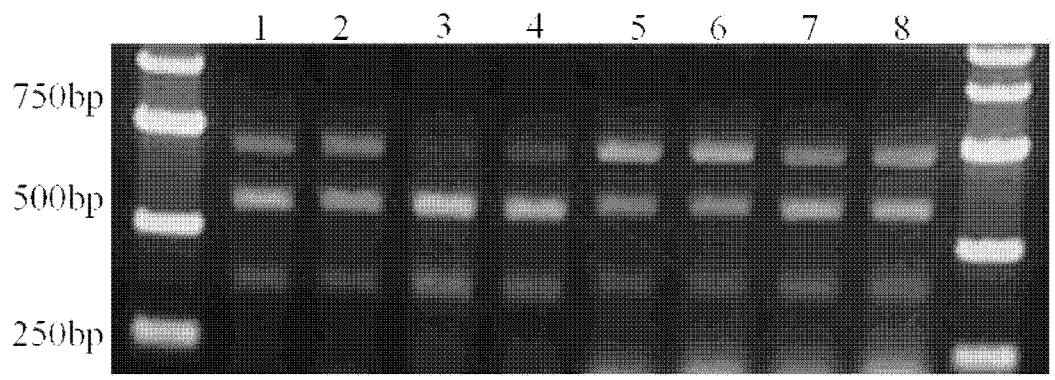
FIG. 3 presents images from agarose gel electrophoresis showing representative gene knockout efficiency under different conditions, detected by T7E1 enzymatic digestion as detailed in Example 4, from left to right: Lane 1 is $4 \times 10^6$ T cell+8 μg Cas9 protein+8 μg HPK1gRNA mRNA; Lane 2 is $4 \times 10^6$ T cell+8 μg Cas9 protein+16 μg HPK1gRNA mRNA; Lane 3 is $4 \times 10^6$ T cell+16 μg Cas9 protein+8 μg HPK1gRNA mRNA; Lane 4 is $4 \times 10^6$ T cell+16 μg Cas9 protein+16 μg HPK1gRNA mRNA; Lane 5 is $4 \times 10^6$ T cell+8 μg Cas9 protein+8 μg PD1gRNA mRNA; Lane 6 is $4 \times 10^6$ T cell+8 μg Cas9 protein+16 μg PD1gRNA mRNA; Lane 7 is $4 \times 10^6$ T cell+16 μg Cas9 protein+8 μg PD1gRNA mRNA; Lane 8 is $4 \times 10^6$ T cell+16 μg Cas9 protein+16 μg PD1gRNA mRNA.

The treated PCR product mixture was added with T7 endonuclease 1 (NEB), left at 37° C. for 15 minutes, and subjected to agarose gel electrophoresis (2% agarose gel) to determine the digestion efficiency. The results are shown in FIG. 3.

Figure 4:
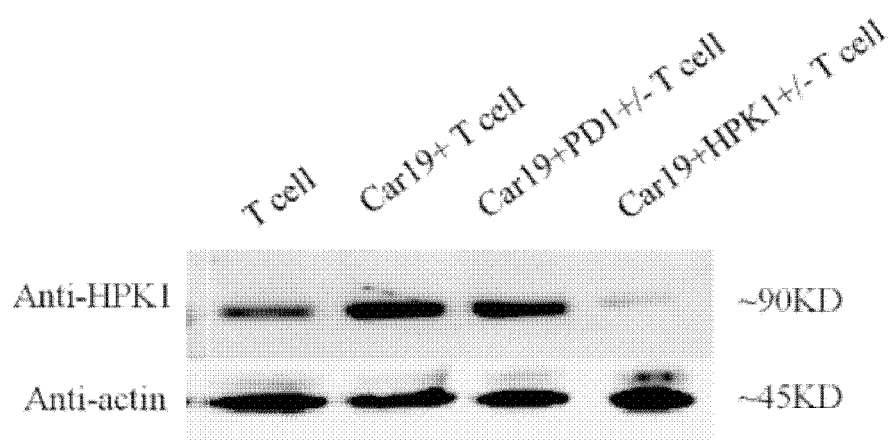
FIG. 4 presents Western Blot images showing representative gene knockout efficiency. The results show that the expression level of HPK1 in CAR19+HPK1+/− T cell is significantly reduced than the other three groups. β-actin was used as an internal reference.

Example 5. Identification of Gene Knockout Efficiency by Western Blot Method 3 days after the cells were electrotransformed, the cells were collected, the cell proteins were extracted, and the expressions of HPK1 and β-Actin were detected by Western blot. The results are shown in FIG. 4. The specific groupings are shown in the following table:

|  | T cell | CD19 + T cell | HPK1−/− CD19 + T cell | PD1−/− CD19 + T cell |
|---|---|---|---|---|
| gRNA | − | − | HPK1gRNA (1#gRNA) | PD1gRNA (2#gRNA) |
| Cas9 Protein | − | − | + | + |
| CD19 Car virus | − | + | + | + |

The in vitro expansion, electrotransformation and viral transfection steps of human peripheral blood mononuclear cells are detailed in Example 3.

Figure 26:
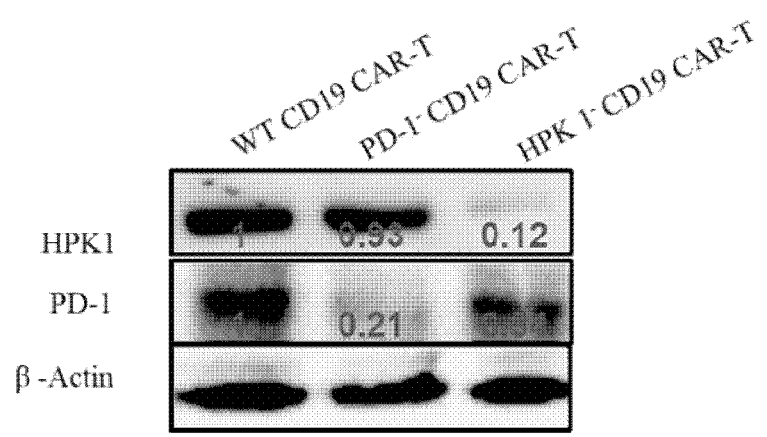
FIG. 26 shows a representative quantification of knockout efficiency measured by Western Blot.

FIG. 4 shows that the expression level of HPK1 in CAR19+HPK1+/− T cells is significantly reduced compared to T cells, CAR19+ T cells and CAR19+PD+/− T cells. FIG. 26 shows a representative quantification of the knockout efficiency measured by Western Blot.

Figure 5:
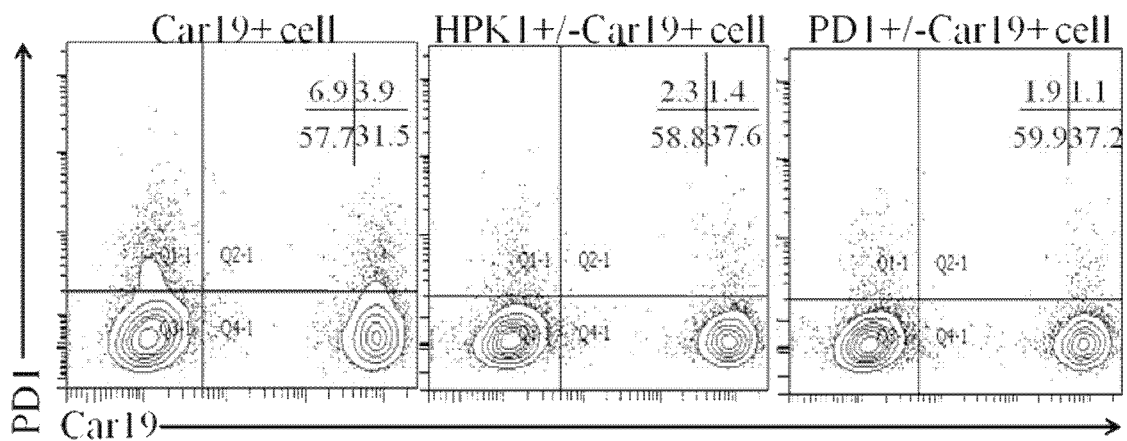
FIG. 5 shows flow cytometry results detecting surface markers CAR19 and PD1 receptor for CD19+ cells, CAR19+HPK1+/− T cells and CAR19+PD1+/− T cell. The images show that PD1 receptor on the surface of CAR19+ HPK1+/− T cell is significantly reduced compared to control CAR19+ T cell. The expression level of the PD1 receptor on the surface of CAR19+HPK1+/− T cell is close to that of CAR19+PD1+/− T cell.

Example 6. Detection of the Transfection Efficiency of CAR19 and the Expression of PD1 by Flow Cytometry 7 days after the cells were transfected with virus, $1\times10^6$ cells were taken from each group, and the expressions of Car and HPK1 were detected after incubating with the antibody at 4° C. protected from light. The results are shown in FIG. 5. The specific groupings are shown in the following table:

|  | T cell | CD19 + T cell | HPK1−/− CD19 + T cell | PD1−/− CD19 + T cell |
|---|---|---|---|---|
| gRNA | − | − | HPK1gRNA (1#gRNA) | PD1gRNA (2#gRNA) |
| Cas9 Protein | − | − | + | + |
| CD19 Car virus | − | + | + | + |

The in vitro expansion, electrotransformation and viral transfection steps of human peripheral blood mononuclear cells are detailed in Example 3.

FIG. 5 shows that the expressions of PD1 receptor on the surface of CAR19+HPK1+/− T cells and CAR19+PD1+/− T cells were significantly reduced than that of the simple CAR19 T cell. The levels of PD1 receptor expression on the surface of CAR19+HPK1+/− T cells and CAR19+PD1+/− T cells were similar, with no significant difference.

Example 7. T Cell Killing Experiment

The effector cells are CD3+ human T cells transfected by the above electrotransformation and virus transfection, and the target cells are Raji, Daudi, K562 human malignant lymphoma cell lines, respectively. 100 µl of the target cells were plated into 96-well plates, and after 24 hours, 100 µl of effector cells (1×10$^6$ cells/ml) were added, and 3 replicate wells were made for each sample. The supernatant was collected by incubating the cells for 12 h in a $CO_2$ incubator at 37° C. with a volume fraction of 5%. The lactate dehydrogenase (LDH) content in the cell supernatant was measured using a promega CytoTox 96® Non-Radioactive Cell Killing Test Kit. After shaking for 5 minutes on the microoscillator, it was detected by a microplate reader at a wavelength of 490 nm, and the cell killing function was calculated according to the following formula:

$$\% \text{ Cytotoxicity} = \frac{\text{Experimental} - \text{Effector Spontaneous} - \text{Target Spontaneous} \times 100}{\text{Target Maximum} - \text{Target Spontaneous}}$$

The specific groupings are shown in the following table:

|  | T cell | CD19 + T cell | HPK1−/− CD19 + T cell | PD1−/− CD19 + T cell |
|---|---|---|---|---|
| gRNA | − | − | HPK1gRNA (1#gRNA) | PD1gRNA (2#gRNA) |
| Cas9 Protein | − | − | + | + |
| CD19 Car virus | − | + | + | + |

The in vitro expansion, electrotransformation and viral transfection steps of human peripheral blood mononuclear cells are detailed in Example 3.

Figure 6:
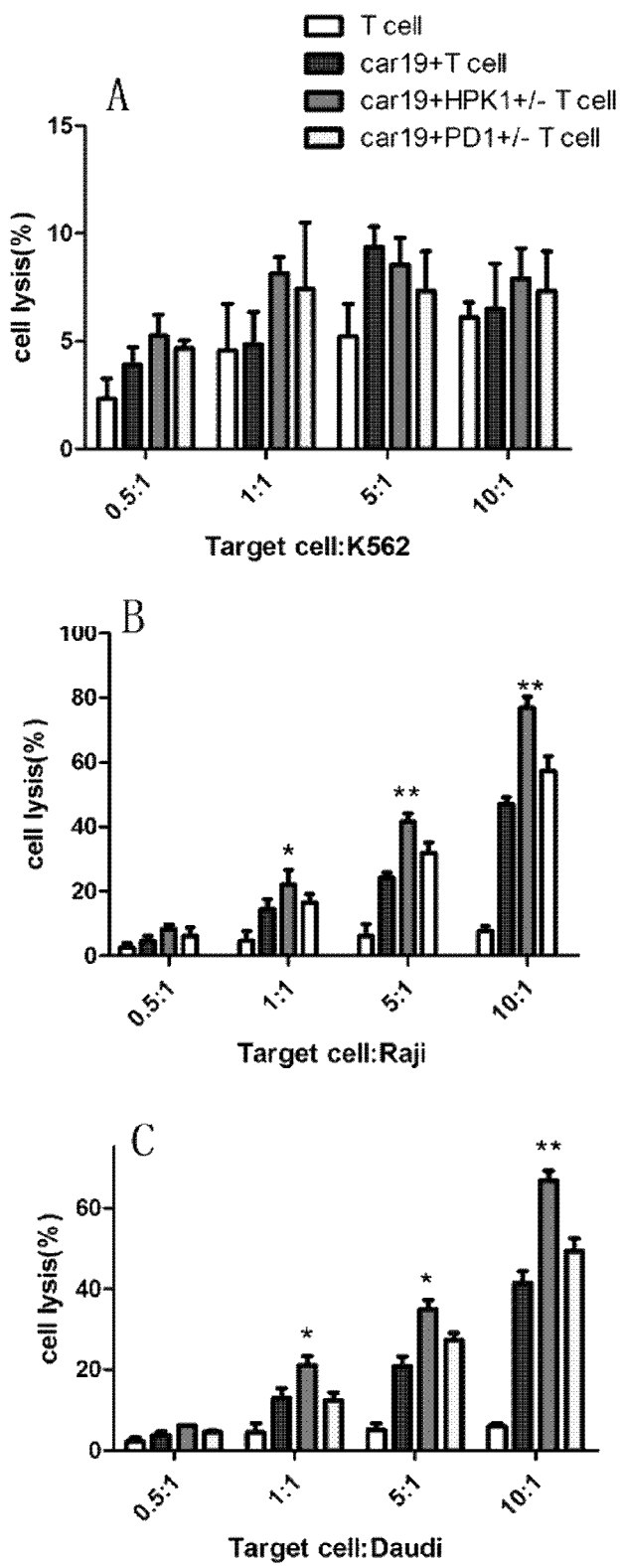
FIGS. 6A-6C presents bar graphs comparing T cell killing activity of different cell compositions: T cells, CD19+ T cells, CAR19+HPK1+/− T cells and CAR19+PD1+/− T cell.

The killing effects of T cells on three human malignant lymphoma cell lines are shown in FIG. 6. In FIG. 6, CAR19+HPK1+/− T cells have the best killing effect on three human malignant lymphoma cell lines with almost all effector to target ratios (except for the K562 cell line with an effector to target ratio of 5:1). For both Raji and Daudi cell lines, at the effector to target ratios of 1:1 and 5:1, the killing effect of CAR19+HPK1+/− T cells is significantly different from those of other groups; and at the effector to target ratio of 10:1, the killing effect of CAR19+HPK1+/− T cells is extremely significant different compared with those of other groups.

Example 8. Detection of Secreted Cytokines by T Cells

CAR19+CD3+ human T cells and three target cells (Raji, Daudi, K562) were co-cultured for 12 hours at a ratio of 2:1, and then the supernatant was collected, and the contents of IFN-γ and IL-2 in the supernatant were detected using the Elisa detection kit of eBIOSCIENCE respectively. The results are shown in FIG. 7.

Figure 7:
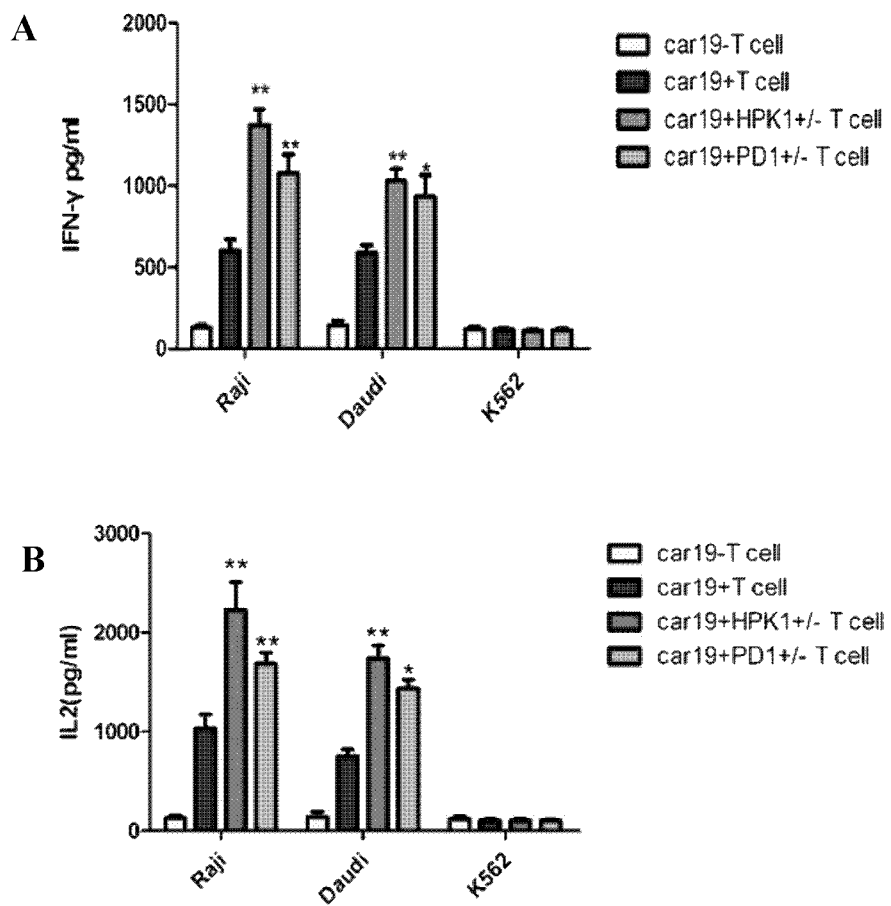
FIGS. 7A and 7B presents bar graphs comparing cytokine product level of different cell compositions: T cells (CD19− T cells), CD19+ T cells, CAR19+HPK1+/− T cells and CAR19+PD1+/− T cell.

In FIG. 7, the killing effect of CAR19+HPK1+/− T cells on Raji and Daudi is higher than those of the other groups. The killing effects of CAR19+HPK1+/− T cells and CAR19+PD1+/− T cells on Raji are extremely significantly different from those of the other groups. The killing effect of CAR19+HPK1+/− T cells on Daudi is extremely significantly different from those of the other groups, and the killing effect of CAR19+PD1+/− T cells on Daudi is significantly different from those of the other groups.

Example 9. Effect of T Cells on a Mouse Model of Human Lymphoma

Test animals: female NOD SCID mice. All mice were housed according to the guidelines of the Tsinghua University laboratory animal research center and Animal Care and Use Committee. All animals were maintained in pathogen-free conditions and cared for in accordance with the International Association for Assessment and Accreditation of Laboratory Animal Care policies and certification.

Figure 12:
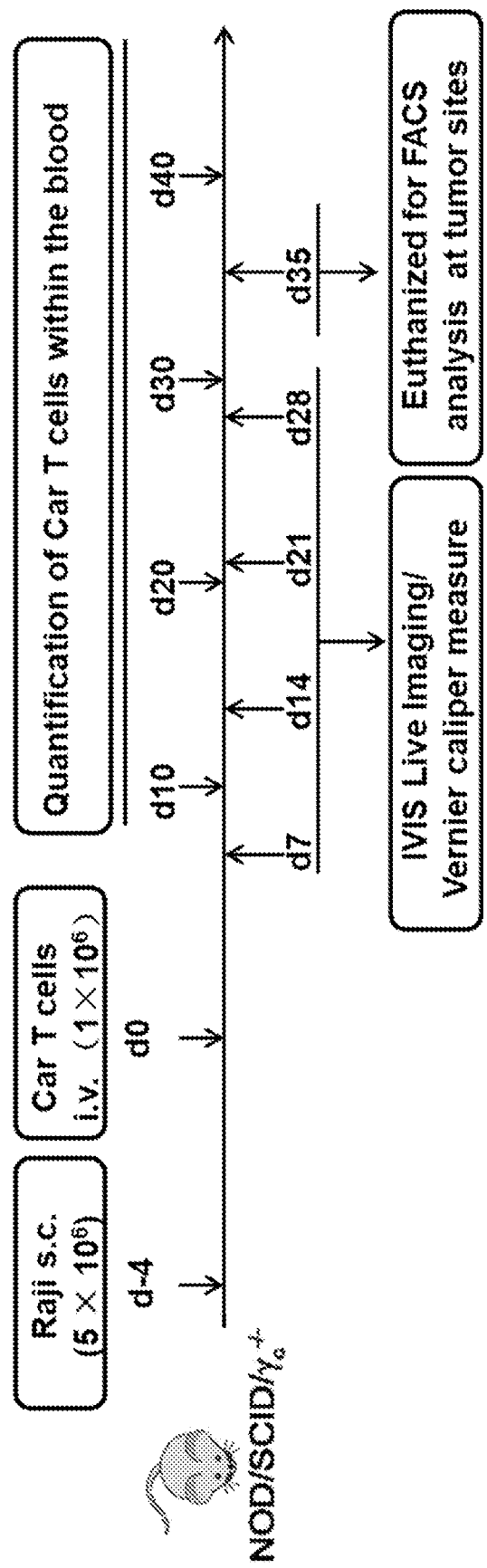
FIG. 12 shows a general flowchart of animal studies.
Figure 13A:
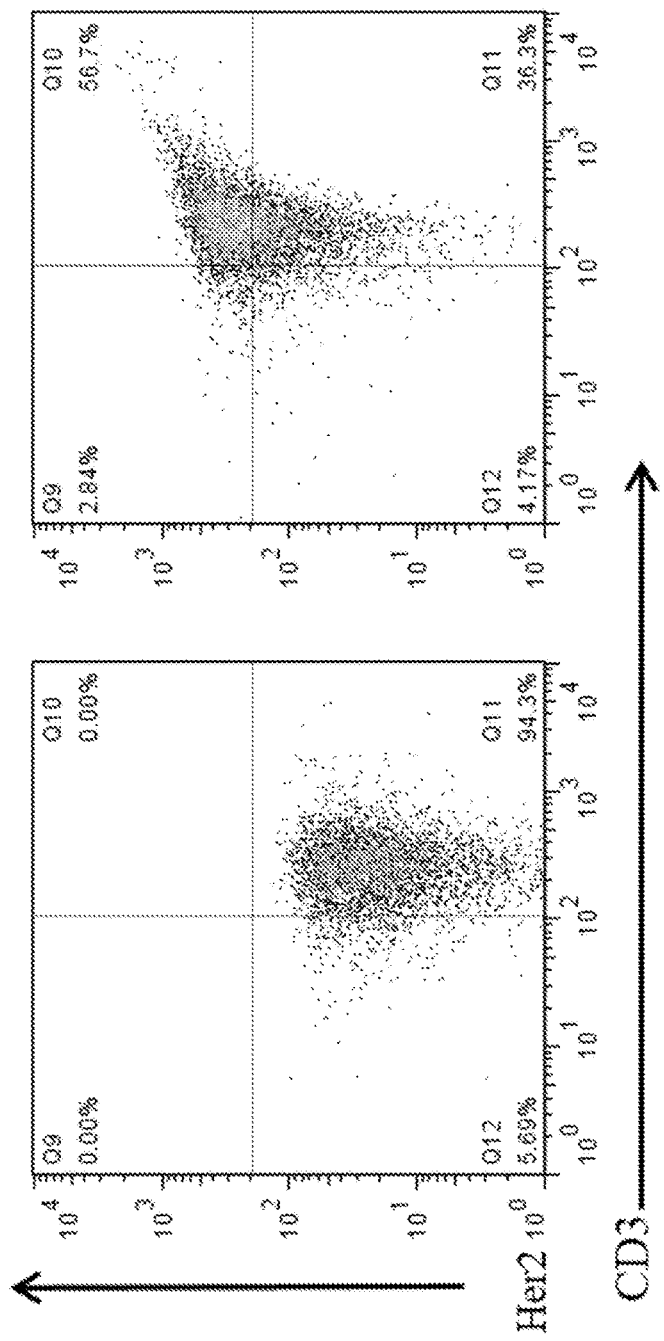
FIGS. 13A-13D shows her2 CAR T cell exhaustion during ex vivo expansion. A. Her2 Car expression on T cell; B. Western blot evaluating the expression of HPK1 on T cell from day 0 naive T cell to day 10 after initial activation, and Her2 CAR was transduced on day 3; C. Facs evaluating the expression of HPK1 on T cell from day 0 naive T cell to day 10 after initial activation, and Her2 CAR was transduced on day 3; D. Fluorescence microscopy of HPK1 expression (red) in different Her2 Car T cells (PD1 expression high and low)
Figure 13B:
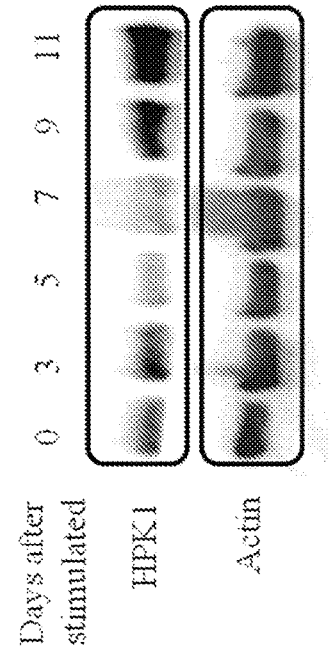
Figure 13C:
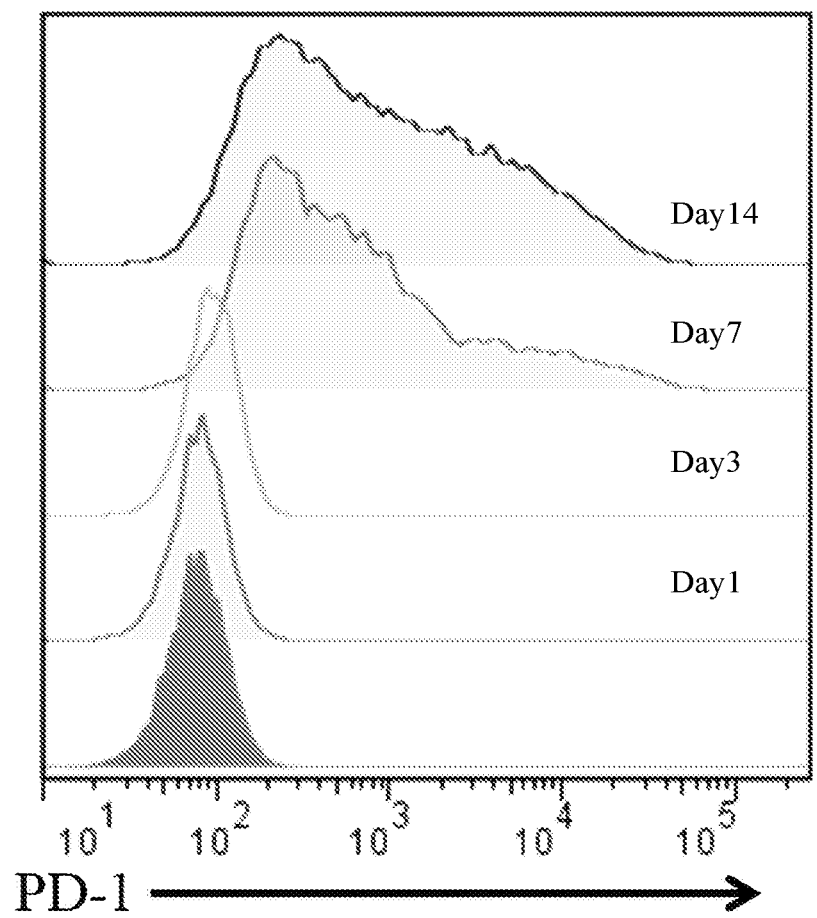
Figure 13D:
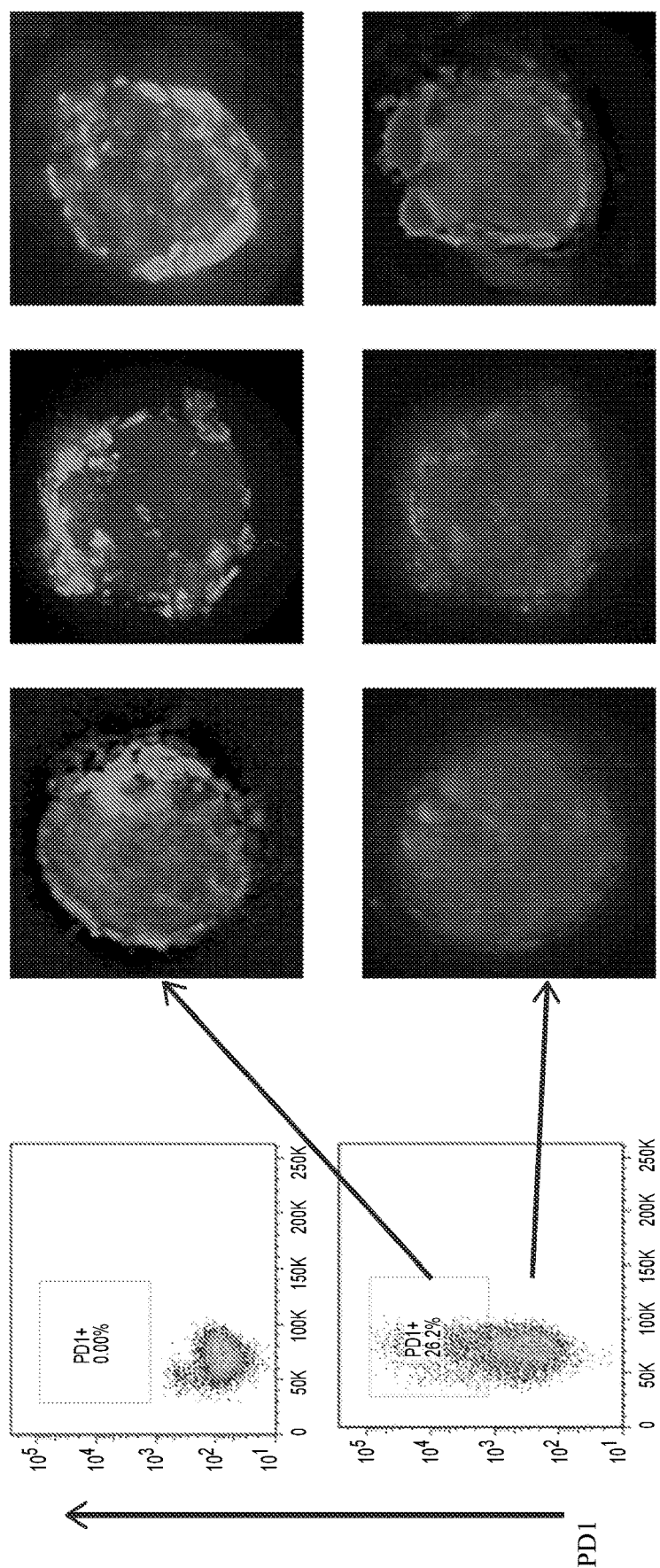

Test method: FIG. 12 shows a general schedule of in vivo animal studies. Briefly, 6- to 10-week old NOD-SCIDg/ (NSG) mice were injected subcutaneously with 1×10$^6$ Raji tumors cells on the right flank at day 0. The mice were treated with 1×10$^6$ T cells or CD19 CAR-T cell via the tail vein at day 4 post Raji tumor inoculation such that both tumors were approximately 100 mm$^3$ in volume. Tumors were measured every 7 days. Mice that had no visible or palpable tumors that could be measured on consecutive measurement days were considered as "complete regressions". Animals were euthanized if they exhibited signs of distress or when the total tumor size reached 2,500 mm$^3$.

40 female NOD SCID mice were randomly divided into 6 groups, 8 mice in each group. Each group of mice were inoculated with Raji cells by subcutaneous injection to construct a mouse model of human lymphoma. The Ctrol group was a blank control group, and 200 µL of physiological saline was used instead of the administered cells. The T cell treatment group was a negative control group, and the administered cells were 1×10$^6$ T cells. The cells for administering to the Car-T WT treatment group were 1×10$^6$ CAR-T cells. The cells for administering to the Car-T HPK1 KO treatment group were 1×10$^6$ HPK1−/− CAR-T cells. The cells for administering to the Car-T PD1 KO treatment group were 1×10$^6$ PD1−/− CAR-T cells. Each group of mice were administered in a single dose.

(1) Measurement of Tumor Volume

The tumor volumes of the mice were measured before administration, and the long diameter and short diameter of the mice tumors were measured twice a week after administration, whereby the tumor volumes were calculated and recorded. The tumor volume can reflect the proliferation of tumor in mice. The long diameter and short diameter of the tumor were measured with a vernier caliper: tumor volume ($mm^3$)=tumor long diameter (mm)×tumor short diameter$^2$ ($mm^2$)×0.5. The differences among the various dose groups and the differences between each dose group and the negative control group were compared.

(2) In Vivo Imaging Detection

The mice were subjected to in vivo imaging detection. The mice were shaved before the detection, and anesthetized with intraperitoneal injection of pentobarbital sodium solution (15 μg/g body weight). Each group of mice were intraperitoneally injected with 200 μl of 15 g/L fluorescein solution and 5 minutes later, in vivo imaging observation was performed.

(3) CAR-T Proliferation Assay

The peripheral blood of the mice was taken before administration, and the percentage of CD3 positive cells in the peripheral blood of the mice was measured, and the peripheral blood of the mice was taken every 10 days after administration to determine CD3 positive cells in the peripheral blood of the mice. The amount of CD3 positive cells reflects the proliferation of CAR-T cells in peripheral blood of mice. The percentage of CD3 positive cells in peripheral blood of mice was determined by flow cytometry. The tail vein of the mouse was cut with a surgical blade to collect blood and about 100 μL of peripheral blood was collected in a 1.5 mL EP tube containing 20 μL of 0.5 M EDTA anticoagulant solution. After thoroughly mixing, 100 μL of PBS was added and centrifuged at 400 g for 5 min, the supernatant was discarded, the pellet was resuspended with 1 mL of red blood cell lysate, and placed in a refrigerator at 4° C. for 15 min to fully lyse the red blood cells. After centrifugation at 400 g for 5 min, the supernatant was discarded, and the pellet was washed twice with 200 μL of PBS, resuspended in 200 μL of PBS, thoroughly mixed, and then detected by flow cytometry. The differences among the various dose groups and the differences between each dose group and the negative control group were compared.

(4) Determination of CAR-T Cells' Phenotype of Infiltrating Tumor Tissue

The expression of PD1/Tim3/Lag3/CD107a/AnnexinV on car-t cells infiltrating in tumor tissue was detected by flow cytometry on day 28 after the tumor inoculation.

Test Results (1) Measurement of Tumor Volume

Figure 8:
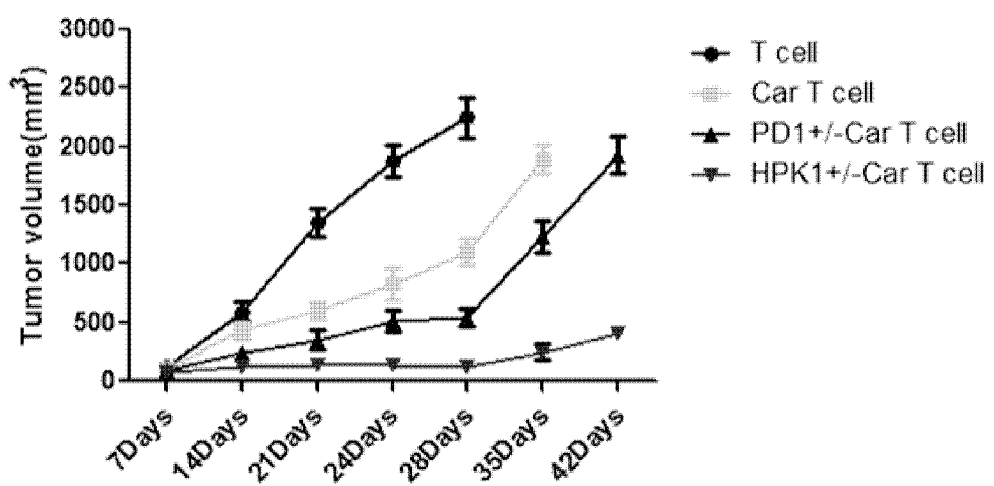
FIG. 8 presents a graph showing comparison of tumor volume in mice among different treatment groups: T cell treatment group, Car-T WT treatment group, Car-T HPK1 KO treatment group, and Car-T PD1 KO treatment group. (n=6 mice per group). ***P<0.001, unpaired t test.

FIG. 8 shows the tumor volumes of each group of mice. As shown in FIG. 8, the tumor volumes of the Car-T WT treatment group, the Car-T HPK1 KO treatment group, and the Car-T PD1 KO treatment group are all reduced compared with that of the T cell treatment group, while the tumor volume of the mice in the Car-T HPK1 KO treatment group is the smallest.

(2) In Vivo Imaging Detection

Figure 9:
FIG. 9 presents images of mice treated with T cells, Car-T WT, Car-T HPK1 KO, and Car-T PD1 KO.

FIG. 9 shows the in vivo imaging results of each group of mice. It can be seen from FIG. 9 that, the therapeutic effects of the Car-T WT treatment group, the Car-T HPK1 KO treatment group, and the Car-T PD1 KO treatment group are all better compared with that of the T cell treatment group, while the therapeutic effect of the mice in the Car-T HPK1 KO treatment group is the best.

(3) CAR-T Proliferation Assay

Figure 10:
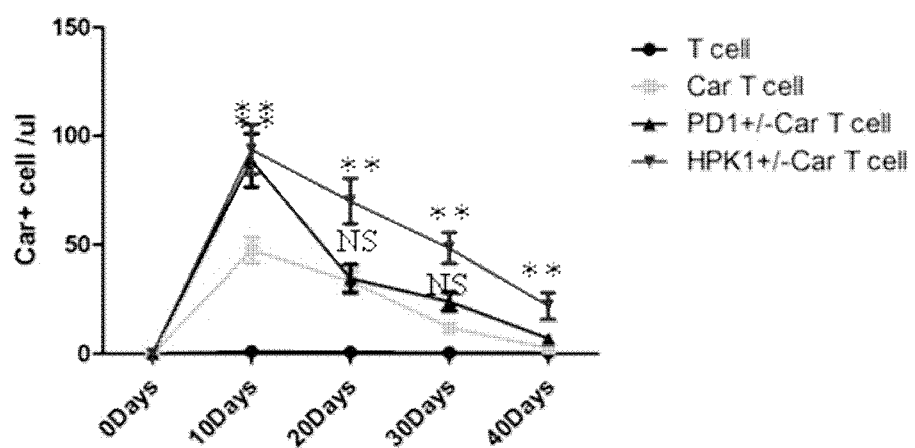
FIG. 10 presents a graph showing the persistence of T cells, Car-T WT, Car-T HPK1 KO, and Car-T PD1 KO cells in mice post-treatment over a period of 40 days. Quantification of T cells within the blood was conducted after adoptive T cell transfer into mice. n=3 mice per group. *P<0.05, **P<0.01 by unpaired t test. Bar graphs and scatter plots represent mean±s.e.m.

FIG. 10 shows the percentages of CD19CART cells in peripheral blood of mice after administration of mice in each group. As shown in FIG. 10, the percentages of peripheral blood CART cells in the Car-T WT treatment group, the Car-T HPK1 KO treatment group, the Car-T PD1 KO treatment group are all greater than that in the T cell treatment group, indicating that the Car-T cells proliferate in mice. However, as shown in FIG. 10, on day 10, the numbers of the Car-T cells in the T PD1 KO and Car-T HPK1 KO treatment groups are significantly higher than that in the Car-T WT treatment group. After 20, 30, and 40 days of treatment, the numbers of the Car-T cells in the peripheral blood of the mice in the Car-T WT treatment group and the Car-T PD1 KO treatment group are significantly decreased compared with that of 10 days after treatment. Although the number of cells in the Car-T HPK1 KO treatment group is down-regulated, it is significantly higher than those of the Car-T WT treatment group and the Car-T PD1 KO treatment group.

(4) Detection of CAR-T Cell Phenotype and Function

Figure 11A:
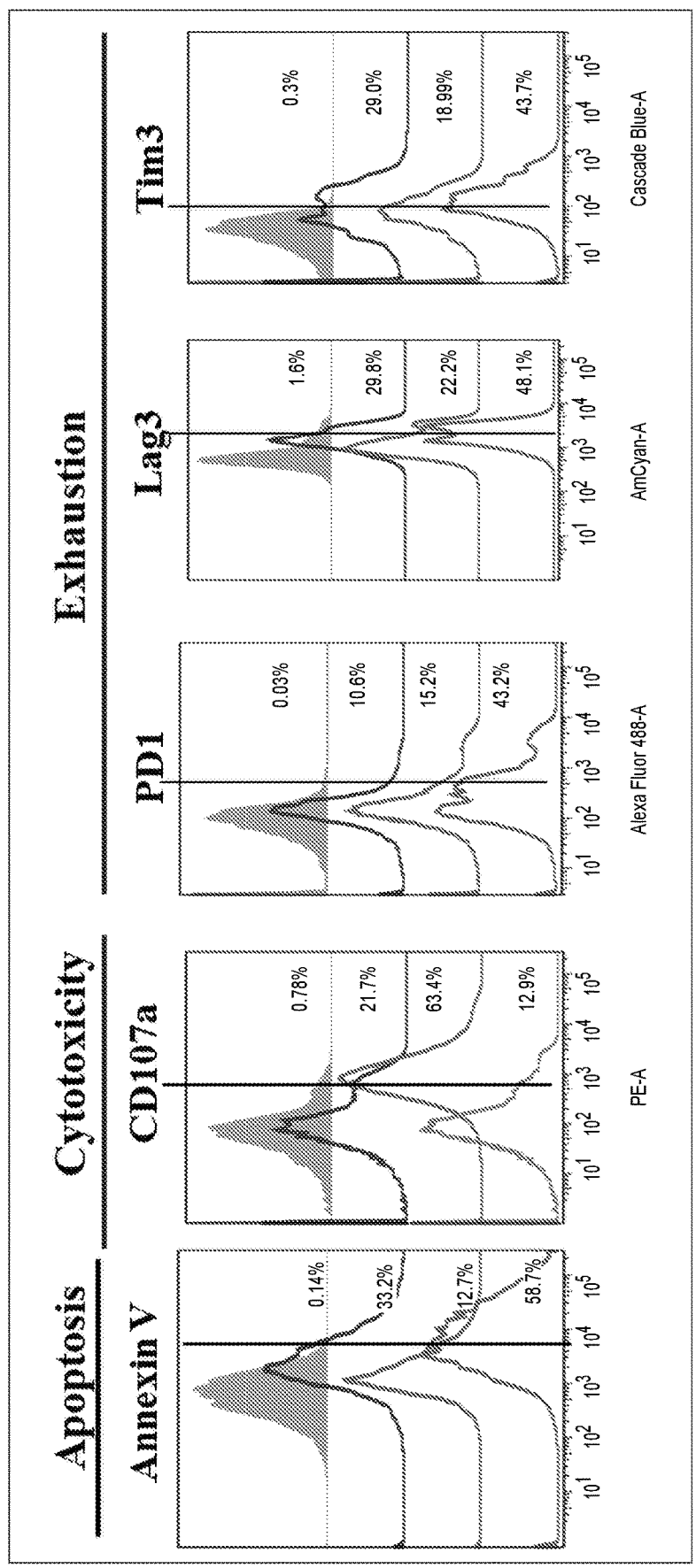
FIGS. 11A-11C present representative assessment of expression levels of various surface markers, Annexin V/CD107a/PD1/Tim3/Lag3 for cells infiltrating in mice tumor tissues of each of the groups, T cells, Car-T WT, Car-T HPK1 KO, and Car-T PD1 KO cells. The figures assess apoptosis, cytotoxicity and Exhaustion marker expression of CAR T cells from on day 14 after adoptive transfer.
Figure 11B:
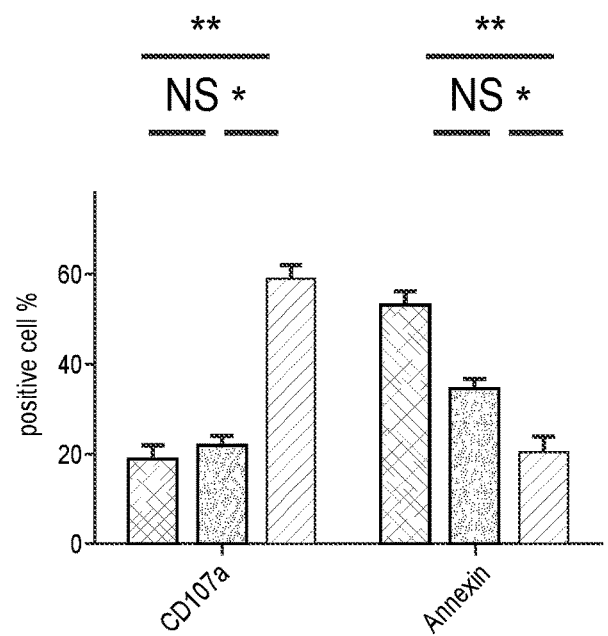
Figure 11C:
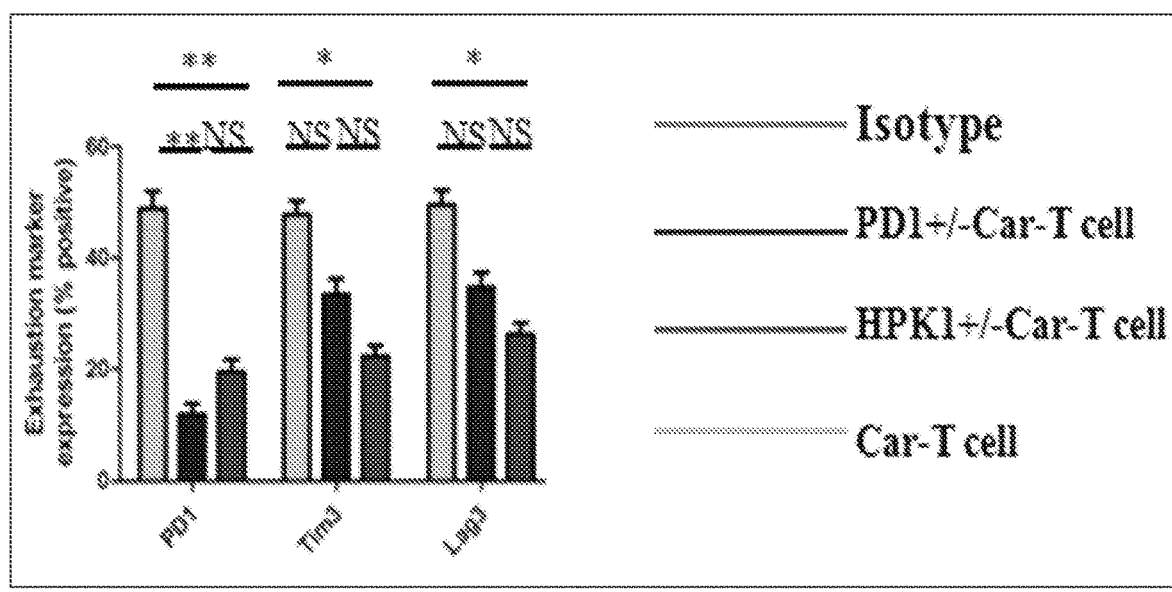

FIG. 11 shows the phenotype of Car-T cells in tumor of mice 28 days after administration in each group of mice. As shown in FIG. 10, in T cell apoptosis and cell killing experiments, compared with the Car-T WT treatment group, the Car-T HPK1 KO treatment group exhibits less apoptosis and enhanced killing function, while the Car-T PD1 KO treatment group has no significant difference compared with the Car-T WT treatment group. The surface marker molecule PD1/Tim3/Lag3 of T cell depletion is significantly down-regulated in the Car-T HPK1 KO treatment group compared with the Car-T WT treatment group, while only PD1 in the Car-T PD1 KO treatment group is significantly decreased compared with the Car-T WT treatment group, and there is no significant difference for the others.

Example 10. HPK-1 Gene Knockout in Her2 Car T Cells

Her2 CAR T cells also experience exhaustion during an ex vivo expansion study. See FIGS. 13A-13D. This Example shows the effect of HPK-1 gene knockout on Her2 CAR T cells.

The preparation of Her2 CAR T cells with HPK-1 gene knockout followed the procedure described in the General Methods and Material section described herein. The gRNA used for this knockout comprises a sequence targeting the target domain of HPK-1 gene (with SEQ ID NO: 1). The Cas9 protein was prepared and isolated following the procedure described in Example 2. PD-1 knockout Her2 CAR T cells were prepared using the same gRNA shown in Example 1 and used as control. The Her2 CAR T cells express HER2-CARs containing a 4-1BB/CD3 signaling module. Cell expansion follows similar procedure as described in Example 3.

Figure 14A:
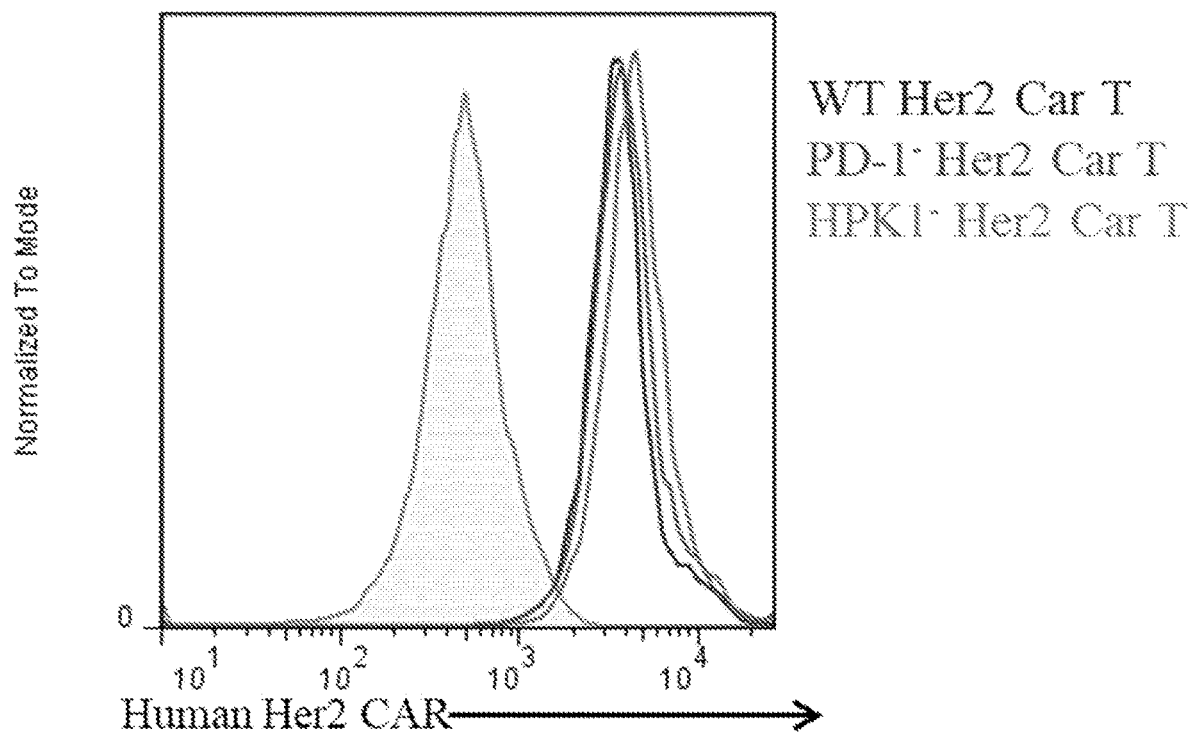
FIGS. 14 A-C present graphs and images showing the cleavage efficacy of HPK1 using sgRNA with Cas9 protein. A. FACS analysis of Her2 Car expression in T cells (day 3 after transduction; B. Western blot evaluating the expression of HPK1 after CRISPR/Cas9-targeted HPK1 or PD-1; C. FACS analysis of the expression of PD-1 after CRISPR/Cas9-targeted HPK1 or PD-1.
Figure 14B:
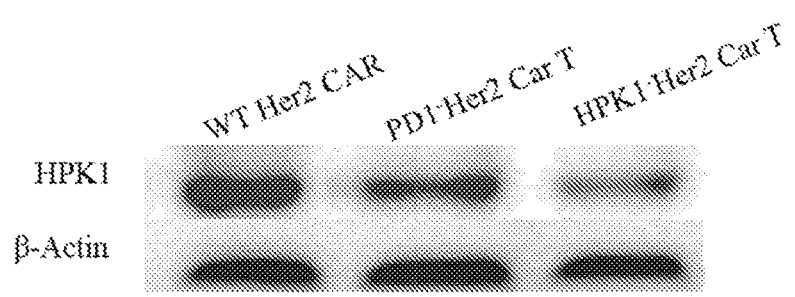
Figure 14C:
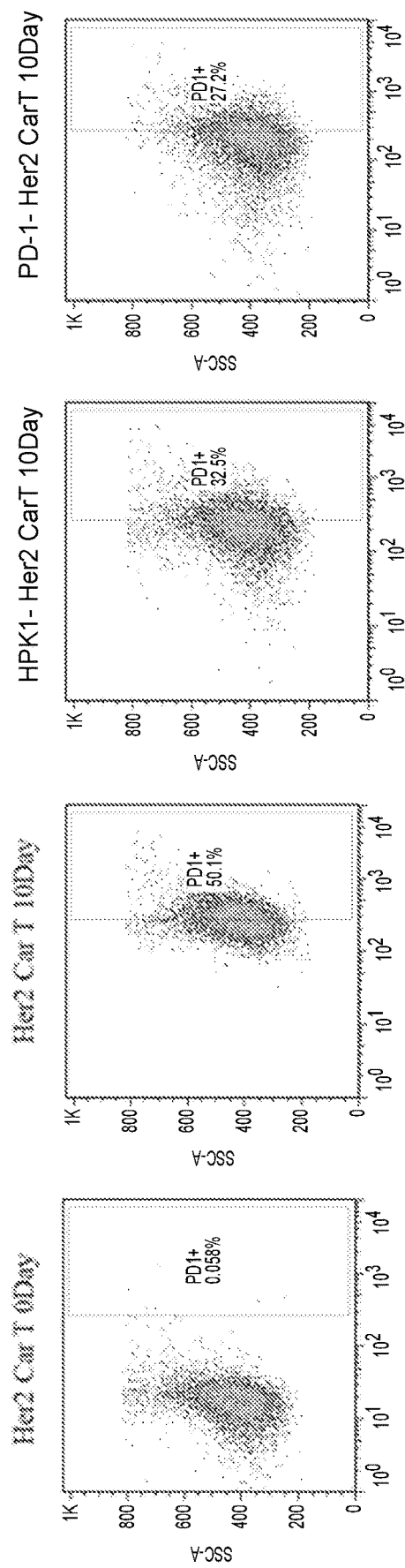

HPK-1 knockout efficiency was assessed following the same procedure described in Example 5 by Western Blot and Her2 Car expression was evaluated by FACS. As shown in FIGS. 14A-C, HPK-1 knockout does not affect the transduction and expression of Her2 CAR on the T cells. FIG. 14B also shows that the gRNA/Cas9 was effective in knocking out HPK1 gene in Her2 Car T cells. Similar to those observed in the CD19 CAR T cells, knocking out HPK1 gene also significantly reduced the expression of PD1 on the T cell surface, and is substantially the same as the PD-1 knockout CAR T cells.

Example 11. In Vivo Efficacy of HPK-1 Gene Knockout Her2 Car T Cells

This example studies the in vivo behavior of HPK-1 knockout Her2 CAR T cells.

NSG mouse of 6- to 10-week old of age were inoculated i.p. with 5×106 SKOV-3 tumor cells at day 0. The mice were treated with 1×10$^6$ T cells or Her2 CAR-T cell via the tail vein at day 10 post SKOV-3 tumor inoculation such that both tumors were approximately 100 mm$^3$ in volume. Tumors were measured every 3-4 days. Mice that had no visible or palpable tumors that could be measured on consecutive measurement days were considered as "complete regressions". Animals were euthanized if they exhibited signs of distress or when the total tumor size reached 2,500 mm$^3$.

Figure 15:
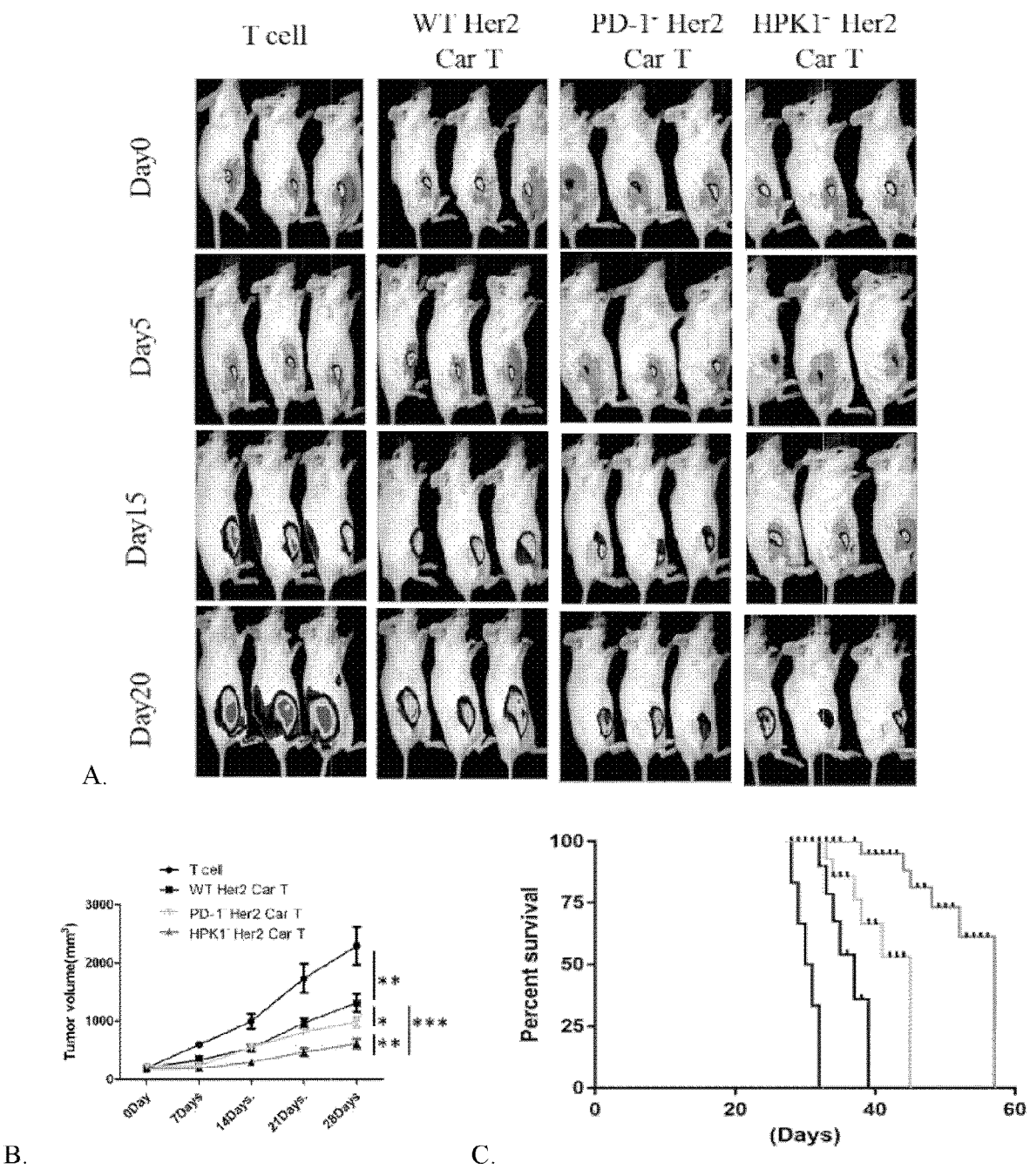
FIGS. 15A-C present images and graphs showing the enhanced in vivo efficacy of Her2 CAR T cells with HPK-1 gene knockout.
Figure 16:
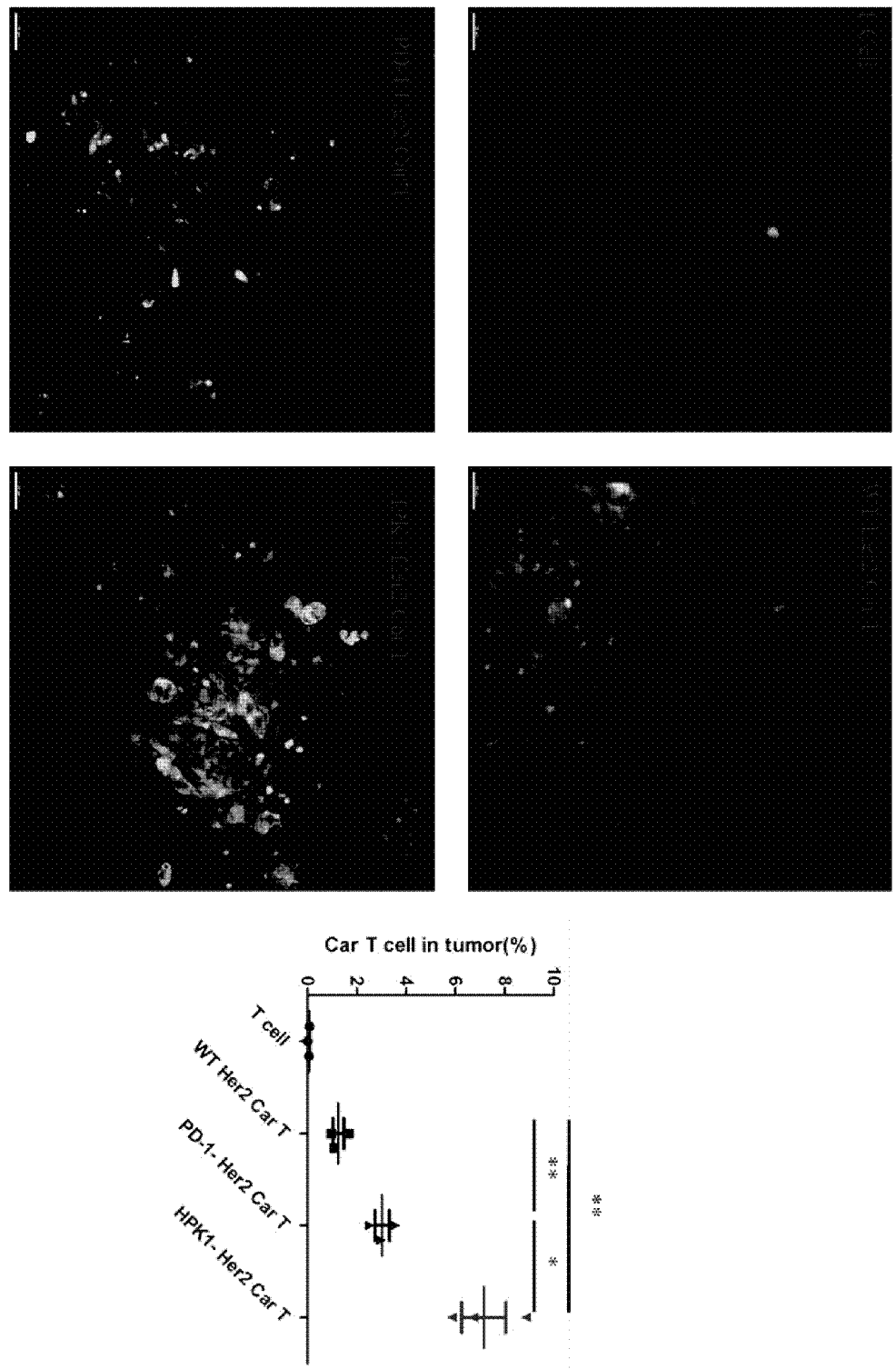
FIG. 16 presents images and graphs showing that HPK-1 knockout enhances infiltration of CAR T cells in tumor. On day 10 after treated with $1 \times 10^6$ T cells expressing HER2-CARs, tumor tissues were resected from the mice, and each tissue was used for immunohistochemistry (IHC). In IHC analysis, combinations of anti-CD3 antibody was used for primary staining. Nuclei were stained with DAPI (blue). Microscopic examination of IHC samples were conducted at ×100 magnification. Car T cells in tumor were quantified and the graph in FIG. 16 also shows CAR-T cells to tumour ratio. **P<0.01, *P<0.05 unpaired t test.
Figure 17A:
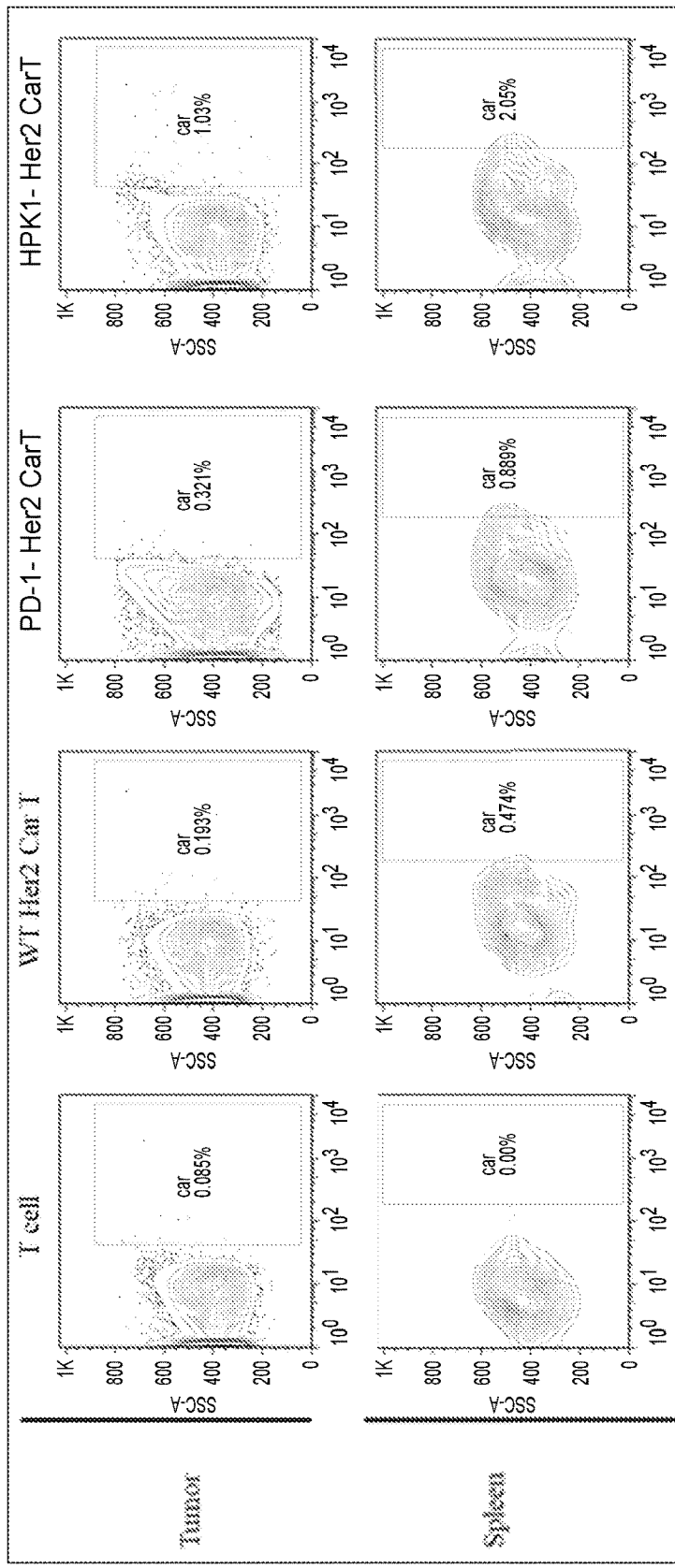
FIGS. 17A-C present images and graphs showing that HPK-1 knockout enhances infiltration of CAR T cells in spleen. Tumor-infiltrating Her2 Car-t cell and spleen Her2 Car-t cell were analyzed at 25 days after treated with $1 \times 10^6$ T cells expressing HER2-CARs. *P<0.05, P<0.01, *P<0.001 by unpaired t test.
Figure 17C:
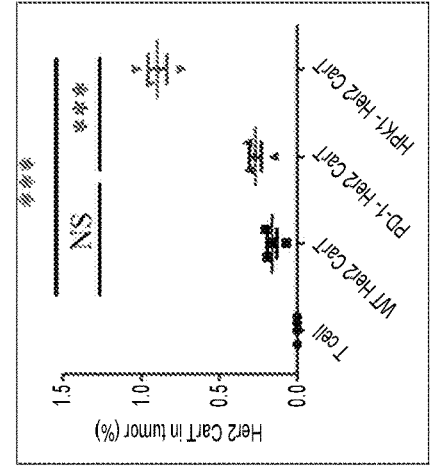
Figure 17B:
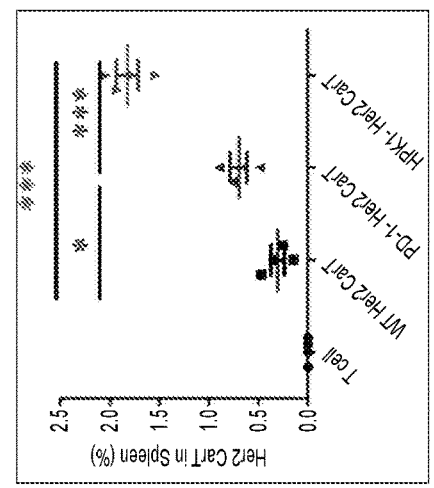
Figure 18:
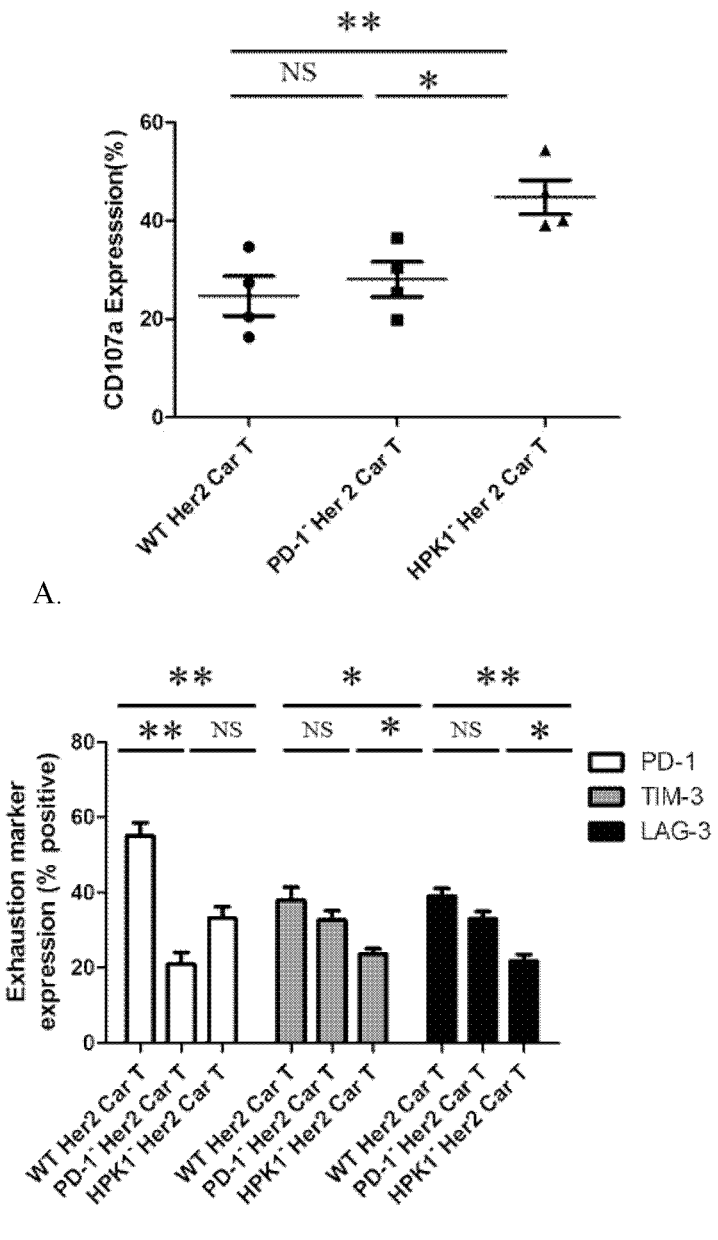

The results were shown in FIGS. 15-18. As shown in FIG. 15, HPK1 knockout significantly enhances the efficacy of Her2 CAR T cells in this tumor model. Mice treated with HPK1$^-$Her2 Car T cells experiences the lowest tumor growth over the period of 28 days and also significantly prolonged survival of mice. On the other hand, the improvement of PD1– Her2 Car T cells over wild type Her2 Car T cells was less significant. Further studies also show that HPK1 knockout enhances the ability of Her2 Car T cells to infiltrate tumors (see FIG. 16) and spleen (see FIG. 17).

Similar to the in vitro exhaustion marker studies observed for CD19 Car T cells, it was also found that HPK1 knockout ameliorate exhaustion of Her2 Car T cells in vivo. See FIG. 18.

Example 12. HPK-1 Gene Knockout in BCMA Car T Cells

This Example studies HPK-1 gene knockout on BCMA CAR T cells.

The preparation of BCMA CAR T cells with HPK-1 gene knockout followed the procedure described in the General Methods and Material section described herein. The gRNA used for this knockout comprises a sequence targeting the target domain of HPK-1 gene (with SEQ ID NO: 1). The Cas9 protein was prepared and isolated following the procedure described in Example 2. PD-1 knockout BCMA CAR T cells were prepared using the same gRNA shown in Example 1 and used as control. Cell expansion follows similar procedure as described in Example 3.

Figure 19A:
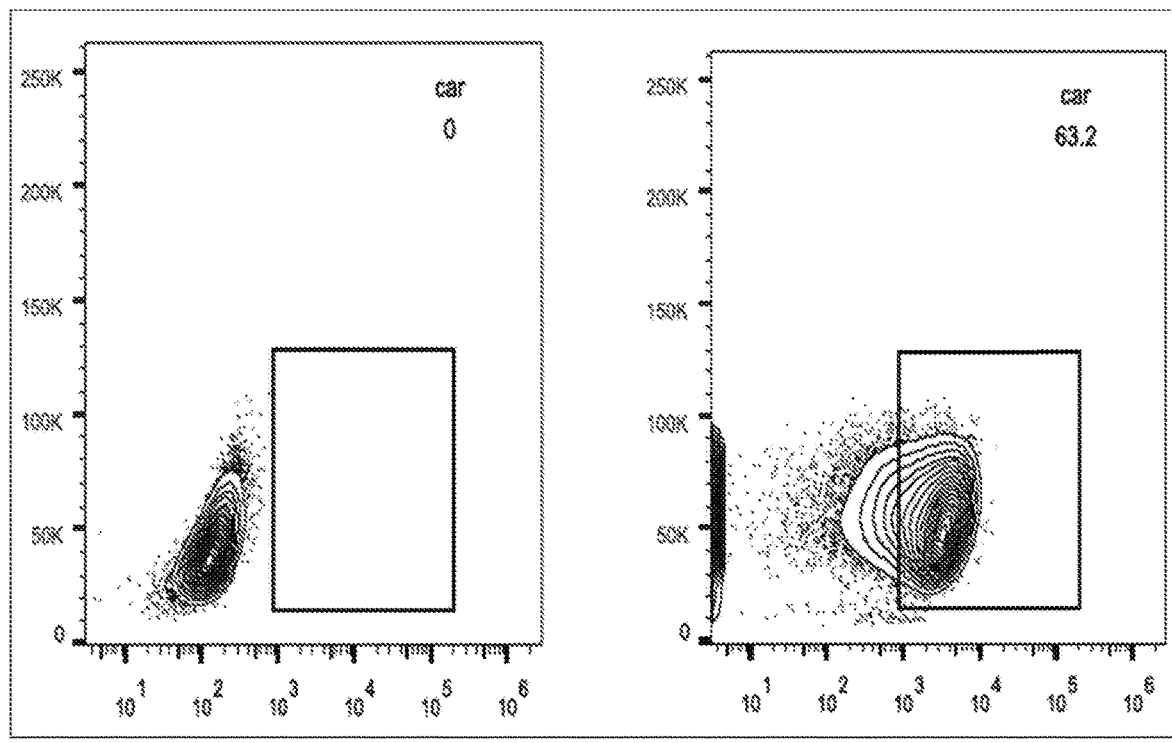
FIGS. 19A and 19B show knockout and infection efficiency of BCMA Car T cells.
Figure 19B:
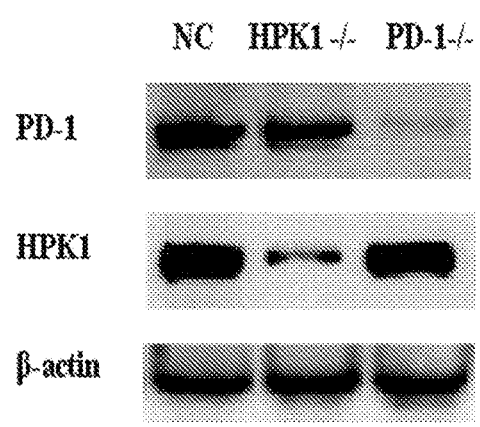
Figure 21A:
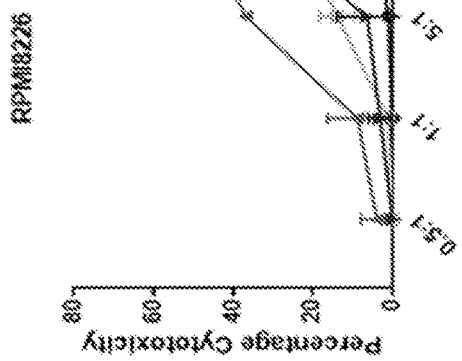
FIGS. 21A-21D present graphs showing that HPK-1 edited Car T cells exhibit enhanced antitumor efficacy in vitro. T cell and CAR-BCMA T cell were co-cultured with U266 (21A), RPMI8226 (21B), K562 (21C) and K562-BCMA (21D), after 12 h, cytotoxicity was tested.*: P<0.001, : P<0.01, *: P<0.05.
Figure 21B:
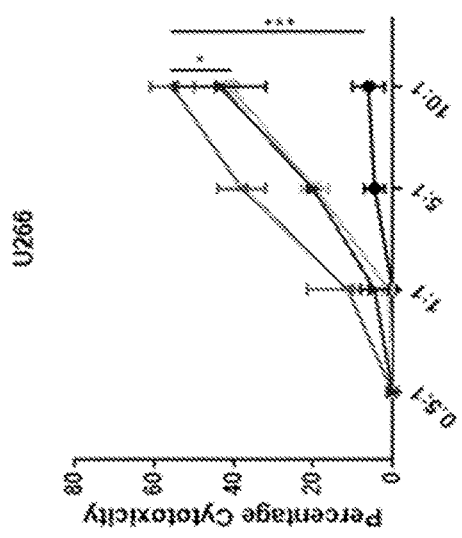
Figure 21C:
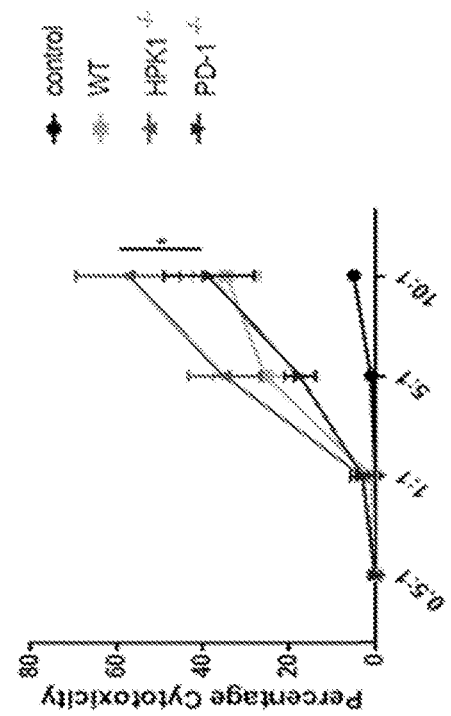
Figure 21D:
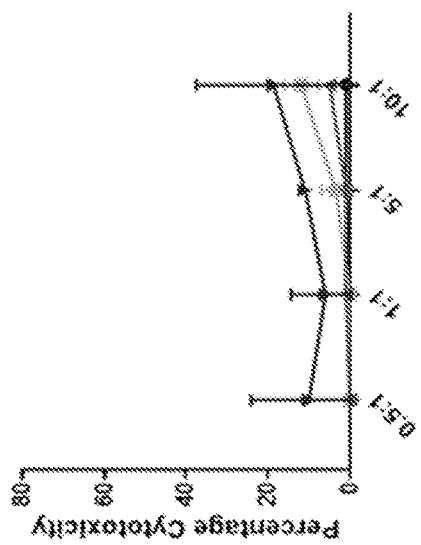

HPK-1 knockout efficiency was assessed following the same procedure described in Example 5 by Western Blot and BCMA Car expression was evaluated by FACS. As shown in FIG. 19A, BCMA transduction using lentivirus was successful. FIG. 19B also shows that the gRNA/Cas9 was effective in knocking out HPK1 gene in BCMA Car T cells. Similar to those observed in the CD19 CAR T cells, knocking out HPK1 gene also significantly reduced the expression of PD1 on the T cell surface, and is substantially the same as the PD-1 knockout CAR T cells. See FIG. 20.

Example 13. In Vitro Efficacy of HPK-1 Gene Knockout BCMA Car T Cells

This example studies the in vitro behavior of HPK-1 knockout BCMA CAR T cells.

Figure 22:
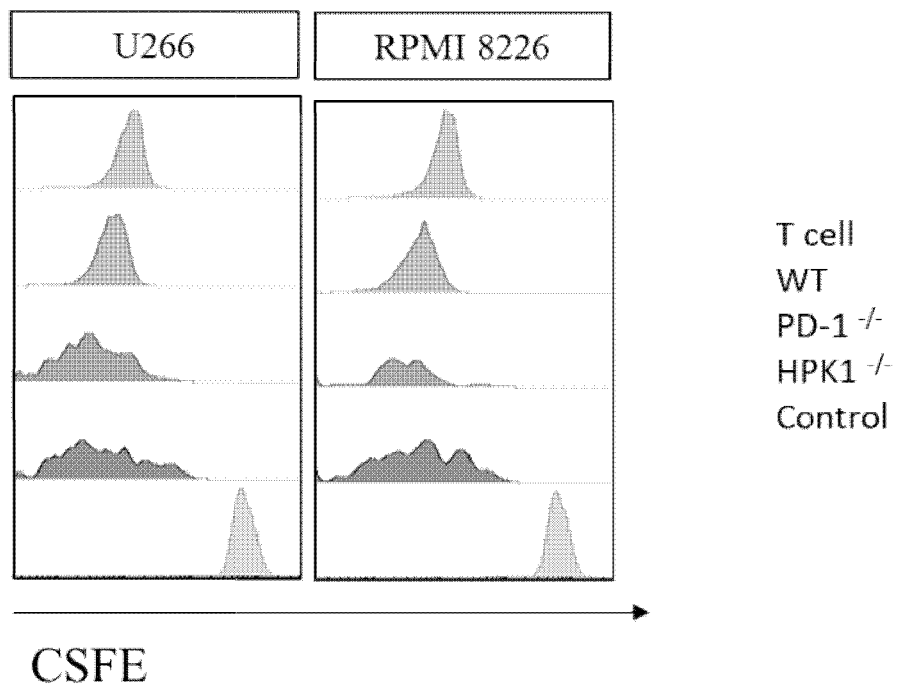
FIG. 22 presents images showing that HPK1 edited CAR T cells exhibit enhanced proliferation efficacy in vitro. T cell and CAR-BCMA T cell were incubated with CSFE and then co-cultured with U266 and RPMI8226, after 48 h, the cells were analyzed by flow cytometry.

This cytotoxicity study was performed according to the procedure described in Example 7. Briefly, T cell and CAR-BCMA T cells were co-cultured with U266, RPMI8226, K562 and K562-BCMA, after 12 h of culturing, cytotoxicity was measured. The results were shown in FIG. 21. As shown in FIG. 21, HPK1 knockout significantly enhances the cytotoxicity of BCMA CAR T cells in various cell lines. The improvement of cytotoxicity is also observed to be greater than PD-1 knockout. FIG. 22 also show that HPK1 edited BCMA Car T cells exhibit enhanced proliferation in vitro.

Example 14. In Vivo Efficacy of HPK-1 Gene Knockout BCMA Car T Cells

This example studies the in vivo behavior of HPK-1 knockout BCMA CAR T cells.

NSG mouse of 6-week old of age were transplanted with 10 mm$^3$ multiple myeloma tumor tissue. The mice were treated with 2×10$^6$ T cells or BCMA CAR-T cells via the tail vein at day 30 after the tumor reach 100 mm$^3$. Tumors were measured every 3-4 days. Mice that had no visible or palpable tumors that could be measured on consecutive measurement days were considered as "complete regressions". Animals were euthanized if they exhibited signs of distress or when the total tumor size reached 2,500 mm$^3$.

Figure 23:
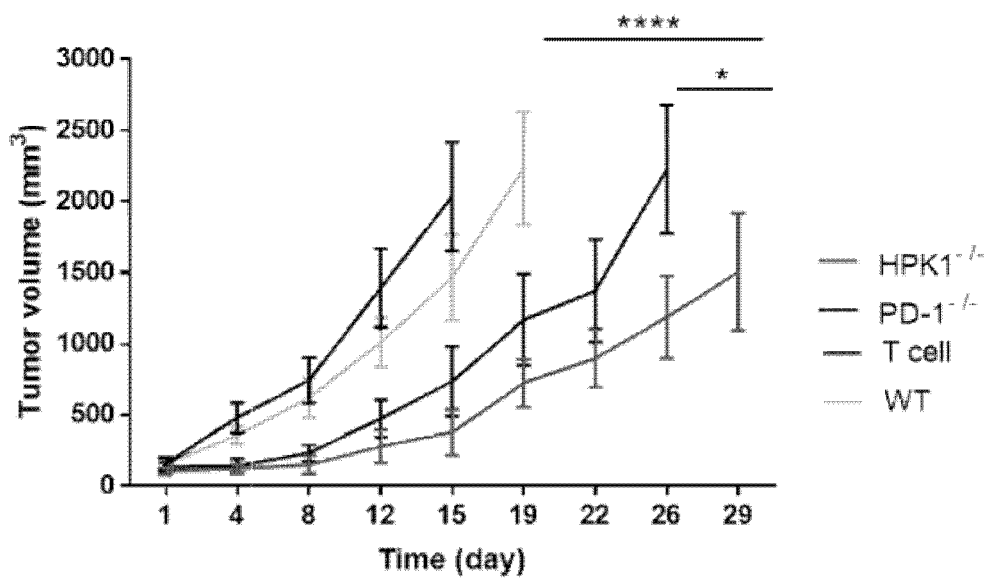
FIG. 23 present graphs showing that anti-BCMA CAR-transduced T cells significantly reduced tumor sizes in multiple myeloma PDX-model. For this study, the T cells were intravenous injected after the inoculated tumor size reaches 100 mm³, the tumor volume were then measure over the course of 29 days.

The results were shown in FIG. 23. As shown in FIG. 23, HPK1 knockout significantly enhances the efficacy of BCMA CAR T cells in this tumor model. Mice treated with HPK1$^-$BCMA Car T cells experiences the lowest tumor growth over the period of 33 days. FIG. 23 also shows that HPK1 knockout is more effective than PD1 knockout in enhancing the antitumor effect of BCMA CAR T cells.

Figure 24:
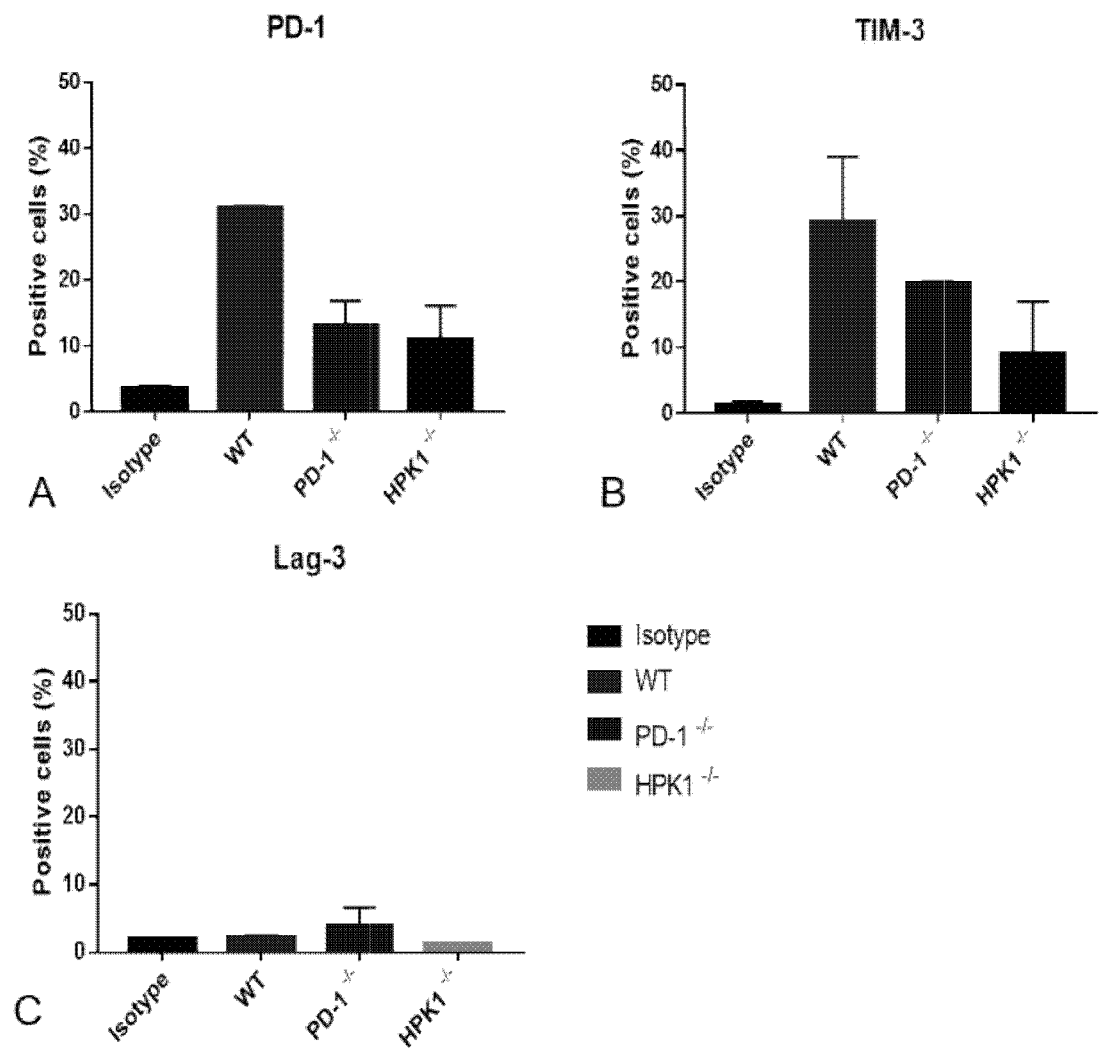
FIGS. 24A-24C are bar graphs showing that HPK-1 edited CAR T cells exhibit reduced T cell exhaustion in vivo. The graphs are based on flow cytometry analysis of T cell exhaustion markers 7 days after intravenous injection of the T cells.

Similar to the exhaustion marker studies observed for Her2 Car T cells, it was also found that HPK1 knockout ameliorate exhaustion of BCMA Car T cells in vivo. See FIG. 24.

The above is only the preferred embodiment of the present invention, but the scope of the present invention is not limited thereto. The modifications and changes that those skilled in the art can easily think of within the technical scope disclosed by the present invention, are intended to be covered by the scope of the present invention. Therefore, the protection scope of the invention should be determined by the protection scope of the claims.

What is claimed is:

1. A human immune cell comprising a genetic disruption of a HPK-1 gene, wherein the immune cell further comprises a recombinant receptor expressed on the surface of the immune cell or a polynucleotide encoding the recombinant receptor, wherein the recombinant receptor specifically binds to an antigen, and wherein the immune cell is capable of inducing enhanced cytotoxicity upon binding of the recombinant receptor to the antigen on a target cell compared to a control immune cell not comprising a genetic disruption of the HPK-1 gene.

2. The immune cell of claim 1, wherein the genetic disruption comprises a deletion, mutation, and/or insertion in the HPK-1 gene resulting in inactivation, reduced activity, and/or reduced expression of the HPK-1 gene.

3. The immune cell of claim 2, wherein the genetic disruption comprises a double stranded break (DSB) in the HPK-1 gene repaired by non-homologous end joining (NHEJ) that effects insertions and deletions in the HPK-1 gene an insertion or deletion in the HPK-1 gene that was generated by non-homologous end joining (NHEJ) of a double stranded break (DSB) induced in the HPK-1 gene.

4. The immune cell of claim 1 which is characterized by one or more of the following:
   a. the immune cell further comprises a genetic disruption of a gene encoding a PD-1 or PDL-1 polypeptide;
   b. the immune cell is a primary cell;
   c. the immune cell is CD3 positive;
   d. the immune cell is a T cell;
   e. the immune cell is a CD4+ or CD8+ T cell, CAR-T cell, NK T cell, alpha beta T cell or gamma delta T cell, or NK cell;
   f. the immune cell is derived from primary cells of a subject suffering from cancer;
   g. wherein the recombinant receptor is a recombinant T cell receptor or a chimeric antigen receptor;
   h. the recombinant receptor specifically binds to one or more antigens independently selected from ROR1, Her2, L1-CAM, CD19, CD20, CD22, CEA, hepatitis B surface antigen, anti-folate receptor, CD23, CD24, CD30, CD33, CD38, CD276, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule (CD171), MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), cyclin A1 (CCNA1), BCMA and interleukin 12; and
   i. the immune cell comprises a gRNA, wherein the gRNA comprises a targeting domain that is the same or differs no more than 3 nucleotides from a sequence fully complementary with a target sequence selected from SEQ ID NO: 1 and 11-15.

5. A cell population comprising the immune cell of claim 1, characterized by one or more of the following: (1) at least 50%, 60%, 65%, 70%, 75%, 80%, 85%, 90% or 95% of cells in the cell population do not express the endogenous HPK-1 polypeptide; do not contain a contiguous HPK-1 gene, a HPK-1 gene, and/or a functional HPK-1 gene; (2) a HPK-1 gene knockout efficiency in the cell population of at least 50%, 60%, 65%, 70%, 75%, 80%, 85%, 90% or 95%; (3) the percentage of cells in the cell population expressing PD-1, TIM-3, and/or Lag-3 on cell surface, as determined by flow cytometry, is lower than that in a control cell population; (4) the percentage of cells in the cell population expressing Annexin V on cell surface, as determined by flow cytometry, is lower than that in a control cell population; and (5) the percentage of cells in the cell population expressing CD107a on cell surface, as determined by flow cytometry, is higher than that in a control cell population.

6. A pharmaceutical composition comprising the immune cell of claim 1, and a pharmaceutically acceptable carrier.

* * * * *

SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: synthetic sequence

<400> SEQUENCE: 1

```
gacctggtgg cactgaaga                                                    19

<210> SEQ ID NO 2
<211> LENGTH: 20
<212> TYPE: DNA
<213> ORGANISM: Artificial Sequence
<220> FEATURE:
<223> OTHER INFORMATION: synthetic sequence

<400> SEQUENCE: 2
ggccaggatg gttcttaggt                                                   20

<210> SEQ ID NO 3
<211> LENGTH: 23
<212> TYPE: DNA
<213> ORGANISM: Artificial Sequence
<220> FEATURE:
<223> OTHER INFORMATION: synthetic sequence

<400> SEQUENCE: 3
tagggacctg gtggcactga aga                                               23

<210> SEQ ID NO 4
<211> LENGTH: 23
<212> TYPE: DNA
<213> ORGANISM: Artificial Sequence
<220> FEATURE:
<223> OTHER INFORMATION: synthetic sequence

<400> SEQUENCE: 4
aaactcttca gtgccaccag gtc                                               23

<210> SEQ ID NO 5
<211> LENGTH: 24
<212> TYPE: DNA
<213> ORGANISM: Artificial Sequence
<220> FEATURE:
<223> OTHER INFORMATION: synthetic sequence

<400> SEQUENCE: 5 tagggggccag gatggttctt aggt                                             24

<210> SEQ ID NO 6
<211> LENGTH: 24
<212> TYPE: DNA
<213> ORGANISM: Artificial Sequence
<220> FEATURE:
<223> OTHER INFORMATION: synthetic sequence

<400> SEQUENCE: 6
aaacacctaa gaaccatcct ggcc                                              24

<210> SEQ ID NO 7
<211> LENGTH: 19
<212> TYPE: DNA
<213> ORGANISM: Artificial Sequence
<220> FEATURE:
<223> OTHER INFORMATION: synthetic sequence

<400> SEQUENCE: 7
agcgagagtg aggaggggg                                                    19

<210> SEQ ID NO 8
<211> LENGTH: 22
<212> TYPE: DNA
```

```
<213> ORGANISM: Artificial Sequence
<220> FEATURE:
<223> OTHER INFORMATION: synthetic sequence

<400> SEQUENCE: 8
ttcatcacca gagataactc cc                                          22

<210> SEQ ID NO 9
<211> LENGTH: 39
<212> TYPE: DNA
<213> ORGANISM: Artificial Sequence
<220> FEATURE:
<223> OTHER INFORMATION: synthetic sequence

<400> SEQUENCE: 9
ccaccctctc cccagtccta cccctcctc accctcct                          39

<210> SEQ ID NO 10
<211> LENGTH: 39
<212> TYPE: DNA
<213> ORGANISM: Artificial Sequence
<220> FEATURE:
<223> OTHER INFORMATION: synthetic sequence

<400> SEQUENCE: 10
ggtccctcca gacccctcgc tccgggaccc ctgggctgc                        39

<210> SEQ ID NO 11
<211> LENGTH: 19
<212> TYPE: DNA
<213> ORGANISM: Artificial Sequence
<220> FEATURE:
<223> OTHER INFORMATION: synthetic sequence

<400> SEQUENCE: 11
gctcgagaca aggtgtcag                                              19

<210> SEQ ID NO 12
<211> LENGTH: 19
<212> TYPE: DNA
<213> ORGANISM: Artificial Sequence
<220> FEATURE:
<223> OTHER INFORMATION: synthetic sequence

<400> SEQUENCE: 12
aaggtgtcag gggacctgg                                              19

<210> SEQ ID NO 13
<211> LENGTH: 20
<212> TYPE: DNA
<213> ORGANISM: Artificial Sequence
<220> FEATURE:
<223> OTHER INFORMATION: synthetic sequence

<400> SEQUENCE: 13
accactatga cctgctacag                                             20

<210> SEQ ID NO 14
<211> LENGTH: 20
<212> TYPE: DNA
<213> ORGANISM: Artificial Sequence
<220> FEATURE:
<223> OTHER INFORMATION: synthetic sequence

<400> SEQUENCE: 14
gacctgctac agcggctggg                                             20
```

<210> SEQ ID NO 15
<211> LENGTH: 20
<212> TYPE: DNA
<213> ORGANISM: Artificial Sequence
<220> FEATURE:
<223> OTHER INFORMATION: synthetic sequence

<400> SEQUENCE: 15
gctgggtggc ggcacgtatg                                        20

<210> SEQ ID NO 16
<211> LENGTH: 2819
<212> TYPE: DNA
<213> ORGANISM: Homo sapiens

<400> SEQUENCE: 16
agcgagagtg aggaggggggg aggccacagc ccgcggaggc aaggcgggtg cagggcttct    60
ggggacggag ggaggtgcca gaagttgagc cctgaggccc tgctggcccc tgggcgcagg   120
cccagctcag gccccagggg atggacgtcg tggaccctga cattttcaat agagaccccc   180 ggaccacta tgacctgcta cagcggctgg gtggcggcac gtatgggaa gtctttaagg    240 ctcgagacaa ggtgtcaggg acctggtgg cactgaagat ggtgaagatg gagcctgatg    300
atgatgtctc caccccttcag aaggaaatcc tcatattgaa acttgccgg cacgccaaca   360 tcgtggccta ccatgggagt tatctctggt tgcagaaact ctggatctgc atggaattct   420 gtgggggctgg ttctctccag acatctacc aagtgacagg ctccctgtca gagctccaga   480
ttagctatgt ctgccgggaa gtgctccagg actggcctat tttgcactca cagaagaaga   540
tacacaggga catcaaggga gctaacatcc tcatcaatga tgctggggag gtcagattgg   600
ctgactttgg catctcggcc cagattgggg ctacactggc cagacgcctc tctttcattg   660
ggacacccta ctggatggct ccggaagtgg cagctgtggc cctgaaggga ggatacaatg   720
agctgtgtga catctggtcc ctgggcatca cggccatcga actggccgag ctacagccac   780
cgctctttga tgtgcaccct ctcagagttc tcttcctcat gaccaagagt ggctaccagc   840
ctccccgact gaaggaaaaaa ggcaaatggt cggctgcctt ccacaacttc atcaaagtca   900
ctctgactaa gagtcccaag aaacgaccca gcgccaccaa gatgctcagt catcaactgg   960
tatcccagcc tgggctgaat cgaggcctga tcctggatct tcttgacaaa ctgaagaatc  1020
ccgggaaagg acctccatt ggggacattg aggatgagga gcccgagcta ccccctgcta  1080
tccctcggcg gatcagatcc acccaccgct ccagctctct ggggatccca gatgcagact  1140
gctgtcggcg gcacatggag ttcaggaagc tccgaggaat ggagaccaga cccccagcca  1200
acaccgctcg cctacagcct cctcgagacc tcaggagcag cagccccagg aagcaactgt  1260
cagagtcgtc tgacgatgac tatgacgacg tggacatccc caccccctgca gaggacacac  1320 ctcctccact tcccccaaag cccaagttcc gttctccatc agacgagggt cctgggagca  1380 tggggatga tgggcagctg agcccggggg tgctggtccg gtgtgccagt gggccccac    1440 caaacagccc ccgtcctggg cctcccccat ccaccagcag cccccacctc accgcccatt   1500
cagaaccctc actctggaac ccaccctccc gggagcttga caagccccca cttctgcccc   1560
ccaagaagga aagatgaag agaaagggat gtgcccttct cgtaaagttg ttcaatggct   1620
gccccctccg gatccacagc acggccgcct ggacacatcc ctccaccaag gaccagcacc   1680
tgctcctggg ggcagaggaa ggcatcttca tcctgaaccg gaatgaccag gaggccacgc   1740

| | |
|---|---|
| tggaaatgct ctttcctagc cggactacgt gggtgtactc catcaacaac gttctcatgt | 1800 |
| ctctctcagg aaagaccccc cacctgtatt ctcatagcat ccttggcctg ctggaacgga | 1860 |
| aagagaccag agcaggaaac cccatcgctc acattagccc ccaccgccta ctggcaagga | 1920 |
| agaacatggt ttccaccaag atccaggaca ccaaaggctg ccgggcgtgc tgtgtggcgg | 1980 |
| agggtgcgag ctctgggggc ccgttcctgt gcggtgcatt ggagacgtcc gttgtcctgc | 2040 |
| ttcagtggta ccagcccatg aacaaattcc tgcttgtccg gcaggtgctg ttcccactgc | 2100 |
| cgacgcctct gtccgtgttc gcgctgctga ccgggccagg ctctgagctg cccgctgtgt | 2160 |
| gcatcggcgt gagccccggg cggccgggga agtcggtgct cttccacacg gtgcgctttg | 2220 |
| gcgcgctctc ttgctggctg ggcgagatga gcaccgagca caggggaccc gtgcaggtga | 2280 |
| cccaggtaga ggaagatatg tgatggtgt tgatggatgg ctctgtgaag ctggtgaccc | 2340 |
| cggaggggtc cccagtccgg ggacttcgca cacctgagat ccccatgacc gaagcggtgg | 2400 |
| aggccgtggc tatggttgga ggtcagcttc aggccttctg gaagcatgga gtgcaggtgt | 2460 |
| gggctctagg ctcggatcag ctgctacagg agctgagaga ccctaccctc actttccgtc | 2520 |
| tgcttggctc ccccaggctg gagtgcagtg gcacgatctc gcctcactgc aacctcctcc | 2580 |
| tcccaggttc aagcaattct cctgcctcag cctcccgagt agctgggatt acaggcctgt | 2640 |
| agtggtggag acacgcccag tggatgatcc tactgctccc agcaacctct acatccagga | 2700 |
| atgagtccct aggggggtgt caggaactag tccttgcacc ccctccccca tagacacact | 2760 |
| agtggtcatg gcatgtcctc atctcccaat aaacatgact ttagcctctg ctaaaaaaa | 2819 |

<210> SEQ ID NO 17
<211> LENGTH: 2721
<212> TYPE: DNA
<213> ORGANISM: Homo sapiens

<400> SEQUENCE: 17

| | |
|---|---|
| agcgagagtg aggaggggg aggccacagc ccgcggaggc aaggcgggtg cagggcttct | 60 |
| ggggacggag ggaggtgcca gaagttgagc cctgaggccc tgctggcccc tgggcgcagg | 120 |
| cccagctcag gcccccaggg atggacgtcg tggaccctga cattttcaat agagaccccc | 180 |
| gggaccacta tgacctgcta cagcggctgg gtggcggcac gtatggggaa gtctttaagg | 240 |
| ctcgagacaa ggtgtcaggg gacctggtgg cactgaagat ggtgaagatg gagcctgatg | 300 |
| atgatgtctc caccctttcag aaggaaatcc tcatattgaa aacttgccgg cacgccaaca | 360 |
| tcgtggccta ccatgggagt tatctctggt tgcagaaact ctggatctgc atggaattct | 420 |
| gtgggctgg ttctctccag gacatctacc aagtgacagg ctccctgtca gagctccaga | 480 |
| ttagctatgt ctgccgggaa gtgctccagg gactggccta tttgcactca cagaagaaga | 540 |
| tacacaggga catcaaggga gctaacatcc tcatcaatga tgctggggag gtcagattgg | 600 |
| ctgactttgg catctcggcc cagattgggc tacactggc cagacgcctc tctttcattg | 660 |
| ggacacccta ctggatggct ccggaagtgg cagctgtggc cctgaaggga ggatacaatg | 720 |
| agctgtgtga catctggtcc ctgggcatca cggccatcga actggccgag ctacagccac | 780 |
| cgctctttga tgtgcaccct ctcagagttc tcttcctcat gaccaagagt ggctaccagc | 840 |
| ctcccccgact gaaggaaaaa ggcaaatggt cggctgcctt ccacaacttc atcaaagtca | 900 |
| ctctgactaa gagtcccaag aaacgaccca gcgccaccaa gatgctcagt catcaactgg | 960 |
| tatcccagcc tgggctgaat cgaggcctga tcctggatct tcttgacaaa ctgaagaatc | 1020 |
| ccgggaaagg accctccatt ggggacattg aggatgagga gcccgagcta ccccctgcta | 1080 |

```
tccctcggcg atcagatcc acccaccgct ccagctctct ggggatccca gatgcagact    1140
gctgtcggcg gcacatggag ttcaggaagc tccgaggaat ggagaccaga cccccagcca    1200
acaccgctcg cctacagcct cctcgagacc tcaggagcag cagccccagg aagcaactgt    1260
cagagtcgtc tgacgatgac tatgacgacg tggacatccc caccccctgca gaggacacac    1320 ctcctccact tcccccccaag cccaagttcc gttctccatc agacgagggt cctgggagca    1380
tgggggatga tgggcagctg agcccggggg tgctggtccg gtgtgccagt gggcccccac    1440
caaacagccc ccgtcctggg cctcccccat ccaccagcag ccccccacctc accgcccatt    1500 cagaaccctc actctggaac ccaccctccc gggagcttga caagccccca cttctgcccc    1560
ccaagaagga aaagatgaag agaaagggat gtgcccttct cgtaaagttg ttcaatggct    1620 gcccctccg gatccacagc acggccgcct ggacacatcc ctccaccaag gaccagcacc    1680
tgctcctggg ggcagaggaa ggcatcttca tcctgaaccg gaatgaccag gaggccacgc    1740
tggaaatgct ctttcctagc cggactacgt gggtgtactc catcaacaac gttctcatgt    1800
ctctctcagg aaagacccccc cacctgtatt ctcatagcat ccttggcctg ctggaacgga    1860
aagagaccag agcaggaaac cccatcgctc acattagccc ccaccgccta ctggcaagga    1920
agaacatggt ttccaccaag atccaggaca ccaaaggctg ccgggcgtgc tgtgtggcgg    1980
agggtgcgag ctctggggc ccgttcctgt gcggtgcatt ggagacgtcc gttgtcctgc    2040
ttcagtggta ccagcccatg aacaaattcc tgcttgtccg gcaggtgctg ttcccactgc    2100
cgacgcctct gtccgtgttc gcgctgctga ccgggccagg ctctgagctg cccgctgtgt    2160
gcatcggcgt gagccccggg cggccgggga agtcggtgct cttccacacg gtgcgctttg    2220
gcgcgctctc ttgctggctg ggcgagatga gcaccgagca caggggaccc gtgcaggtga    2280
cccaggtaga ggaagatatg gtgatggtgt tgatggatgg ctctgtgaag ctggtgaccc    2340
cggaggggtc cccagtccgg ggacttcgca cacctgagat ccccatgacc gaagcggtgg    2400
aggccgtggc tatggttgga ggtcagcttc aggccttctg gaagcatgga gtgcaggtgt    2460
gggctctagg ctcggatcag ctgctacagg agctgagaga ccctaccctc actttccgtc    2520
tgcttggctc ccccaggcct gtagtggtgg agacacgccc agtggatgat cctactgctc    2580
ccagcaacct ctacatccag gaatgagtcc ctagggggt gtcaggaact agtccttgca    2640 cccccctcccc catagacaca ctagtggtca tggcatgtcc tcatctccca ataaacatga    2700
ctttagcctc tgctaaaaaa a                                              2721
```

<210> SEQ ID NO 18
<211> LENGTH: 4206
<212> TYPE: DNA
<213> ORGANISM: Artificial Sequence
<220> FEATURE:
<223> OTHER INFORMATION: synthetic sequence

<400> SEQUENCE: 18

```
atggcccaa agaagaagcg gaaggtcggt atccacggtg tcccagcagc catggacaag    60
aagtactcca ttgggctcga tatcggcaca aacagcgtcg gctgggccgt cattacggac    120
gagtacaagg tgccgagcaa aaaattcaaa ggtctgggca taccgatcg ccacagcata    180 aagaagaacc tcattggcgc cctcctgttc gactccgggg agacggccga agccacgcgg    240
ctcaaaagaa cagcacggcg cagatatacc cgcagaaaga tcggatctg ctacctgcag    300 gagatcttta gtaatgagat ggctaaggtg gatgactctt tcttccatag gctggaggag    360
```

```
tcctttttgg tggaggagga taaaaagcac gagcgccacc caatctttgg caatatcgtg      420
gacgaggtgg cgtaccatga aaagtaccca accatatatc atctgaggaa gaagcttgta      480
gacagtactg ataaggctga cttgcggttg atctatctcg cgctggcgca tatgatcaaa      540
tttcggggac acttcctcat cgaggggac ctgaacccag acaacagcga tgtcgacaaa       600
ctctttatcc aactggttca gacttacaat cagcttttcg aagagaaccc gatcaacgca      660
tccggagttg acgccaaagc aatcctgagc gctaggctgt ccaaatcccg gcggctcgaa      720
aacctcatcg cacagctccc tggggagaag aagaacggcc tgtttggtaa tcttatcgcc      780
ctgtcactcg ggctgacccc caactttaaa tctaacttcg acctggccga agatgccaag      840
cttcaactga gcaaagacac ctacgatgat gatctcgaca atctgctggc ccagatcggc      900
gaccagtacg cagacctttt tttggcggca aagaacctgt cagacgccat tctgctgagt      960
gatattctgc gagtgaacac ggagatcacc aaagctccgc tgagcgctag tatgatcaag     1020
cgctatgatg agcaccacca agacttgact ttgctgaagg cccttgtcag acagcaactg     1080
cctgagaagt acaaggaaat tttcttcgat cagtctaaaa atggctacgc cggatacatt     1140
gacggcggag caagccagga ggaattttac aaatttatta agcccatctt ggaaaaaatg     1200
gacggcaccg aggagctgct ggtaaagctt aacagagaag atctgttgcg caaacagcgc     1260
actttcgaca atggaagcat cccccaccag attcacctgg gcgaactgca cgctatactc     1320
aggcggcaag aggatttcta ccccttttg aaagataaca gggaaaagat tgagaaaatc      1380
ctcacatttc ggatacccta ctatgtaggc cccctcgccc ggggaaattc cagattcgcg     1440
tggatgactc gcaaatcaga agagaccatc actccctgga acttcgagga agtcgtggat     1500
aagggggcct ctgcccagtc cttcatcgaa aggatgacta actttgataa aaatctgcct     1560
aacgaaaagg tgcttcctaa acactctctg ctgtacgagt acttcacagt ttataacgag     1620
ctcaccaagg tcaaatacgt cacagaaggg atgagaaagc cagcattcct gtctggagag     1680
cagaagaaag ctatcgtgga cctcctcttc aagacgaacc ggaaagttac cgtgaaacag     1740
ctcaaagaag actatttcaa aaagattgaa tgtttcgact ctgttgaaat cagcggagtg     1800
gaggatcgct tcaacgcatc cctgggaacg tatcacgatc tcctgaaaat cattaaagac     1860
aaggacttcc tggacaatga ggagaacgag gacattcttg aggacattgt cctcacccctt    1920 acgttgtttg aagataggga gatgattgaa gaacgcttga aaacttacgc tcatctcttc     1980
gacgacaaag tcatgaaaca gctcaagagg cgccgatata caggatgggg gcggctgtca     2040
agaaaactga tcaatgggat ccgagacaag cagagtggaa agacaatcct ggattttctt     2100
aagtccgatg gatttgccaa ccggaacttc atgcagttga tccatgatga ctctctcacc     2160
tttaaggagg acatccagaa agcacaagtt tctggccagg gggacagtct tcacgagcac     2220
atcgctaatc ttgcaggtag cccagctatc aaaaagggaa tactgcagac cgttaaggtc     2280
gtggatgaac tcgtcaaagt aatgggaagg cataagcccg agaatatcgt tatcgagatg     2340
gcccgagaga accaaactac ccagaaggga cagaagaaca gtagggaaag gatgaagagg     2400
attgaagagg gtataaaaga actggggtcc caaatcctta aggaacaccc agttgaaaac     2460
acccagcttc agaatgagaa gctctacctg tactacctgc agaacggcag ggacatgtac     2520
gtggatcagg aactggacat caatcggctc tccgactacg acgtggatca tatcgtgccc     2580 cagtctttc tcaaagatga ttctattgat aataaagtgt tgacaagatc cgataaaaat      2640
agagggaaga gtgataacgt cccctcagaa gaagttgtca gaaaatgaa aaattattgg      2700 cggcagctgc tgaacgccaa actgatcaca caacggaagt tcgataatct gactaaggct     2760
```

```
gaacgaggtg gcctgtctga gttggataaa gcaggcttca tcaaaaggca gcttgttgag    2820
acacgccaga tcaccaagca cgtggcccaa attctcgatt cacgcatgaa caccaagtac    2880
gatgaaaatg acaaactgat tcgagaggtg aaagttatta ctctgaagtc taagctggtc    2940
tcagatttca gaaggacttt tcagtttat aaggtgagag agatcaacaa ttaccaccat     3000
gcgcatgatg cctacctgaa tgcagtggta ggcactgcac ttatcaaaaa atatcccaag    3060
cttgaatctg aatttgttta cggagactat aaagtgtacg atgttaggaa aatgatcgca    3120
aagtctgagc aggaaatagg caaggccacc gctaagtact tcttttacag caatattatg    3180 aatttttca agaccgagat tacactggcc aatggagaga ttcggaagcg accacttatc     3240
gaaacaaacg gagaaacagg agaaatcgtg tgggacaagg gtagggattt cgcgacagtc    3300
cggaaggtcc tgtccatgcc gcaggtgaac atcgttaaaa agaccgaagt acagaccgga    3360
ggcttctcca aggaaagtat cctcccgaaa aggaacagcg acaagctgat cgcacgcaaa    3420
aaagattggg accccaagaa atacggcgga ttcgattctc ctacagtcgc ttacagtgta    3480
ctggttgtgg ccaaagtgga gaagggaag tctaaaaaac tcaaaagcgt caaggaactg     3540
ctgggcatca caatcatgga gcgatcaagc ttcgaaaaaa accccatcga ctttctcgag    3600
gcgaaaggat ataagaggt caaaaaagac ctcatcatta agcttcccaa gtactctctc     3660
tttgagcttg aaaacggccg gaaacgaatg ctcgctagtg cgggcgagct gcagaaaggt    3720
aacgagctgg cactgccctc taaatacgtt aatttcttgt atctggccag ccactatgaa    3780
aagctcaaag ggtctcccga agataatgag cagaagcagc tgttcgtgga acaacacaaa    3840
cactaccttg atgagatcat cgagcaaata agcgaattct ccaaaagagt gatcctcgcc    3900
gacgctaacc tcgataaggt gctttctgct tacaataagc acagggataa gcccatcagg    3960
gagcaggcag aaaacattat ccacttgttt actctgacca acttgggcgc gcctgcagcc    4020
ttcaagtact tcgacaccac catagacaga aagcggtaca cctctacaaa ggaggtcctg    4080
gacgccacac tgattcatca gtcaattacg gggctctatg aaacaagaat cgacctctct    4140
cagctcggtg gagacaagcg tcctgctgct actaagaaag ctggtcaagc taagaaaaag    4200
aaataa                                                               4206
```

<210> SEQ ID NO 19
<211> LENGTH: 1401
<212> TYPE: PRT
<213> ORGANISM: Artificial Sequence
<220> FEATURE:
<223> OTHER INFORMATION: synthetic sequence

<400> SEQUENCE: 19

```
Met Ala Pro Lys Lys Arg Lys Val Gly Ile His Gly Val Pro Ala
1               5                   10                  15

Ala Met Asp Lys Lys Tyr Ser Ile Gly Leu Asp Ile Gly Thr Asn Ser
                20                  25                  30

Val Gly Trp Ala Val Ile Thr Asp Glu Tyr Lys Val Pro Ser Lys Lys
            35                  40                  45

Phe Lys Val Leu Gly Asn Thr Asp Arg His Ser Ile Lys Lys Asn Leu
        50                  55                  60

Ile Gly Ala Leu Leu Phe Asp Ser Gly Glu Thr Ala Glu Ala Thr Arg
65                  70                  75                  80

Leu Lys Arg Thr Ala Arg Arg Arg Tyr Thr Arg Arg Lys Asn Arg Ile
                85                  90                  95
```

```
Cys Tyr Leu Gln Glu Ile Phe Ser Asn Glu Met Ala Lys Val Asp Asp
             100                 105                 110

Ser Phe Phe His Arg Leu Glu Glu Ser Phe Leu Val Glu Glu Asp Lys
    115                 120                 125

Lys His Glu Arg His Pro Ile Phe Gly Asn Ile Val Asp Glu Val Ala
    130                 135                 140

Tyr His Glu Lys Tyr Pro Thr Ile Tyr His Leu Arg Lys Lys Leu Val
145                 150                 155                 160

Asp Ser Thr Asp Lys Ala Asp Leu Arg Leu Ile Tyr Leu Ala Leu Ala
                165                 170                 175

His Met Ile Lys Phe Arg Gly His Phe Leu Ile Glu Gly Asp Leu Asn
            180                 185                 190

Pro Asp Asn Ser Asp Val Asp Lys Leu Phe Ile Gln Leu Val Gln Thr
        195                 200                 205

Tyr Asn Gln Leu Phe Glu Glu Asn Pro Ile Asn Ala Ser Gly Val Asp
    210                 215                 220

Ala Lys Ala Ile Leu Ser Ala Arg Leu Ser Lys Ser Arg Arg Leu Glu
225                 230                 235                 240

Asn Leu Ile Ala Gln Leu Pro Gly Glu Lys Lys Asn Gly Leu Phe Gly
                245                 250                 255

Asn Leu Ile Ala Leu Ser Leu Gly Leu Thr Pro Asn Phe Lys Ser Asn
            260                 265                 270

Phe Asp Leu Ala Glu Asp Ala Lys Leu Gln Leu Ser Lys Asp Thr Tyr
        275                 280                 285

Asp Asp Asp Leu Asp Asn Leu Leu Ala Gln Ile Gly Asp Gln Tyr Ala
    290                 295                 300

Asp Leu Phe Leu Ala Ala Lys Asn Leu Ser Asp Ala Ile Leu Leu Ser
305                 310                 315                 320

Asp Ile Leu Arg Val Asn Thr Glu Ile Thr Lys Ala Pro Leu Ser Ala
                325                 330                 335

Ser Met Ile Lys Arg Tyr Asp Glu His His Gln Asp Leu Thr Leu Leu
            340                 345                 350

Lys Ala Leu Val Arg Gln Gln Leu Pro Glu Lys Tyr Lys Glu Ile Phe
        355                 360                 365

Phe Asp Gln Ser Lys Asn Gly Tyr Ala Gly Tyr Ile Asp Gly Gly Ala
    370                 375                 380

Ser Gln Glu Glu Phe Tyr Lys Phe Ile Lys Pro Ile Leu Glu Lys Met
385                 390                 395                 400

Asp Gly Thr Glu Glu Leu Leu Val Lys Leu Asn Arg Glu Asp Leu Leu
                405                 410                 415

Arg Lys Gln Arg Thr Phe Asp Asn Gly Ser Ile Pro His Gln Ile His
            420                 425                 430

Leu Gly Glu Leu His Ala Ile Leu Arg Arg Gln Glu Asp Phe Tyr Pro
        435                 440                 445

Phe Leu Lys Asp Asn Arg Glu Lys Ile Glu Lys Ile Leu Thr Phe Arg
    450                 455                 460

Ile Pro Tyr Tyr Val Gly Pro Leu Ala Arg Gly Asn Ser Arg Phe Ala
465                 470                 475                 480

Trp Met Thr Arg Lys Ser Glu Glu Thr Ile Thr Pro Trp Asn Phe Glu
                485                 490                 495

Glu Val Val Asp Lys Gly Ala Ser Ala Gln Ser Phe Ile Glu Arg Met
            500                 505                 510

Thr Asn Phe Asp Lys Asn Leu Pro Asn Glu Lys Val Leu Pro Lys His
```

-continued

```
            515                 520                 525
Ser Leu Leu Tyr Glu Tyr Phe Thr Val Tyr Asn Glu Leu Thr Lys Val
530                 535                 540

Lys Tyr Val Thr Glu Gly Met Arg Lys Pro Ala Phe Leu Ser Gly Glu
545                 550                 555                 560

Gln Lys Lys Ala Ile Val Asp Leu Leu Phe Lys Thr Asn Arg Lys Val
                    565                 570                 575

Thr Val Lys Gln Leu Lys Glu Asp Tyr Phe Lys Ile Glu Cys Phe
                    580                 585                 590

Asp Ser Val Glu Ile Ser Gly Val Glu Asp Arg Phe Asn Ala Ser Leu
                    595                 600                 605

Gly Thr Tyr His Asp Leu Leu Lys Ile Ile Lys Asp Lys Asp Phe Leu
            610                 615                 620

Asp Asn Glu Glu Asn Glu Asp Ile Leu Glu Asp Ile Val Leu Thr Leu
625                 630                 635                 640

Thr Leu Phe Glu Asp Arg Glu Met Ile Glu Glu Arg Leu Lys Thr Tyr
                    645                 650                 655

Ala His Leu Phe Asp Asp Lys Val Met Lys Gln Leu Lys Arg Arg Arg
            660                 665                 670

Tyr Thr Gly Trp Gly Arg Leu Ser Arg Lys Leu Ile Asn Gly Ile Arg
            675                 680                 685

Asp Lys Gln Ser Gly Lys Thr Ile Leu Asp Phe Leu Lys Ser Asp Gly
    690                 695                 700

Phe Ala Asn Arg Asn Phe Met Gln Leu Ile His Asp Asp Ser Leu Thr
705                 710                 715                 720

Phe Lys Glu Asp Ile Gln Lys Ala Gln Val Ser Gly Gln Gly Asp Ser
                    725                 730                 735

Leu His Glu His Ile Ala Asn Leu Ala Gly Ser Pro Ala Ile Lys Lys
            740                 745                 750

Gly Ile Leu Gln Thr Val Lys Val Val Asp Glu Leu Val Lys Val Met
    755                 760                 765

Gly Arg His Lys Pro Glu Asn Ile Val Ile Glu Met Ala Arg Glu Asn
    770                 775                 780

Gln Thr Thr Gln Lys Gly Gln Lys Asn Ser Arg Glu Arg Met Lys Arg
785                 790                 795                 800

Ile Glu Glu Gly Ile Lys Glu Leu Gly Ser Gln Ile Leu Lys Glu His
                    805                 810                 815

Pro Val Glu Asn Thr Gln Leu Gln Asn Glu Lys Leu Tyr Leu Tyr Tyr
            820                 825                 830

Leu Gln Asn Gly Arg Asp Met Tyr Val Asp Gln Glu Leu Asp Ile Asn
            835                 840                 845

Arg Leu Ser Asp Tyr Asp Val Asp His Ile Val Pro Gln Ser Phe Leu
            850                 855                 860

Lys Asp Asp Ser Ile Asp Asn Lys Val Leu Thr Arg Ser Asp Lys Asn
865                 870                 875                 880

Arg Gly Lys Ser Asp Asn Val Pro Ser Glu Glu Val Val Lys Lys Met
                    885                 890                 895

Lys Asn Tyr Trp Arg Gln Leu Leu Asn Ala Lys Leu Ile Thr Gln Arg
                    900                 905                 910

Lys Phe Asp Asn Leu Thr Lys Ala Glu Arg Gly Gly Leu Ser Glu Leu
            915                 920                 925

Asp Lys Ala Gly Phe Ile Lys Arg Gln Leu Val Glu Thr Arg Gln Ile
            930                 935                 940
```

-continued

```
Thr Lys His Val Ala Gln Ile Leu Asp Ser Arg Met Asn Thr Lys Tyr
945                 950                 955                 960

Asp Glu Asn Asp Lys Leu Ile Arg Glu Val Lys Val Ile Thr Leu Lys
                965                 970                 975

Ser Lys Leu Val Ser Asp Phe Arg Lys Asp Phe Gln Phe Tyr Lys Val
            980                 985                 990

Arg Glu Ile Asn Asn Tyr His His Ala His Asp Ala Tyr Leu Asn Ala
        995                 1000                1005

Val Val Gly Thr Ala Leu Ile Lys Lys Tyr Pro Lys Leu Glu Ser
    1010                1015                1020

Glu Phe Val Tyr Gly Asp Tyr Lys Val Tyr Asp Val Arg Lys Met
    1025                1030                1035

Ile Ala Lys Ser Glu Gln Glu Ile Gly Lys Ala Thr Ala Lys Tyr
    1040                1045                1050

Phe Phe Tyr Ser Asn Ile Met Asn Phe Phe Lys Thr Glu Ile Thr
    1055                1060                1065

Leu Ala Asn Gly Glu Ile Arg Lys Arg Pro Leu Ile Glu Thr Asn
    1070                1075                1080

Gly Glu Thr Gly Glu Ile Val Trp Asp Lys Gly Arg Asp Phe Ala
    1085                1090                1095

Thr Val Arg Lys Val Leu Ser Met Pro Gln Val Asn Ile Val Lys
    1100                1105                1110

Lys Thr Glu Val Gln Thr Gly Gly Phe Ser Lys Glu Ser Ile Leu
    1115                1120                1125

Pro Lys Arg Asn Ser Asp Lys Leu Ile Ala Arg Lys Lys Asp Trp
    1130                1135                1140

Asp Pro Lys Lys Tyr Gly Gly Phe Asp Ser Pro Thr Val Ala Tyr
    1145                1150                1155

Ser Val Leu Val Val Ala Lys Val Glu Lys Gly Lys Ser Lys Lys
    1160                1165                1170

Leu Lys Ser Val Lys Glu Leu Leu Gly Ile Thr Ile Met Glu Arg
    1175                1180                1185

Ser Ser Phe Glu Lys Asn Pro Ile Asp Phe Leu Glu Ala Lys Gly
    1190                1195                1200

Tyr Lys Glu Val Lys Lys Asp Leu Ile Ile Lys Leu Pro Lys Tyr
    1205                1210                1215

Ser Leu Phe Glu Leu Glu Asn Gly Arg Lys Arg Met Leu Ala Ser
    1220                1225                1230

Ala Gly Glu Leu Gln Lys Gly Asn Glu Leu Ala Leu Pro Ser Lys
    1235                1240                1245

Tyr Val Asn Phe Leu Tyr Leu Ala Ser His Tyr Glu Lys Leu Lys
    1250                1255                1260

Gly Ser Pro Glu Asp Asn Glu Gln Lys Gln Leu Phe Val Glu Gln
    1265                1270                1275

His Lys His Tyr Leu Asp Glu Ile Ile Glu Gln Ile Ser Glu Phe
    1280                1285                1290

Ser Lys Arg Val Ile Leu Ala Asp Ala Asn Leu Asp Lys Val Leu
    1295                1300                1305

Ser Ala Tyr Asn Lys His Arg Asp Lys Pro Ile Arg Glu Gln Ala
    1310                1315                1320

Glu Asn Ile Ile His Leu Phe Thr Leu Thr Asn Leu Gly Ala Pro
    1325                1330                1335
```

-continued

```
Ala Ala Phe Lys Tyr Phe Asp Thr Thr Ile Asp Arg Lys Arg Tyr
    1340            1345            1350

Thr Ser Thr Lys Glu Val Leu Asp Ala Thr Leu Ile His Gln Ser
    1355            1360            1365

Ile Thr Gly Leu Tyr Glu Thr Arg Ile Asp Leu Ser Gln Leu Gly
    1370            1375            1380

Gly Asp Lys Arg Pro Ala Ala Thr Lys Lys Ala Gly Gln Ala Lys
    1385            1390            1395

Lys Lys Lys
    1400
```